US006261800B1

(12) United States Patent
Nikolics et al.

(10) Patent No.: US 6,261,800 B1
(45) Date of Patent: Jul. 17, 2001

(54) LUTEINIZING HORMONE/ CHORIOGONADOTROPIN (LH/CG) RECEPTOR

(75) Inventors: Karoly Nikolics, San Carlos; Keith C. McFarland, Berkeley, both of CA (US); Deborah L. Segaloff, Iowa City, IA (US); Peter H. Seeburg, Heidelberg (DE)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/207,814

(22) Filed: Mar. 7, 1994

Related U.S. Application Data

(63) Continuation of application No. 07/781,153, filed on Oct. 31, 1991, now abandoned, which is a continuation of application No. PCT/US90/02488, filed on May 4, 1991, which is a continuation-in-part of application No. 07/347,683, filed on May 5, 1989, now abandoned.

(51) Int. Cl.$^7$ .............................. C07H 21/00; C12N 15/12

(52) U.S. Cl. ..................... 435/69.1; 435/325; 435/252.3; 435/252.33; 435/254.2; 435/320.1; 536/23.5; 935/9

(58) Field of Search ......................... 514/8, 12; 536/23.5; 435/69.1, 320.2, 252.3, 252.33, 240.2, 172.3, 325, 361, 362, 254.2; 935/9

(56) References Cited

U.S. PATENT DOCUMENTS

| | | |
|---|---|---|
| 4,560,649 | 12/1985 | Saxena et al. . |
| 4,921,808 | 5/1990 | Schneyer et al. . |

FOREIGN PATENT DOCUMENTS

| | | |
|---|---|---|
| 0 108 633 | 5/1984 | (EP) . |
| 0192392 | 8/1986 | (EP) . |
| WO 91/03483 | 3/1991 | (WO) . |
| WO 91/09121 | 6/1991 | (WO) . |
| WO 91/09137 | 6/1991 | (WO) . |
| WO 91/10735 | 7/1991 | (WO) . |

OTHER PUBLICATIONS

Ascoli, M. and Segaloff, D.,*J. Biol. Chem.* 261(8):3807–3815 (1986).

Ascoli, M., In: *The Receptors,* (Conn, P.M. (Ed.), 2: 368–400 (1985).

Rebois, R.V. et al., *Proc. Natl. Acad. Sci.* (*U.S.A.*) 78:2086–2089 (1981).

Kellokumpu, S. et al., *Endocrinol.* 116:707–714 (1985).

Ji, I. et al., *Proc. Natl. Acad. Sci.* (*U.S.A.*) 77:7167–7170 (1980).

Ji, I. et al., *Proc. Natl. Acad. Sci.* (*U.S.A.*) 78:5465–5469 (1981).

Hwang, J. et al., *J. Biol. Chem.* 259:1978–1985 (1984).

Hwang, J. et al., *Proc. Natl. Acad. Sci.* (*U.S.A.*) 81:4667–4671 (1984).

Dufau, M.L. et al., *J. Biol. Chem.* 250:4822–4824 (1975).

Kusuda, S. et al., *J. Biol. Chem.* 261(34):6161–6168 (1986).

Bruch, R.C. et al., *J. Biol. Chem.* 261:9450–9460 (1986).

Minegishi, T. et al., *J. Biol. Chem.* 262:17138–17143 (1987).

Wimalasena, J. et al., *J. Biol. Chem.* 260(19):10689–10697 (1985).

Keinanan, K.P. et al., *J. Biol. Chem.* 262:7920–7926 (1987).

Dattatreyamurty, B. et al., *J. Biol. Chem.* 258:3140–3158 (1983).

Shin, J. et al., *J. Biol. Chem.* 260(23): 12828–31 (1985).

Shin J. et al., *J. Biol. Chem.* 260:14020–25 (1985).

Smith, R.A. et al., *J. Biol. Chem.* 260(26):14297–14303 (1985).

Chan, J. et al., *Acta Endocrinol.* (*Suppl.*) 281: 166–172 (1987).

Auletta, J. and Flint, A., *Endocrinol. Rev.* 9(1):88–105 (1988).

L.O. Vodkin et al., *Cell* 34:1023–1031 (1983).

D.J. Schnell et al., *J. Biol. Chem.* 262(15):7220–7225 (1987).

D.J. Lipman et al., *Science* 227:1435–1441 (1985).

W.M. Fitch et al., *Proc. Natl. Acad. Sci. USA* 80:1382–1386 (1983).

J. Nathans et al., *Cell* 34:807–814 (1983).

Y. Masu et al., *Nature* 329:836–838 (1987).

R.A.F. Dixon et al., *Nature* 321:75–79(1986).

P.R. Schofield et al., *Nucl. Acids Res.* 15:3636 (1987).

D.B. Pritchett et al., *EMBO J.* 7(13):4135–4140 (1988).

N. Takahashi et al., *Proc. Natl. Sci. USA* 82:1906–1910 (1985).

T. Krusius et al., *Proc. Natl. Acad. Sci. USA* 83:7683–7687 (1986).

J. Lopez et al., *Proc. Natl. Acad. Sci. USA* 84:5615–5619 (1987).

C. Hashimoto et al., *Cell* 52:269–279 (1988).

T. Kataoka et al., *Cell* 43:493–505 (1985–Part 1).

R.J. Lefkowitz et al., *J. Biol. Chem.* 263(11):4993–4996 (1988).

M. Ascoli et al., *Endocrine Rev.* 10(1):27–43 (1989).

Jallal, B. et al. *Reprod. Nutr. Dev.* 28(4B):1177–1192 (1988).

N. Rosemblit et al., *Endocrinology* 123:2284–2289 (1988).

Nagayama et al., *Biochem. and Biophys. Res. Comm.,* 165(3): 1184–1190 (1989).

(List continued on next page.)

*Primary Examiner*—Lorraine Spector
(74) *Attorney, Agent, or Firm*—Deidre L. Conley

(57) ABSTRACT

The invention relates to the purification, and cloning of receptors for the luteinizing hormone, choriogonadotropin, follicle stimulating hormone, and thyroid stimulating hormone. The invention additionally concerns the uses for such molecules in the diagnosis and therapy of human conditions.

18 Claims, 13 Drawing Sheets

OTHER PUBLICATIONS

Parmentier et al., *Science,* 246:1620–1622 (1989).

Libert et al., *Biochem. and Biophys. Res. Comm.,* 165(3): 1250–1255 (1989).

Pierce et al., *Ann. Rev. Biochem.,* 50: 466–495 (1981).

K. Jacobs et al., Nature 313:806–810, Feb. 28, 1985.

J.E. Sims et al., Science 241:585, Jul. 29, 1988.

K. Yamasaki et al., Science 241:825, Aug. 12, 1988.

A. Aruffo et al., Proc. Nat. Acad. Sci. 84:8573–8577, Dec. 1987.

Sprengel, et al., "The Testicular Receptor for Follicle Stimulating Hormone: Structure and Functional Expression of Cloned cDNA" *Molecular Endocrinology* 4(4):525–530 (Apr. 1990).

Kotulla, et al., "Radioligand Receptor Assay (RRA) for Thyroid–Stimulating Hormone (TSH) Using Triton X–100 Solubilized Receptor Preparation" *Radioimmunoassays and Related Procedures in Medicine pp.* 297–305 (1982).

Branca et al., "The Subunit Structure of the Follitropin Receptor" *J. Biol. Chem.* 260(18):9988–9993 (Aug. 1985).

Yoshida et al., "Monoclonal Antibodies to the Thyrotropin Receptor Bind to a 56–kDa Subunit of the Thyrotropin Receptor and Show Heterogeneous Bioactivities" *J. Biol. Chem.* 23(31):16341–16347 (1988).

Kohn et al., "Autoimmune Thyroid Disease Studied with Monoclonal Antibodies to the Thyrotropin Receptor" *Monoclonal Antibodies* B.F. Haynes et al., Academic Press, pp. 230–253 (1983).

Y. Masu et al. Nature 329:836–838 Oct. 29, 1987.*

P.C. Roche et al. J. Biol. Chem. 264(8)4636–4641 Mar. 15, 1989.*

P. Walter et al. PNAS 82:7889–7893 Dec. 1985.*

K. Metsikko et al Endocrinology 109(5):1399–1403 1981.*

K.C. McFarland et al Science 245:494–499 Aug. 4, 1989.*

* cited by examiner

Fig. 1A.

```
-43 ATACTGGCTCAACCTCGGGAGCTCACACTCAGGCTGGCGGGCC

-26 Met Gly Arg Arg Val Pro Ala Leu Arg Gln Leu Leu Val Leu Ala Val Leu Leu Leu Lys Pro Ser Gln Leu Gln
  1 ATG GGG CGG CGA GTC CCA GCT CTG AGA CAG CTG CTG GTG CTG GCA GTG CTG CTG CTG AAG CCT TCA CAG CTG CAG

 -1 Ser Arg Glu Leu Ser Gly Ser Arg Cys Pro Glu Pro Cys Asp Cys Ala Pro Asp Gly Ala Leu Arg Cys Pro Gly
 76 TCC CGA GAG CTG TCA GGG TCG CGC TGC CCC GAG CCC TGC GAC TGC GCA CCG GAT GGC GCC CTG CGC TGT CCT GGC

 25 Pro Arg Ala Gly Leu Ala Arg Leu Ser Leu Thr Tyr Leu Pro Val Lys Val Ile Pro Ser Gln Ala Phe Arg Gly
151 CCT CGA GCC GGC CTC GCC AGA CTA TCT CTC ACC TAT CTC CCT GTC AAA GTA ATT CCA TCA CAA GCT TTC AGG GGA

 50 Leu Asn Glu Val Val Lys Ile Glu Ile Ser Gln Ser Asp Ser Leu Glu Arg Ile Glu Ala Asn Ala Phe Asp Asn
226 CTT AAT GAG GTC GTA AAA ATT GAA ATC TCT CAG AGT GAT TCC CTG GAA AGG ATA GAA GCT AAT GCC TTT GAC AAC

 75 Leu Leu Asn Leu Ser Glu Leu Leu Ile Gln Asn Thr Lys Asn Leu Leu Tyr Ile Glu Pro Gly Ala Phe Thr Asn
301 CTC CTC AAT TTG TCT GAA CTA CTG ATC CAG AAC ACC AAA AAC CTG CTA TAC ATT GAA CCT GGT GCT TTT ACA AAC

100 Leu Pro Arg Leu Lys Tyr Leu Ser Ile Cys Asn Thr Gly Ile Arg Thr Leu Pro Asp Val Thr Lys Ile Ser Ser
376 CTC CCT CGG TTA AAA TAC CTG AGC ATC TGT AAC ACA GGC ATC CGA ACC CTT CCA GAT GTT ACG AAG ATC TCC TCC

125 Ser Glu Phe Asn Phe Ile Leu Glu Ile Cys Asp Asn Leu His Ile Thr Thr Ile Pro Gly Asn Ala Phe Gln Gly
451 TCT GAA TTT AAT TTC ATT CTG GAA ATC TGT GAT AAC TTA CAC ATA ACC ACC ATA CCC GGG AAT GCT TTC CAA GGG

150 Met Asn Asn Glu Ser Val Thr Leu Lys Leu Tyr Gly Asn Gly Phe Glu Glu Val Gln Ser His Ala Phe Asn Gly
526 ATG AAT AAC GAG TCT GTC ACA CTA AAA CTG TAT GGA AAT GGA TTT GAA GAA GTA CAA AGC CAT GCA TTC AAT GGG

175 Thr Thr Leu Ile Ser Leu Glu Leu Lys Glu Asn Ile Tyr Leu Glu Lys Met His Ser Gly Ala Phe Gln Gly Ala
601 ACG ACT CTA ATC TCG CTG GAG CTA AAA GAA AAC ATC TAC CTG GAG AAG ATG CAC AGT GGA GCC TTC CAG GGG GCC

200 Thr Gly Pro Ser Ile Leu Asp Ile Ser Ser Thr Lys Leu Gln Ala Leu Pro Ser His Gly Leu Glu Ser Ile Gln
676 ACG GGG CCC AGC ATC CTG GAT ATT TCT TCC ACC AAA TTG CAG GCC CTG CCG AGC CAC GGG CTG GAG TCC ATT CAG

225 Thr Leu Ile Ala Leu Ser Ser Tyr Ser Leu Lys Thr Leu Pro Ser Lys Glu Lys Phe Thr Ser Leu Leu Val Ala
751 ACG CTC ATC GCC CTG TCT TCC TAC TCA CTG AAA ACA CTG CCC TCC AAA GAA AAA TTC ACG AGC CTC CTG GTC GCC

250 Thr Leu Thr Tyr Pro Ser His Cys Cys Ala Phe Arg Asn Leu Pro Lys Lys Glu Gln Asn Phe Ser Phe Ser Ile
826 ACG CTG ACC TAC CCC AGC CAC TGC TGC GCC TTC AGG AAT TTG CCG AAG AAA GAA CAG AAT TTT TCA TTT TCC ATT

275 Phe Glu Asn Phe Ser Lys Gln Cys Glu Ser Thr Val Arg Lys Ala Asp Asn Glu Thr Leu Tyr Ser Ala Ile Phe
901 TTT GAA AAC TTC TCC AAA CAA TGC GAA AGC ACA GTT AGA AAA GCA GAT AAC GAG ACG CTT TAT TCC GCC ATC TTT
```

Fig. 1B.

```
300  Glu Glu Asn Glu Leu Ser Gly Trp Asp Tyr Asp Tyr Gly Phe Cys Ser Pro Lys Thr Leu Gln Cys Ala Pro Glu
976  GAG GAG AAT GAA CTC AGT GGC TGG GAT TAT GAT TAT GGC TTC TGT TCA CCC AAG ACA CTC CAA TGT GCT CCA GAA

325  Pro Asp Ala Phe Asn Pro Cys Glu Asp Ile Met Gly Tyr Ala Phe Leu Arg Val Leu Ile Trp Leu Ile Asn Ile
1051 CCA GAT GCT TTC AAC CCC TGT GAA GAT ATT ATG GGC TAT GCC TTC CTT AGG GTC CTG ATT TGG CTG ATT AAT ATA

350  Leu Ala Ile Phe Gly Asn Leu Thr Val Leu Phe Val Leu Leu Thr Ser Arg Tyr Lys Leu Thr Val Pro Arg Phe
1126 CTA GCC ATC TTT GGC AAC CTG ACA GTC CTC TTT GTT CTC CTG ACC AGT CGT TAT AAA CTG ACA GTG CCC CGC TTC

375  Leu Met Cys Asn Leu Ser Phe Ala Asp Phe Cys Met Gly Leu Tyr Leu Leu Leu Ile Ala Ser Val Asp Ser Gln
1201 CTC ATG TGT AAT CTC TCC TTT GCA GAC TTT TGC ATG GGG CTC TAC CTG CTG CTC ATT GCC TCC GTG GAC TCC CAA

400  Thr Lys Gly Gln Tyr Tyr Asn His Ala Ile Asp Trp Gln Thr Gly Ser Gly Cys Gly Ala Ala Gly Phe Phe Thr
1276 ACA AAA GGC CAG TAC TAT AAC CAC GCC ATA GAC TGG CAG ACA GGG AGT GGC TGC GGT GCA GCT GGC TTC TTT ACT

425  Val Phe Ala Ser Glu Leu Ser Val Tyr Thr Leu Thr Val Ile Thr Leu Glu Arg Trp His Thr Ile Thr Tyr Ala
1351 GTG TTT GCC AGT GAA CTC TCT GTC TAC ACC CTG ACG GTT ATC ACC CTG GAA AGG TGG CAC ACC ATC ACC TAT GCT

450  Val Gln Leu Asp Gln Lys Leu Arg Leu Arg His Ala Ile Pro Ile Met Leu Gly Gly Trp Leu Phe Ser Thr Leu
1426 GTA CAG CTA GAC CAA AAG CTA AGA CTG AGG CAT GCC ATC CCA ATT ATG CTC GGA GGA TGG CTC TTT TCT ACG CTG

475  Ile Ala Thr Met Pro Leu Val Gly Ile Ser Asn Tyr Met Lys Val Ser Ile Cys Leu Pro Met Asp Val Glu Ser
1501 ATC GCC ACG ATG CCC CTT GTG GGT ATC AGC AAT TAC ATG AAG GTC AGC ATC TGC CTC CCC ATG GAT GTG GAA TCC

500  Thr Leu Ser Gln Val Tyr Ile Leu Ser Ile Leu Ile Leu Asn Val Val Ala Phe Val Val Ile Cys Ala Cys Tyr
1576 ACT CTG TCC CAA GTC TAC ATA TTA TCC ATC TTA ATC CTC AAC GTG GTG GCC TTC GTC GTC ATC TGT GCT TGC TAC

525  Ile Arg Ile Tyr Phe Ala Val Gln Asn Pro Glu Leu Thr Ala Pro Asn Lys Asp Thr Lys Ile Ala Lys Lys Met
1651 ATT AGG ATC TAC TTT GCA GTT CAA AAT CCA GAG CTG ACA GCT CCT AAC AAG GAC ACA AAA ATT GCT AAG AAG ATG
```

Fig. 1C.

```
 550 Ala Ile Leu Ile Phe Thr Asp Phe Thr Cys Met Ala Pro Ile Ser Phe Phe Ala Ile Ser Ala Ala Phe Lys Val
1726 GCC ATC CTC ATC TTC ACA GAC TTC ACG TGC ATG GCG CCC ATC TCT TTC TTT GCC ATC TCG GCT GCC TTC AAA GTG

 575 Pro Leu Ile Thr Val Thr Asn Ser Lys Ile Leu Leu Val Leu Phe Tyr Pro Val Asn Ser Cys Ala Asn Pro Phe
1801 CCC CTT ATC ACT GTC ACC AAC TCG AAA ATC TTA CTG GTC CTT TTT TAT CCT GTC AAT TCT TGT GCC AAT CCA TTT

 600 Leu Tyr Ala Ile Phe Thr Lys Ala Phe Gln Arg Asp Phe Leu Leu Leu Leu Ser Arg Phe Gly Cys Cys Lys Arg
1876 CTG TAT GCG ATC TTC ACG AAG GCG TTT CAG AGA GAT TTC CTT CTG CTG CTG AGC CGA TTC GGC TGC TGT AAA CGC

 625 Arg Ala Glu Leu Tyr Arg Arg Lys Glu Phe Ser Ala Tyr Thr Ser Asn Cys Lys Asn Gly Phe Pro Gly Ala Ser
1951 CGG GCG GAG CTT TAC AGA AGG AAG GAA TTT TCT GCA TAT ACT TCC AAC TGC AAA AAT GGC TTC CCA GGA GCA AGT

 650 Lys Pro Ser Gln Ala Thr Leu Lys Leu Ser Thr Val His Cys Gln Gln Pro Ile Pro Pro Arg Ala Leu Thr His
2026 AAG CCG TCC CAG GCT ACC CTG AAG TTG TCC ACA GTG CAC TGT CAA CAG CCC ATA CCA CCG AGA GCG TTA ACT CAC

2101 TAGCATTACAAAATTGTGCCTAAATATGTTTTTAAAAAGTGTTTAGAAAAATATTTATCCTTAGGCACTTCAGGAGAATTGTACCTGCTTCAGAGGAC
2201 GGCCTATAACACTTGGTCACATAAGTTTCAGGAAGGTTTAGAAATTTTTATAGTAATTTAGGCATAATAATTTTTTGTTGAATCTAATACTAAGGAAATC
2301 TAAGTTGTCATTTTTCACGTCTCTGACATTTTTCATTTCAATCTTGTGATTTACATTGTAATCTCCAAATATATTACTTCATAGCAGATTGAAAATTTAA
2401 ACTGGTCTTTGTCCTCAGATAGTTTGATAAATATATTCAAGAGATGCACTGTGCAGTGTGACTGCTAGCCTTGCATGGTAAATAGAAGTTTCTTAGCCAT
2501 ATTCCAAGTGCTTCACATGTCACACTAGGAGGCACAGATGCAAACTGTTTACATCAGTGAATTCTATTAGCCAGCTCTATTCTAGAGACTTCTATTTCCC
2601 ATTGACACTCTGCTTAACTTTCCATCTGAAGGCACATGCTGCATATTTGTTTGGCTTACAGATCATGAGTACCTCATGGCCAGGAGCCCATCTCAGCCCA
2701 TCTTGTTCCTCGTCTATCTCAGGATCTTGGAAATGCTACACAGCAAGCATGCCTAGCCAGTTAAACTCCCTAAATCTACACAGGAAAATATTTCTACCAC
2801 CTTAGCATATTGTTTTCGATGATTACATGCTTTCTGTATTTTGCCCTCCTCCTAGTATC
```

```
lhrk   KELSGSRKPEPNDFAPDGALXXPGP          lhrf  (M)X(S)GAFQGATGPSILDPV
                                                    (E)            (I)
lhrr   (M)XXESVTLKLYGNCFEEVQ
                                          lhrc  (M)(D)YA(G)LXVLI(G)LINILDXF
lhr28  (K)NLLYIEPGSF                             (G)  (F)      (F)
                                                   (A)
lhr26  (K)XYGNXFEXVQ                               (N)
```

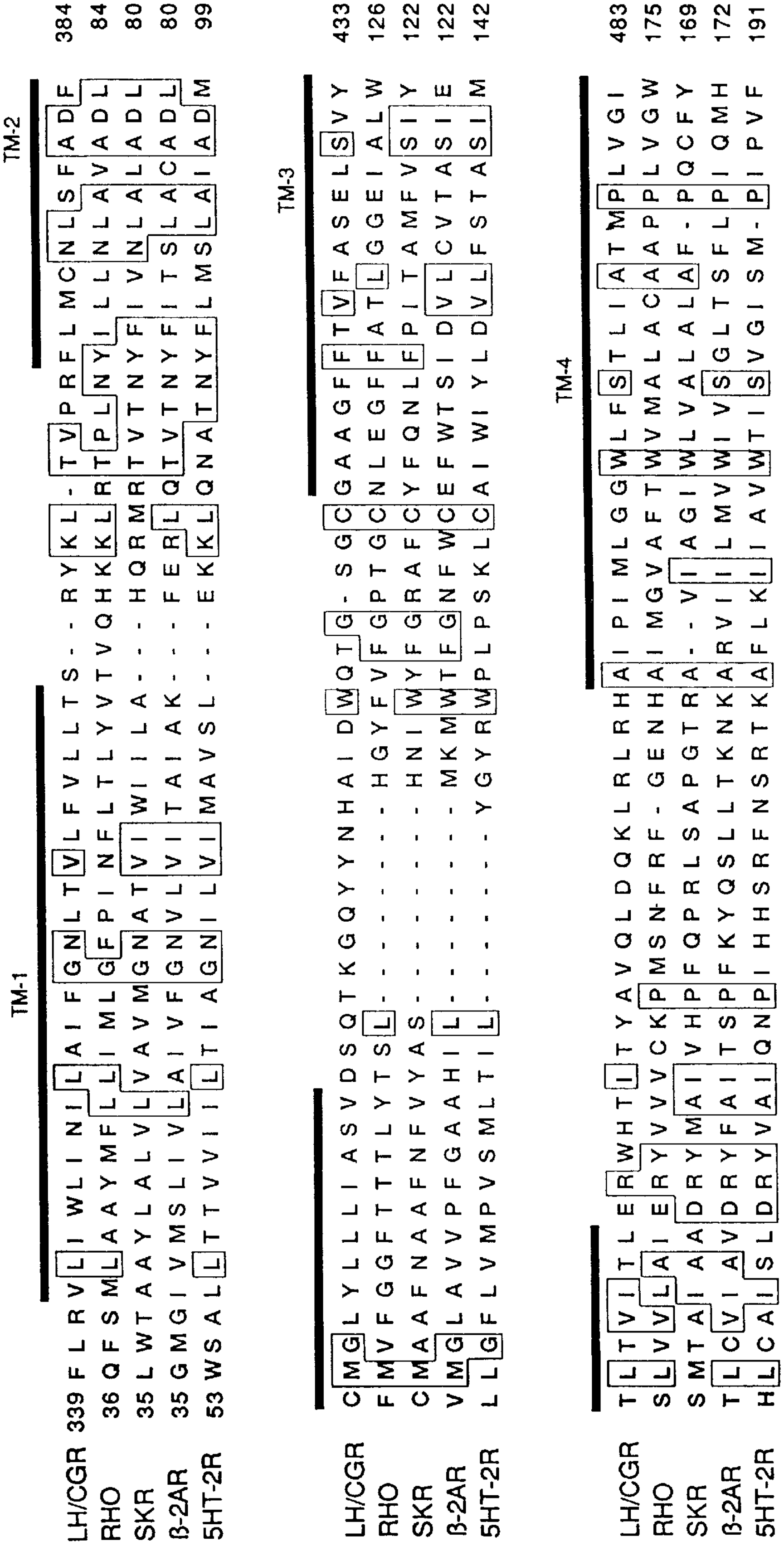

Fig. 2A.

```
                                TM-1                                                                                TM-2
LH/CGR 339  F L R V L W L I N I L A I F G N L T V L F V L L T S - - R Y K L - T V P R F L M C N L S F A D F  384
RHO     36  Q F S M L A A Y M F L L I M L G F P I N F L T L Y V T V Q H K K L R T P L N Y I L L N L A V A D L   84
SKR     35  L W T A A Y L A L V L V A V M G N A T V I W I I L A - - - H Q R M R T V T N Y F I V N L A L A D L   80
β-2AR   35  G M G I V M S L I V L A I V F G N V L V I T A I A K - - F E R L Q T V T N Y F I T S L A C A D L    80
5HT-2R  53  W S A L L T T V V I I L T I A G N I L V I M A V S L - - - - E K K L Q N A T N Y F L M S L A I A D M  99

                                TM-3
LH/CGR      C M G L Y L L L I A S V D S Q T K G Q Y Y N H A I D W Q T G - S G C G A A G F F T V F A S E L S V Y  433
RHO         F M V F G G F T T T L Y T S L - - - - - - - - H G Y F V F G P T G C N L E G F F A T L G G E I A L W  126
SKR         C M A A F N A A F N F V Y A S - - - - - - - - H N I W Y F G R A F C Y F Q N L F P I T A M F V S I Y  122
β-2AR       V M G L A V V P F G A A H I L - - - - - - - - M K M W T F G N F W C E F W T S I D V L C V T A S I E  122
5HT-2R      L L G F L V M P V S M L T I L - - - - - - - Y G Y R W P L P S K L C A I W I Y L D V L F S T A S I M  142

                                TM-4
LH/CGR      T L T V I T L E R W H T I T Y A V Q L D Q K L R L R H A I P I M L G G W L F S T L I A T M P L V G I  483
RHO         S L V V L A I E R Y V V V C K P M S N F R F - G E N H A I M G V A F T W V M A L A C A A P P L V G W  175
SKR         S M T A I A A D R Y M A I V H P F Q P R L S A P G T R A - - V I A G I W L V A L A L A F - P Q C F Y  169
β-2AR       T L C V I A V D R Y F A I T S P F K Y Q S L L T K N K A R V I I L M V W I V S G L T S F L P I - Q M H  172
5HT-2R      H L C A I S L D R Y V A I Q N P I H H S R F N S R T K A F L K I I A V W T I S V G I S M - P I P V F  191
```

Fig. 6A.

-71 AGGAGCCTGG GGAATCTGTG GAAGTTTTCG CGCTGATGCA GAAAGAAAGT CGGTGAATGG

-10 ATAAATAAGG ATG GCC TTG CTC CTG GTC TCC TTG CTG GCA TTC TTG GGC ACG GGA TCT GGA
-17 Met Ala Leu Leu Leu Val Ser Leu Leu Ala Phe Leu Gly Thr Gly Ser Gly

51 TGT CAT CAC TGG CTG TGT CAT TGC TCT AAT AGG GTC TTT CTC TGC CAA GAC AGC AAG GTG
1 Cys His His Trp Leu Cys His Cys Ser Asn Arg Val Phe Leu Cys Gln Asp Ser Lys Val

111 ACA GAG ATT CCG ACC GAC CTC CCC CGG AAC GCC ATT GAA CTG AGG TTT GTG CTC ACC AAG
21 Thr Glu Ile Pro Thr Asp Leu Pro Arg Asn Ala Ile Glu Leu Arg Phe Val Leu Thr Lys

171 CTT CGA GTC ATC CCG AAA GGA TCA TTT GCT GGA TTT GGA GAC CTG GAG AAA ATA GAG ATC
41 Leu Arg Val Ile Pro Lys Gly Ser Phe Ala Gly Phe Gly Asp Leu Glu Lys Ile Glu Ile

231 TCT CAG AAT GAT GTC TTG GAA GTA ATA GAG GCA GAT GTG TTC TCC AAC CTA CCC AAG TTG
61 Ser Gln Asn Asp Val Leu Glu Val Ile Glu Ala Asp Val Phe Ser Asn Leu Pro Lys Leu

291 CAT GAA ATT AGG ATT GAA AAG GCC AAC AAT CTT CTG TAC ATC AAC CCG GAG GCC TTC CAG
81 His Glu Ile Arg Ile Glu Lys Ala Asn Asn Leu Leu Tyr Ile Asn Pro Glu Ala Phe Gln

351 AAT CTC CCC AGT CTC AGA TAT CTG TTA ATA TCC AAC ACA GGC ATT AAG CAC TTG CCA GCT
101 Asn Leu Pro Ser Leu Arg Tyr Leu Leu Ile Ser Asn Thr Gly Ile Lys His Leu Pro Ala

411 GTT CAC AAG ATC CAG TCT CTC CAA AAG GTT CTA CTA GAC ATT CAA GAT AAC ATA AAC ATC
121 Val His Lys Ile Gln Ser Leu Gln Lys Val Leu Leu Asp Ile Gln Asp Asn Ile Asn Ile

471 CAC ATC GTT GCC AGG AAC TCC TTC ATG GGA CTG AGT TTT GAA AGT GTG ATT TTA TGG CTG
141 His Ile Val Ala Arg Asn Ser Phe Met Gly Leu Ser Phe Glu Ser Val Ile Leu Trp Leu

531 AGT AAG AAT GGG ATT GAA GAA ATA CAC AAC TGT GCA TTC AAC GGA ACT CAG CTA GAT GAA
161 Ser Lys Asn Gly Ile Glu Glu Ile His Asn Cys Ala Phe Asn Gly Thr Gln Leu Asp Glu

591 CTG AAT CTA AGC GAT AAC AAT AAT TTG GAA GAA TTG CCT AAT GAC GTT TTC CAG GGA GCC
181 Leu Asn Leu Ser Asp Asn Asn Asn Leu Glu Glu Leu Pro Asn Asp Val Phe Gln Gly Ala

651 TCT GGG CCA GTC ATT TTA GAT ATC TCA AGG ACA AAG GTC CAT TCC TTA CCA AAC CAT GGC
201 Ser Gly Pro Val Ile Leu Asp Ile Ser Arg Thr Lys Val His Ser Leu Pro Asn His Gly

711 TTA GAA AAT CTG AAG AAG CTG AGG GCC AGG TCA ACA TAC CGC TTG AAA AAG CTC CCT AAT
221 Leu Glu Asn Leu Lys Lys Leu Arg Ala Arg Ser Thr Tyr Arg Leu Lys Lys Leu Pro Asn

771 CTG GAC AAG TTT GTC ACC CTC ATG GAG GCC AGC CTC ACC TAC CCC AGC CAC TGC TGT GCT
241 Leu Asp Lys Phe Val Thr Leu Met Glu Ala Ser Leu Thr Tyr Pro Ser His Cys Cys Ala

831 TTT GCA AAC TTG AAG CGG CAA ATC TCT GAA CTT CAT CCA ATT TGC AAC AAG TCT ATT TTA
261 Phe Ala Asn Leu Lys Arg Gln Ile Ser Glu Leu His Pro Ile Cys Asn Lys Ser Ile Leu

891 AGG CAA GAT ATT GAT GAT ATG ACT CAA ATT GGG GAT CAG AGA GTC TCT CTG ATA GAT GAT
281 Arg Gln Asp Ile Asp Asp Met Thr Gln Ile Gly Asp Gln Arg Val Ser Leu Ile Asp Asp

951 GAA CCC AGT TAT GGA AAA GGA TCT GAC ATG ATG TAC AAT GAA TTT GAT TAT GAC TTA TGT
301 Glu Pro Ser Tyr Gly Lys Gly Ser Asp Met Met Tyr Asn Glu Phe Asp Tyr Asp Leu Cys

1011 AAT GAA GTT GTT GAT GTG ACC TGC TCA CCA AAG CCA GAT GCA TTT AAT CCA TGT GAA GAT
321 Asn Glu Val Val Asp Val Thr Cys Ser Pro Lys Pro Asp Ala Phe Asn Pro Cys Glu Asp

Fig. 6B.

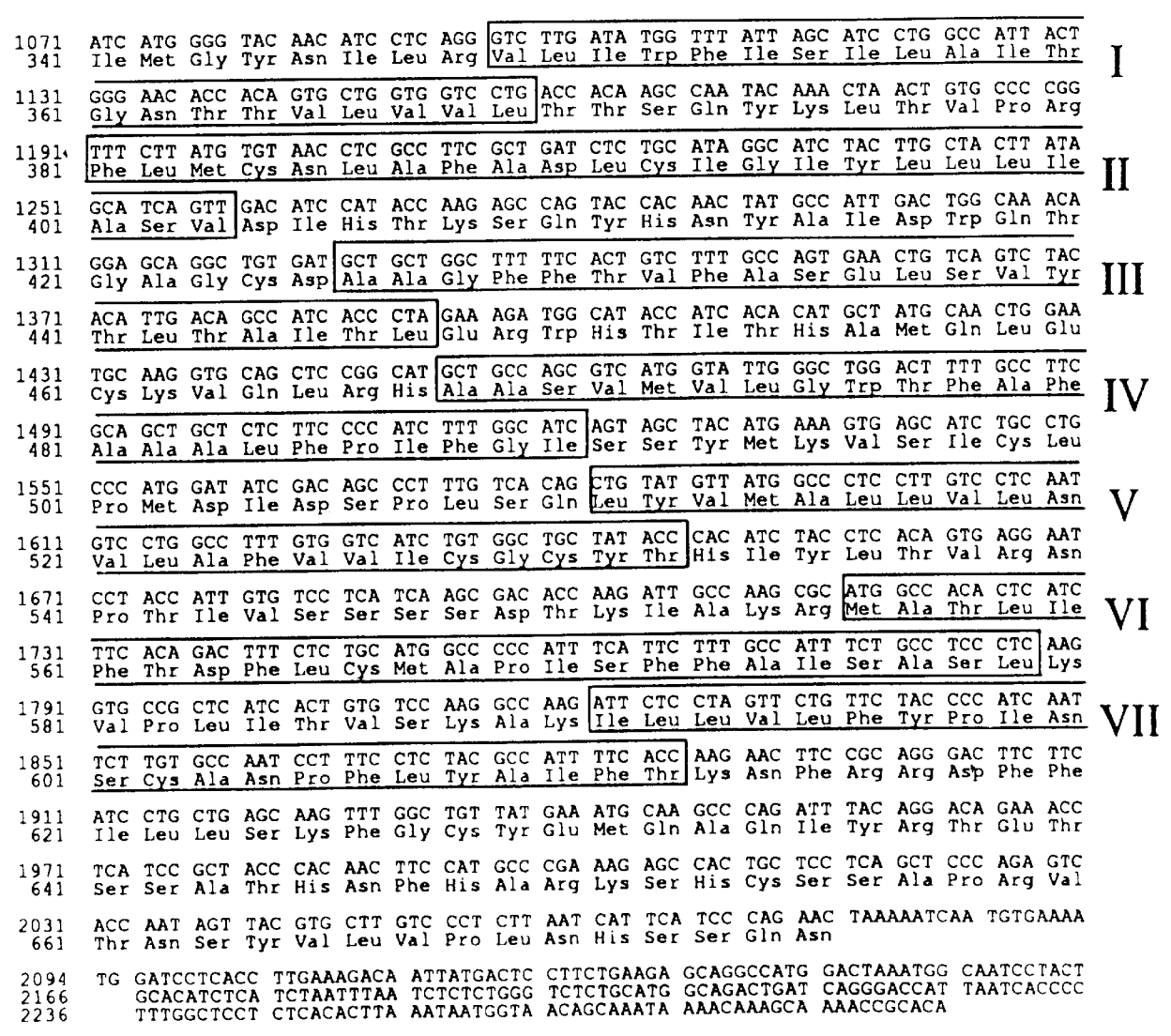

```
1071 ATC ATG GGG TAC AAC ATC CTC AGG GTC TTG ATA TGG TTT ATT AGC ATC CTG GCC ATT ACT
 341 Ile Met Gly Tyr Asn Ile Leu Arg Val Leu Ile Trp Phe Ile Ser Ile Leu Ala Ile Thr   I

1131 GGG AAC ACC ACA GTG CTG GTG GTC CTG ACC ACA AGC CAA TAC AAA CTA ACT GTG CCC CGG
 361 Gly Asn Thr Thr Val Leu Val Val Leu Thr Thr Ser Gln Tyr Lys Leu Thr Val Pro Arg

1191 TTT CTT ATG TGT AAC CTC GCC TTC GCT GAT CTC TGC ATA GGC ATC TAC TTG CTA CTT ATA
 381 Phe Leu Met Cys Asn Leu Ala Phe Ala Asp Leu Cys Ile Gly Ile Tyr Leu Leu Leu Ile   II

1251 GCA TCA GTT GAC ATC CAT ACC AAG AGC CAG TAC CAC AAC TAT GCC ATT GAC TGG CAA ACA
 401 Ala Ser Val Asp Ile His Thr Lys Ser Gln Tyr His Asn Tyr Ala Ile Asp Trp Gln Thr

1311 GGA GCA GGC TGT GAT GCT GCT GGC TTT TTC ACT GTC TTT GCC AGT GAA CTG TCA GTC TAC
 421 Gly Ala Gly Cys Asp Ala Ala Gly Phe Phe Thr Val Phe Ala Ser Glu Leu Ser Val Tyr   III

1371 ACA TTG ACA GCC ATC ACC CTA GAA AGA TGG CAT ACC ATC ACA CAT GCT ATG CAA CTG GAA
 441 Thr Leu Thr Ala Ile Thr Leu Glu Arg Trp His Thr Ile Thr His Ala Met Gln Leu Glu

1431 TGC AAG GTG CAG CTC CGG CAT GCT GCC AGC GTC ATG GTA TTG GGC TGG ACT TTT GCC TTC
 461 Cys Lys Val Gln Leu Arg His Ala Ala Ser Val Met Val Leu Gly Trp Thr Phe Ala Phe   IV

1491 GCA GCT GCT CTC TTC CCC ATC TTT GGC ATC AGT AGC TAC ATG AAA GTG AGC ATC TGC CTG
 481 Ala Ala Ala Leu Phe Pro Ile Phe Gly Ile Ser Ser Tyr Met Lys Val Ser Ile Cys Leu

1551 CCC ATG GAT ATC GAC AGC CCT TTG TCA CAG CTG TAT GTT ATG GCC CTC CTT GTC CTC AAT
 501 Pro Met Asp Ile Asp Ser Pro Leu Ser Gln Leu Tyr Val Met Ala Leu Leu Val Leu Asn   V

1611 GTC CTG GCC TTT GTG GTC ATC TGT GGC TGC TAT ACC CAC ATC TAC CTC ACA GTG AGG AAT
 521 Val Leu Ala Phe Val Val Ile Cys Gly Cys Tyr Thr His Ile Tyr Leu Thr Val Arg Asn

1671 CCT ACC ATT GTG TCC TCA TCA AGC GAC ACC AAG ATT GCC AAG CGC ATG GCC ACA CTC ATC
 541 Pro Thr Ile Val Ser Ser Ser Ser Asp Thr Lys Ile Ala Lys Arg Met Ala Thr Leu Ile   VI

1731 TTC ACA GAC TTT CTC TGC ATG GCC CCC ATT TCA TTC TTT GCC ATT TCT GCC TCC CTC AAG
 561 Phe Thr Asp Phe Leu Cys Met Ala Pro Ile Ser Phe Phe Ala Ile Ser Ala Ser Leu Lys

1791 GTG CCG CTC ATC ACT GTG TCC AAG GCC AAG ATT CTC CTA GTT CTG TTC TAC CCC ATC AAT
 581 Val Pro Leu Ile Thr Val Ser Lys Ala Lys Ile Leu Leu Val Leu Phe Tyr Pro Ile Asn   VII

1851 TCT TGT GCC AAT CCT TTC CTC TAC GCC ATT TTC ACC AAG AAC TTC CGC AGG GAC TTC TTC
 601 Ser Cys Ala Asn Pro Phe Leu Tyr Ala Ile Phe Thr Lys Asn Phe Arg Arg Asp Phe Phe

1911 ATC CTG CTG AGC AAG TTT GGC TGT TAT GAA ATG CAA GCC CAG ATT TAC AGG ACA GAA ACC
 621 Ile Leu Leu Ser Lys Phe Gly Cys Tyr Glu Met Gln Ala Gln Ile Tyr Arg Thr Glu Thr

1971 TCA TCC GCT ACC CAC AAC TTC CAT GCC CGA AAG AGC CAC TGC TCC TCA GCT CCC AGA GTC
 641 Ser Ser Ala Thr His Asn Phe His Ala Arg Lys Ser His Cys Ser Ser Ala Pro Arg Val

2031 ACC AAT AGT TAC GTG CTT GTC CCT CTT AAT CAT TCA TCC CAG AAC TAAAAATCAA TGTGAAAA
 661 Thr Asn Ser Tyr Val Leu Val Pro Leu Asn His Ser Ser Gln Asn

2094 TG GATCCTCACC TTGAAAGACA ATTATGACTC CTTCTGAAGA GCAGGCCATG GACTAAATGG CAATCCTACT
2166    GCACATCTCA TCTAATTTAA TCTCTCTGGG TCTCTGCATG GCAGACTGAT CAGGGACCAT TAATCACCCC
2236    TTTGGCTCCT CTCACACTTA AATAATGGTA ACAGCAAATA AAACAAAGCA AAACCGCACA
```

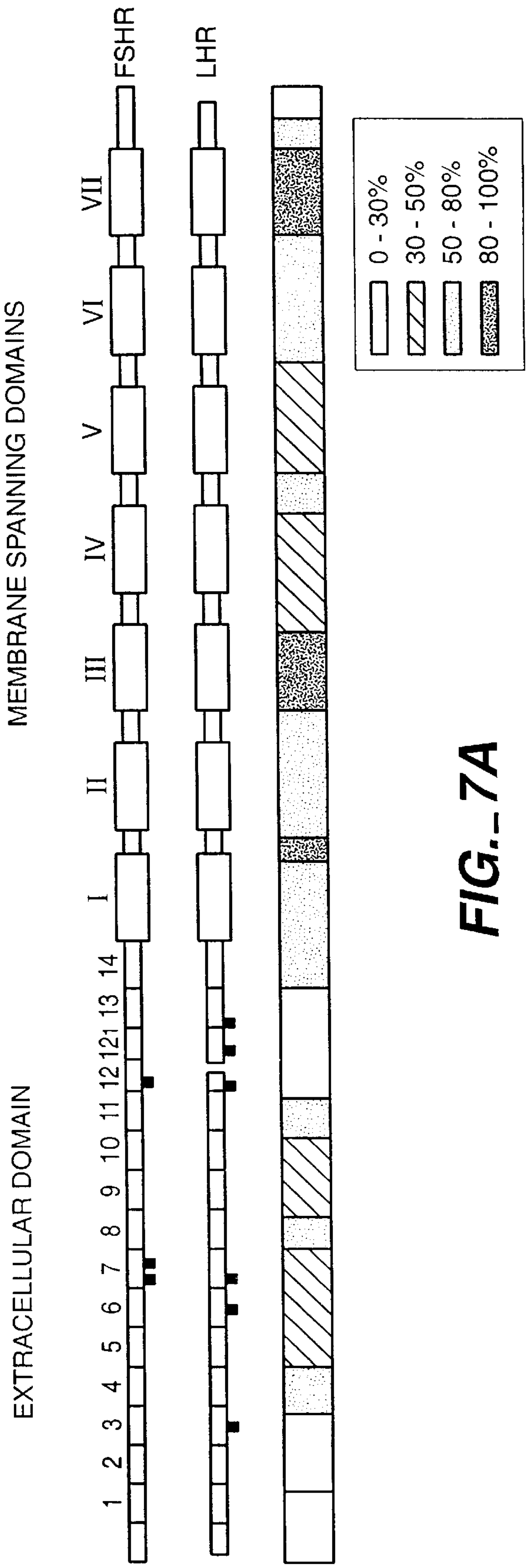
FIG._7A

```
  1 RELSGSR PE.P D APDGA R PGPRAGLAR......... SLTYLPVK
  1       CHHWLCHCSNRVFL.CQDSKVTEIPTDLPRNAIELRFVLTKLR
        ●     ● ●      ●

 41    SQA R LNEVV       S S   R    NA D   LN S LL QNTK
 43 VIPKGSFAGFGDLEKIEISQNDVLEVIEADVFSNLPKLHEIRIEKANNLL

 91   E G   T   R K  S C    RT   D T   S SEFNFI E C  LH T
 91 YINPEAFQNLPSLRYLLISNTGIKHLPAVHKIQSLQ.KVLLDIQDNINIH

141 TIPG A Q MNN   T K YG  F  VQSH     T IS E KE IY  K
142 IVARNSFMGLSFESVILWLSKNGIEEIHNCAFNGTQLDELNLSDNNNLEE

191 MHSGA     T  S     S  LQA  S     SIQT I L S S  T  SK
192 LPNDVFQGASGPVILDISRTKVHSLPNHGLENLKKLRARSTYRLKKLPNL

241 E  TS LV  T           R   PKKEQNF....SF   ....FENFSKQC
242 DKFVTLMEASLTYPSHCCAFANLKRQISELHPICNKSILRQDIDDMTQIG
                    ●●

283 EST RKA N TL SAIFEENELSGWDY  GF S.PKTLQ A E
292 DQRVSLIDDEPSYG...KGSDMMYNEFDYDLCNEVVDVTCSPKPDAFNPC
                                    ●      ●        ●

                            TM I
332       AF      L N    F  L    F  L  R            S
339 EDIMGYNILRVLIWFISILAITGNTTVLVVLTTSQYKLTVPRFLMCNLAF

         TM II                                TM III
382   F M L          SQ  G  Y  H      S  G
389 ADLCIGIYLLLIASVDIHTKSQYHNYAIDWQTGAGCDAAGFFTVEASELS
                                        ^

                                          TM IV
432      V             Y V  DQ LR    IPI LG  L STLI TM LV
439 VYTLTAITLERWHTITHAMQLECKVQLRHAASVMVLGWTFAFAAALEPIF

                                      TM V
482    N         VE T     V ILSI I  V      A  IR  FA
489 GISSYMKVSICLPMDIDSPLSQLYVMALLVLNVLAFVVICGCYTHIYLTV
              ^

                                 TM VI
532 Q  ELTAPNK     K I    T          AF         TN
539 RNPTIVSSSSDTKIAKRMATLIFTDFLCMAPISFFAISASLKVPLITVSK

             TM VII
582 S       V           A Q   LL   R   CKRR EL  .
589 AKILLVLFYPINSCANPFLYAIFTKNFRRDFFILLSKFGCYEMQAQIYRT

631 ........... EF..  YTSNCKNGFPGASKP  ATLKLSTVHCQQPI
639 ETSSATHNFHARKSHCSSAPRVTNSYVLVPLNHSSQN.............

693 PPRALTH     rat LH/CG receptor
639 .......     rat  FSH  receptor
```

*FIG._7B*

LUTEINIZING HORMONE/ CHORIOGONADOTROPIN (LH/CG) RECEPTOR

CROSS REFERENCES

This application is a continuation of U.S. application Ser. No. 07/781,153 filed Oct. 31, 1991 (abandoned), which was the U.S. National Stage of PCT/US90/02488 filed May, 4, 1990, which application is a continuation-in-part of U.S. application Ser. No. 07/347,683 filed May 5, 1989 (abandoned), which applications are incorporated herein by reference and to which applications priority is claimed under 35 USC §120.

FIELD OF THE INVENTION

The invention relates to the purification, and cloning of the cellular receptor molecules for luteinizing hormone, choriogonado-tropin, follicle stimulating hormone, and thyroid stimulating hormone. The invention further relates to the uses for the purified hormone receptor molecules.

BACKGROUND OF THE INVENTION

I Hormones of the Anterior Pituitary

The anterior pituitary (adenohypophysis) is the source of several major glycoprotein hormones including luteinizing hormone (lutropin, or "LH"), choriogonadotropin (or "CG"), follicle stimulating hormone (follitropin or "FSH"), and thyroid stimulating hormone (thyrotropin or "TSH"). The hormones of the anterior pituitary are reviewed by Norman, A. W. et al. (In: *Hormones*, Acad. Press, New York., (1987)). The hormones are highly conserved evolutionarily; the primary amino acid sequences of the LH, CG, and TSH hormones of rat and other animals are highly similar to those of humans (Strickland, T. W. et al., In: *Luteinizing Hormone Action and Receptors*, Ascoli, M. (Ed.), CRC Press, Boca Raton, Fla. (1985)).

Luteinizing hormone, follicle stimulating hormone, human choriogonadotropin (hCG) and thyroid stimulating hormone share many common characteristics, and have been considered to be members of a family of glycoprotein hormones. All contain approximately 200–250 amino acid residues, and are composed of a common $\alpha$ subunit (having a molecular weight of approximately 13–15 kDa) and a distinctive $\beta$ subunit (having a molecular weight of approximately 13–22 kDa). The $\alpha$ subunits of LH, FSH, and TSH are identical; the $\alpha$ subunit of CG has been reported to differ slightly from the others (Ganong, W. F. *Review of Medical Physiology,* 9th Ed., Lange Medical Pub., Los Altos, Calif., (1979)).

The hormones mediate their biological actions by binding to receptor molecules present on the surfaces of target cells. Interaction of the $\alpha$ subunit with the hormone specific $\beta$ subunits of the hormones are responsible for confering the binding specificity of the hormones. The hormones act by activating cellular adenylate cyclase to increase intracellular cAMP levels (de la Llose-Hermier et al., *Acta Endocrinol,* 11:399–406 (1988)).

Luteinizing hormone and follicle stimulating hormone are both gonadotropins (Ascoli, M. (Ed.) *Luteinizing Hormone Action and Receptors*, CRC Press, Boca Raton, Fla., (1985)). LH binds to a receptor expressed on the surfaces of Leydig (interstitial) cells (Ascoli, M., In: *The Receptors*, (Conn, P. M. (Ed.), vol. 2, pp 368 (1985)). In men, LH binding causes the Leydig cells to increase their synthesis of testosterone. In women, such binding causes the granulosa, theca, interstitial, and luteal cells to increase the concentrations of androgens, estrogens, and progestins, especially progesterone.

Follicle stimulating hormone regulates the development of gametes. In men, FSH binds to a receptor present on the surface of the Sertoli cells, and assists in the developmental process which results in the production of mature spermatozoa. In women, the hormone binds to receptors on the surface of the granulosa cells of the ovary. It is believed to act in concert with estrogen and LH to stimulate follicle development. Reflecting its role in oocyte development, FSH is maximally expressed at the time of ovulation in the female reproductive cycle. For this reason, an assay for FSH can be used to detect and predict the occurrence of ovulation. FSH also acts to stimulate the expression of LH/CG receptors by granulosa cells.

Choriogonadotropin is a gonadotropin produced by the trophoblastic cells of the placenta. It acts to stimulate the growth and development of the corpus luteum in the ovary by stimulating the production of progesterone. Choriogonadotropin has a role in preparing the maternal metabolism for the pregnancy. CG expression increases rapidly after conception, and as such, can be used as an assay for pregnancy. Administration of either LH, FSH, or CG can induce ovulation in a female. The hormones may be used in the treatment of infertility.

The principal action of TSH is to stimulate thyroid secretion and growth. TSH binds to a receptor molecule which is expressed on the surface of thyroid cells. Monoclonal antibodies have been developed which are able to bind to the TSH receptor. Individuals suffering from Graves Disease produce autoantibodies which are capable of binding to the TSH receptor molecule. In contrast to the anti-TSH receptor monoclonal antibodies, binding by the autoantibodies mimics TSH, and therefore acts as a stimulator of thyroid activity (Furmaniak, J. et al., *Acta Endocrinol*, (*Suppl*) 281: 157–165 (1987)). The clinical symptoms of Graves Disease are marked by hyperthyroidism.

II Receptors of the Glycoprotein Hormones of the Anterior Pituitary (including hCG)

Studies have revealed that luteinizing hormone and choriogonadotropin share the same cellular receptor molecule (Ascoli, M. (Ed.) *Luteinizing Hormone Action and Receptors,* CRC Press, Boca Raton, Fla., (1985)). The use of chemical and photoaffinity cross-linking agents has enabled researchers to study the hormone binding site of the receptor (Ji, I. et al., *Proc. Natl. Acad. Sci.* (*U.S.A.*) 77:7167 (1980); Rebois, R. V. et al., *Proc. Natl. Acad. Sci.* (*U.S.A.*) 78:2086 (1981); Metsikko, M. K. et al., *Biochem J.* 208:309 (1982)). These studies have not, however, led to the elucidation of the structure of the receptor molecule. On the basis of such studies, several research groups have concluded that the receptor is a single polypeptide of approximately 70–105 kDa (Ascoli, M. et al., *J. Biol. Chem.* 261:3807 (1986); Rebois, R. V. et al., *Proc. Natl. Acad. Sci.* (*U.S.A.*) 78:2086 (1981); Kellokumpu, S. et al., *Endocrinol.* 116:707 (1985)). Similar studies, however, have led other researchers to conclude that the receptor was composed of several polypeptide subunits (Ji, I. et al., *Proc. Natl. Acad. Sci.* (*U.S.A.*) 77:7167 (1980); Ji, I. et al., *Proc. Nat. Acad. Sci.* (*U.S.A.*) 78:5465 (1981); Hwang, J. et al., *J. Biol. Chem.* 259:1978 (1984); Hwang, J. et al., *Proc. Natl. Acad. Sci.* (*U.S.A.*) 81:4667 (1984)). The disparate conclusions reached by these researchers have not been reconcilable.

The purification of the LH/CG receptor has been reported by several research groups (Dufau, M. L. et al., *J. Biol. Chem.* 250:4822 (1975); Kusuda, S. et al., *J. Biol. Chem.* 261:6161 (1986); Bruch, R. C. et al., *J. Biol. Chem.* 261:9450 (1986); Minegishi, T. et al., *J. Biol. Chem.* 262:17138 (1987); Wimalasena, J. et al., *J. Biol. Chem.*

260:10689 (1985); Keinanan, K. P. et al., *J. Biol. Chem.* 262:7920 (1987); Dattatreyamurty, B. et al., *J. Biol. Chem.* 258:3140 (1983)). The reported characteristics of the purified protein have, however, been so disparate that they have failed to permit a conclusion to be reached regarding the nature of the LH/RH receptor, or the number of subunits which it contains.

The FSH receptor has also not been well characterized. Using photoaffinity techniques, researchers have concluded that the FSH receptor is composed of three subunits (Shih, J. et al., *J. Biol. Chem.* 260:12822 (1985); Shih, J. et al., *J. Biol. Chem.* 260:12828 (1985); Shih, J. et al., *J. Biol. Chem.* 260:14020 (1985); Smith, R. A. et al., *J. Biol. Chem.* 260:14297 (1985); Smith, R. A. et al., *J. Biol. Chem.* 260:14297 (1985)). The TSH receptor has been reported to be an approximately 300 kDa protein, which is cleaved to form at least two 70 kDa proteins. The 70 kDa proteins can themselves be cleaved to form a 50 kDa and a 20 kDa protein (Chan, J. et al., *Acta Endocrinol.* (*Suppl.*) 281:166 (1987); Smith, R. A. et al., *Endocrinol. Rev.* 9:88 (1988)).

In summary, the glycoprotein hormones of the anterior pituitary, as well as choriogonadotropin made by the placenta, have been found to mediate their biological effects via an interaction with a cellular receptor molecule present on the surface of target cells. Despite vigorous efforts, the nature and structure of these receptor molecules has not been resolved.

The hormone receptor molecules may be used both for diagnostic and therapeutic purposes. The receptor molecules may also be used to design synthetic hormones or hormone antagonists. Thus, an ability to produce purified hormone receptor molecules would be highly desirable.

SUMMARY OF THE INVENTION

The invention relates to the purification, and cloning, of receptors for luteinizing hormone, choriogonadotropin, follicle stimulating hormone, and thyroid stimulating hormone. The invention additionally concerns the uses for such molecules in the diagnosis and therapy for human conditions.

In detail, the invention concerns a pharmaceutical composition containing a therapeutically effective amount of hormone receptor molecule, wherein the hormone receptor molecule is selected from the group consisting of the LH/CG receptor, the FSH receptor, and the TSH receptor.

The invention also concerns a recombinant DNA molecule having a gene sequence encoding a hormone receptor molecule, wherein the hormone receptor molecule is selected from the group consisting of the LH/CG receptor, the FSH receptor, and the TSH receptor.

The invention also concerns a method of treating a condition in an animal or a human which comprises administering to the human a therapeutically effective amount of a pharmaceutical composition containing a therapeutically effective amount of a hormone receptor molecule, wherein the hormone receptor molecule is selected from the group consisting of the LH/CG receptor, the FSH receptor, and the TSH receptor.

The invention also concerns a method of detecting a hormone in a sample suspected of containing the hormone which comprises:

(a) incubating the sample in the presence of a receptor for the hormone, under conditions sufficient to permit the receptor to bind to, and undergo detectable change by, any of the hormone present in the sample; and (b) detecting the hormone by determining whether any of the receptor has become bound to, and undergone detectable change by a hormone molecule;

wherein the hormone is selected from the group consisting of: luteinizing hormone, choriogonadotropin, follicle stimulating hormone, and thyroid stimulating hormone.

The invention also concerns a method for producing a hormone receptor which comprises:

(a) constructing a vector that includes a gene sequence which encodes the hormone receptor;

(b) transforming a host cell with the vector;

(c) culturing the transformed cell in a culture medium under conditions sufficient for the cell to express the gene sequence; and (d) recovering the expressed hormone receptor;

wherein the hormone receptor is selected from the group consisting of the LH/CG receptor, the FSH receptor, and the TSH receptor.

The invention also concerns an antibody or antigen-binding fragment thereof, substantially free of natural contaminants, which is capable of binding to a hormone receptor selected from the group consisting of the LH/CG receptor, the FSH receptor, and the TSH receptor.

BRIEF DESCRIPTION OF THE FIGURES

FIG. 1A, FIG. 1B and FIG. 1C show the cDNA and predicted amino acid sequence of the rat ovarian LH/CG-R. In the figure, chemically determined peptide sequences are indicated by bars atop corresponding sequences, with residues differing from those predicted indicated by white bars. Amino acid numbering begins at the N-terminal sequence found for the mature intact receptor, with negative numbers for the encoded signal sequence. Putative extracellular N-linked glycosylation sites are marked by inverted triangles, and the proposed membrane-spanning hydrophobic sequences are enclosed in boxes. Overlined residues show location of similarity to soybean lectin (L. O. Vodkin et al., *Cell* 34:1023 (1983); D. J. Schnell et al., *J. Biol. Chem.* 262:7220 (1987) (Diflorus)).

FIG. 2A and FIG. 2B show the alignment of the transmembrane regions of LH/CG-R. The transmembrane regions of selected G protein-coupled receptors were aligned by Fastp (D. J. Lipman et al., *Science* 227:1435 (1985)) and hom.global (W. M. Fitch et al., *Proc. Natl. Acad. Sci. USA* 80:1382 (1983)) computer programs, with final adjustment by hand to maximize positional identity with minimal insertions. Numbers denote residue number; numbers in parentheses show the number of residues deleted in the 5–6 loop region. Boxed regions show matches of 3 or more residues at each position. Numbered bars indicated positions of putative transmembrane (TM) regions. RHO: bovine rhodopsin; SKR: Substance K receptor; β-2AR: β-2 adrenergic receptor; 5HT-2R: 5HT-2 (serotonin) receptor (Rhodopsin: J. Nathans et al., *Cell* 34:807 (1983); SKR: Y. Masu et al., *Nature* 329:836–838 (1987); β-2AR: R. A. F. Dixon et al., *Nature* 321:75 (1986); P. R. Schofield et al., *Nucl. Acids Res.* 15:3636 (1987); 5HT-2: D. B. Pritchett et al., *EMBO J.* 7:4135 (1988)).

(1985) (LRG); J. Lopez et al., *Proc. Natl. Acad. Sci. USA* 84:5615 (1987) (GP Ib); C. Hashimoto et al., *Cell* 52:269 (1988) (Toll); T. Kataoka et al., *Cell* 43:493 (1985) (Adenylate cyclase, yeast); T. Krusius et al., *Proc. Natl. Acad. Sci. USA* 83:7683 (1986) (PG40)). "a" indicates one of three aliphatic amino acids, valine, leucine, or isoleucine; "x" indicates any amino acid.

Figure 4:
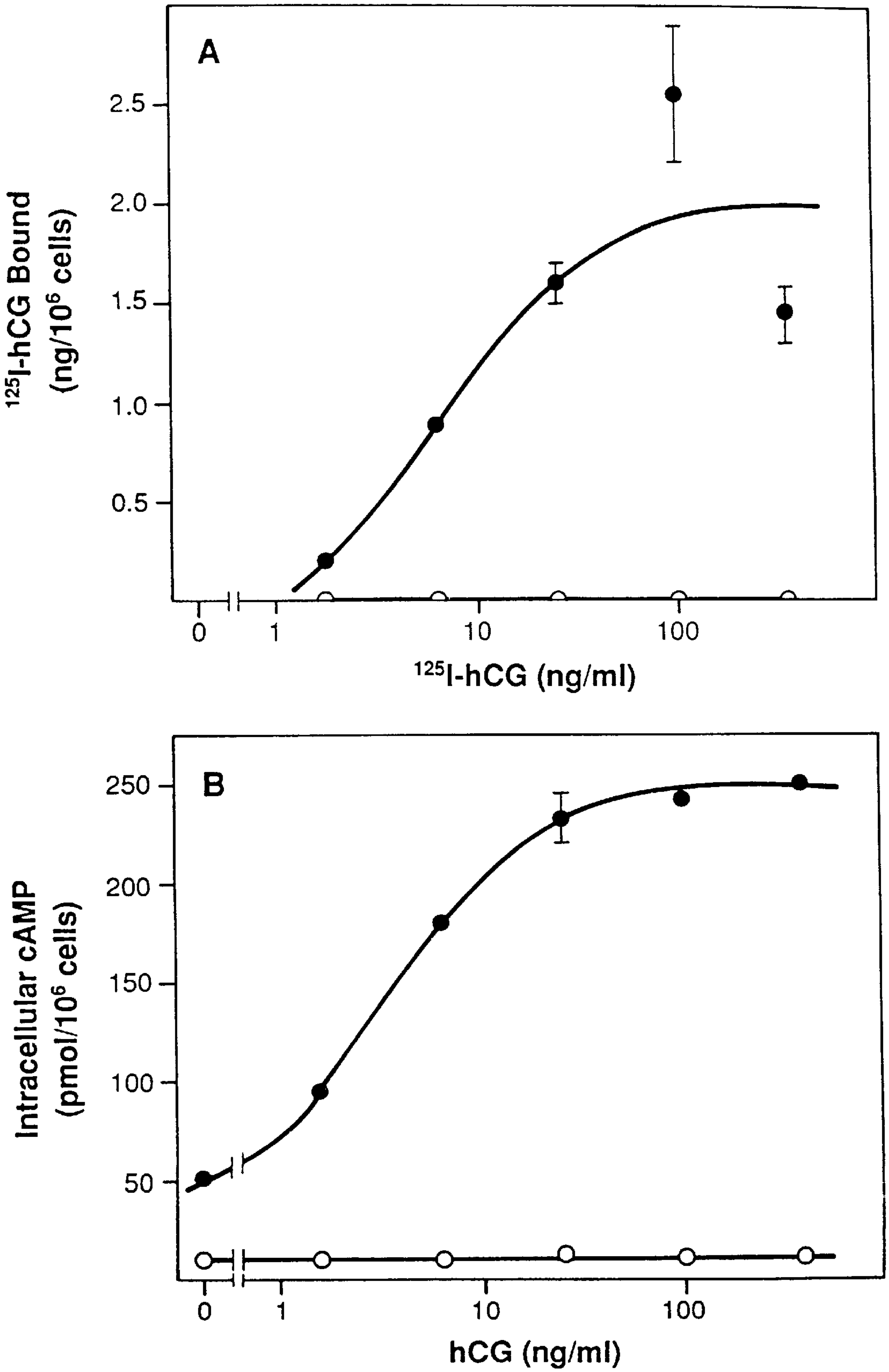

FIG. 4 shows the functional expression of the LH/CG-R cDNA. Specific $^{125}$I-CG binding (A) and CG-stimulated cAMP accumulation (B) in cos cells transiently transfected with (closed circles) or without (open circles) expression vector pCLHR.

FIGS 5A and 5B show a Northern analysis of the hybridization of LH/CG-R cDNA in different tissues. Each lane contained 10 $\mu$g of total RNA. Numbers on the left indicate kb as determined from DNA size markers. Samples shown are from the ovaries of pseudopregnant rats (lane a), and adult rat ovaries (lane b), testes (lane c), lung (lane d), kidney (lane e), liver (lane f). Panels A and B, respectively, are 6 hour and overnight exposures of the same blot FIGS. 6A and 6B show the cDNA and predicted amino acid sequence of rat testicular FSH-R. Amino acid numbering begins at the N-terminal sequence for the predicted mature receptor protein, with negative numbers denoting the signal sequence.

FIG. 7A and FIG. 7B show structural comparison between the gonadotropin receptors. A) Sequence similarities of receptor domains. The N-terminal half representing the extracellular domain is subdivided into 14 imperfectly duplicated units of approximately 20 residues each and the C-terminal half shows the seven transmembrane segments. Potential glycosylation sites are indicated by filled squares. Different shadings of grey indicate the degrees of sequence conservation for different receptor areas. B) Sequence comparison of receptors in the one letter code. The FSH-R sequence is shown as the lower sequence and differences as well as substitutions in the LH/CG-R are presented above. Dots denote insertions introduced for optimal alignment. The extracellular repeats are numbered and demarked by vertical lines. Conserved cysteine residues in the extracellular domain are denoted by filled ovals. Transmembrane regions TMI-TMVII are boxed. Small arrows indicate conserved cysteine residues in the second and third extracellular loops of the receptor.

Figure 8:
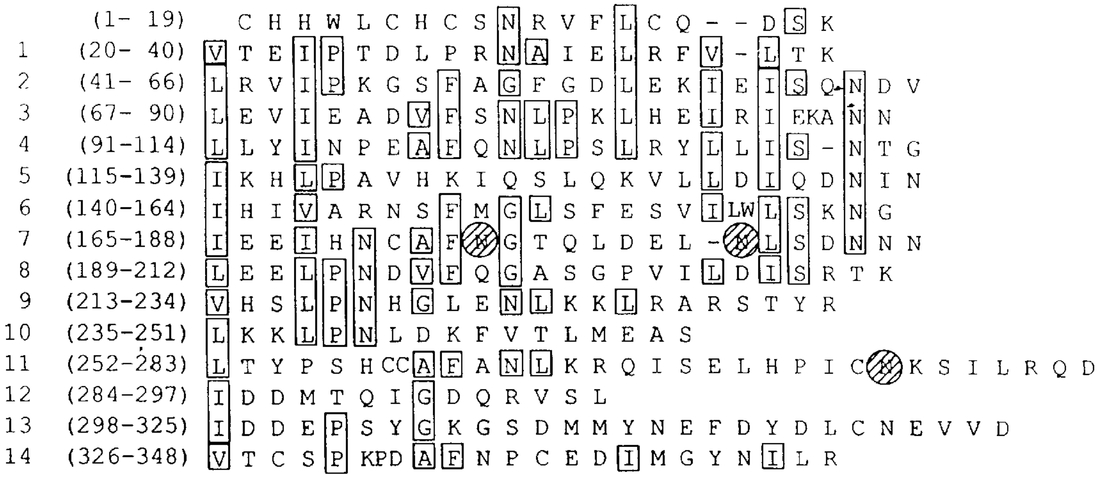

FIG. 8 shows alignment of repeated motifs in the extracellular domain of FSH-R illustrating the differential extent of sequence conservation between the repeats. N-linked glycosylation sites are indicated by hatched circles. The alignment and numbering is according to that of the LH/CG-R.

Figure 9:
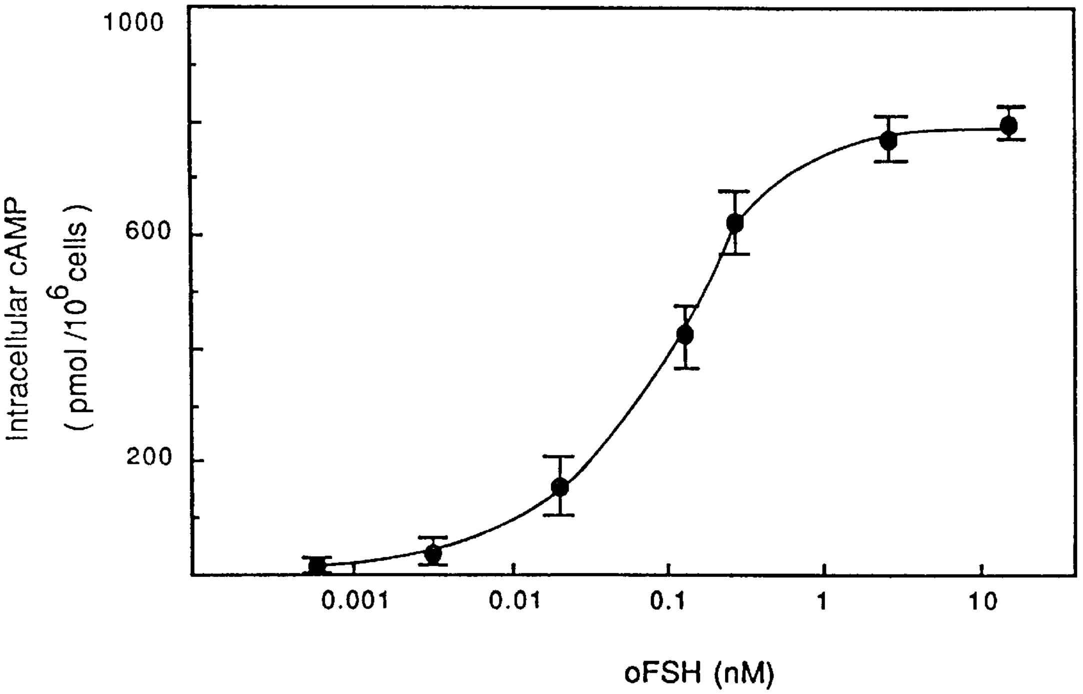

FIG. 9 shows functional expression of the FSH-R. FSH-stimulated cAMP accumulation in 293 cells transiently transfected with expression plasmid pCFSH-R. Intracellular c-AMP was measured as a function of hormone concentration. Each data point represents the mean ± range of duplicate determinations.

DESCRIPTION OF THE PREFERRED EMBODIMENTS

I. Luteinizing Hormone, Follicle Stimulating Hormone, and Thyroid Stimulating Hormone The present invention concerns the purification, cloning, and uses of the biological receptor for luteinizing hormone, choriogonadotropin, thyroid stimulating hormone, and follicle stimulating hormone.

As indicated above, luteinizing hormone (LH) and human choriogonadotropin (CG) are members of an evolutionarily conserved family of glycoprotein hormones which also includes thyroid stimulating hormone (TSH) and follicle stimulating hormone (FSH). All four are 28–38 kDa heterodimeric glycoproteins, each composed of a common $\alpha$-subunit combined with distinct $\beta$-subunits which confer receptor specificity (Pierce et al., *Annual Rev. Biochem.* 50:466 (1981)). The $\beta$-subunits of LH and CG are closely sequence-related and these two hormones bind to the same receptor and elicit identical biological responses (Pierce et al., supra). The acute response of target cells to the binding of LH and CG is an increase in adenylate cyclase activity mediated by intracellular, membrane-associated G proteins. The resulting increased levels of cAMP ultimately lead to an increase in steroid synthesis and secretion (M. Hunzicker-Dunn et al., in *Luteinizing Hormone Action and Receptors*, M. Ascoli (Ed.), CRC Press, Boca Raton, 1985, pp. 57–134). The carbohydrate moieties of these hormones appear to play an important role in signal transduction (Sairam et al., *J. Biol. Chem.* 264:2409 (1989)). The carbohydrate moieties of the hormones also increase their potency by decreasing the rate at which the hormones are metabolically cleared.

During recent years, a family of G protein-coupled receptors has been identified, whose members are characterized by the common structural feature of seven transmembrane domains (reviewed in R. J. Lefkowitz et al., *J. Biol. Chem.* 263:4993 (1988)). The receptor for these hormones is expected to be a member of this family.

The high degree of similarity between the binding domains of animal LH, FSH and TSH hormones compared to their human counterparts supports the conclusion that the cellular receptor molecules for these hormones will be capable of binding with the human hormone. Thus, such animal receptor molecules can be used in the same manner as human receptor molecules.

The luteinizing hormone/choriogonadotropin hormone receptor (LH/CG-R) is present on testicular Leydig cells, and on ovarian theca, granulosa, luteal and interstitial cells. The LH/CG receptor plays a pivotal role in reproductive physiology. In the male and the non-pregnant female, the LH/CG-R is exposed only to luteinizing hormone (LH), produced and secreted by the anterior pituitary. During pregnancy, however, the ovarian LH/CG-R is also exposed to human choriogonadotropin (CG), made by the placenta.

Progress towards the elucidation of the structure of the LH/CG-R has been hampered by the low abundance of this receptor and its susceptibility to proteolysis (M. Ascoli et al., *Endocrine Rev.* 10:27 (1989)). The rat LH/CG receptor was recently purified from ovaries of pseudopregnant rats (N. Rosemblit et al., *Endocrinology* 123:2284 (1988)) and has been reported to have been purified from porcine testes (Jallal, B. et al. *Reprod. Nutr. Dev.* 28:1177 (1988)).

The purified rat LH/CG receptor was found to be a single glycoprotein with a molecular mass of 93 kDa (N. Rosemblit et al., *Endocrinology* 123:2284 (1988); I.-C. Kim et al., *J. Biol. Chem.* 261:3807 (1986), M. Ascoli et al., *Endocrine Rev.* 10:27 (1989)). Other reports have, however, suggested that the LH/CG-R is composed of multiple subunits (reviewed in M. Ascoli et al., *Endocrine Rev.* 10:27 (1989)).

II. The Purification of Hormone Receptor Molecules

The methods and examples provided below are described in terms of the isolation and cDNA cloning of the LH/CG receptor ("LH/CG receptor"). It is to be understood, however, that such description can be adapted, without departure from the teachings of the present invention, to enable the isolation and cloning of not only the LH/CG receptor, but also the FSH and TSH receptors.

The hormone receptors of the present invention may be purified by routine adaptation of any of a variety of methods.

It is preferable to employ the method of Rosemblit, N. et al. (*Endocrinol.* 123:2284–2289 (1988)). In accordance with this method, the receptors are isolated by a combination of affinity chromatography, lectin binding and SDS-polyacrylamide gel electrophoresis.

To facilitate recovery, an enriched cellular source of receptor is employed. A preferred source of LH/CG receptor is rat luteal cells. Preferred sources of the FSH receptor are Sertoli cells. A preferred source of TSH receptor is thyroid tissue.

To obtain tissue samples, animals are sacrificed, or the desired tissue obtained by surgery. After removal of the receptor-containing tissue from the animal, the tissue is preferably placed in a buffer containing 150 mM NaCl, 20 mM HEPES, pH 7.4 ("Buffer A"). Tissue is preferably maintained at 4° C. Because the proteins may be extremely sensitive to proteolysis, the buffer employed is preferably adjusted to contain 5 mM N-ethylmaleimide, 10 mM phenylmethylsulfonylfluoride, and 10 mM ETDA to inhibit proteolysis (Kellokumpu, S. et al., *Endocrinol.* 116:707 (1985)).

Tissue samples are dispersed in 10 volumes of Buffer A using a tissue disrupter and then homogenized (preferably using a motor-driven Teflon pestle). Dispersed cellular preparations are centrifuged (for example at 20,000×g for 30 minutes) and resuspended in 5 volumes of Buffer A supplemented to contain 20% glycerol ("Buffer B") and 1% NP-40 (which agents may stabilize the binding activity of the receptors). The preparations are then subjected to high speed centrifugation (100,000×g for 1 hour). The receptors are found in the supernatant of such centrifugation, and can be stored at −70° C.

In a preferred embodiment, the receptor molecules may be further purified by affinity chromatography using purified hormone as a ligand. Preparations of highly purified hormone can be obtained commercially. Hormone from such a preparation may be coupled to a (preferably) immobilized resin such as Affi-Gel 10 (Bio-Rad, Richmond Calif.) or the like, by means well known in the art. The resin is equilibrated in the above-described buffer (preferably supplemented to contain 0.5% NP-40 and 20% glycerol), and the preparation of receptor molecules is placed in contact with it. After sequentially washing the resin with suitable buffers (Buffer B containing 0.5% NP-40; Buffer B containing 0.5M NaCl and 0.1% NP40; Buffer B containing 0.1% deoxycholate; Buffer B containing 0.1% NP-40; and a solution of 0.1% NP-40, 20% glycerol, and 50 mM glycine, pH 3), receptor molecule is eluted using preferably a buffer of 50 mM glycine, pH 3, 0.1% NP-40, 20% glycerol, and 100 mM NaCl.

In order to assay the eluted material for receptor molecules, an aliquot of sample is incubated in the presence of an excess of labeled hormone molecules. Radioactive iodine is a preferred label. A preferred method for assaying receptor is described by Roche, P. C. et al., *Endocrinol.* 117:790 (1985)). After assay, filtration is preferably performed, for example, using the method of Buettner, K. et al., *J. Biol. Chem.* 259:15078 (1984)). The pH of sample fractions found to contain receptor molecule is preferably neutralized with Tris.

In order to further purify the receptor molecules, wheat germ agglutinin purification may be performed. This may conveniently be accomplished by incubating pooled, receptor-containing, affinity purified fractions in the presence of wheat-germ agglutinin-agarose (Vector Laboratories, Burlington, Calif.). After permitting adsorption to occur, the gel may be washed to remove impurities. Receptor may then be eluted from the gel (using, for example, 0.32M N-acetylglucosamine in Buffer B containing 0.1% NP-40, or other buffer) and assayed in the manner described above.

Further purification may be achieved through the use of either analytical or preparative gel electrophoresis. Any suitable method of electrophoresis may be employed such as those of Kim, I.-C. et al., (*J. Biol. Chem.* 262:470 (1987) or Laemmli, U. K. (*Nature* 227:680 (1970)). Visualization of the electrophoresed material may be accomplished by silver stain (Wray, W. et al., *Anal. Biochem.* 118:197 (1981)) or other means. For preparative gel electrophoresis, the material is preferably concentrated in the manner disclosed by Holloway, P. W. (*Anal. Biochem.* 53:304 (1973)) before electrophoresis.

The receptor protein may be further purified by filtration/concentration using, for example, Centricon filter concentrators. The sample may then be further purified by acetone precipitation, followed by gel electrophoresis. The bands obtained from such electrophoresis may be electroeluted, and used to determine the amino acid sequence of the amino terminus of the protein.

Alternatively, the electroeluted receptor protein may be further precipitated using methanol/chloroform, and digested with an endopeptidase in order to obtain a set of peptide fragments. These fragments can then be sequenced in order to elucidate their amino acid sequence.

Alternatively, the electroeluted receptor molecules (may be reprecipitated with acetone, resuspended in buffer (such as Tris, pH 8.5), and cleaved with formic acid/CNBr. The cleavage products can be lyophilized, resolved on a tricine gel, and sequenced. The identification of a preparation which contains a substantially purified hormone receptor molecule (either the receptor for luteinizing hormone, choriogonadotropin, follicle stimulating hormone, or thyroid stimulating hormone) permits the amino acid sequence of the receptor molecule to be determined, and further permits the molecule to be produced through the application of recombinant DNA techniques.

Thus, the present invention includes not only substantially purified hormone receptor molecules, and methods for their use, but also includes the amino acid sequences of these receptor molecules, the genetic sequences coding for these receptor molecules, vehicles containing such genetic sequences, hosts transformed therewith, and hormone receptor molecules produced through transformed host expression.

In order to obtain the amino acid sequence of the hormone receptor molecules, the receptor molecules in the substantially purified fractions are recovered by any suitable method. Most preferably, such recovery is accomplished by lectin and hormone affinity chromatography as generally described by N. Rosemblit et al., (*Endocrinology* 123:2284 (1988)), followed by concentration of sample using Centricon-30 (Amicon), and resolution by gel electrophoresis. The recovered molecules may then be sequenced, preferably using an automated sequenator, and the amino acid sequence of the molecule thereby determined. Although any suitable means can be used to determine the sequence of the hormone receptor molecules, it is preferable to determine the sequence using the microsequencing methods of Rodriguez (*J. Chromatog.* 350:217 (1985)). Alternatively, the hormone receptor molecule may be purified by electrophoresis and, after electroelution, cleaved by cyanogen bromide or lysyl-C endopeptidase. The fragments may then be resolved, preferably by HPLC or by tricine gels (H. Shägger et al., *Anal. Biochem.* 166:368 (1987)) followed by electroblotting and gas-phase microsequencing. The sequence of the complete molecule can then be determined.

III. Cloning of Hormone Receptor Molecules

Although the elucidation of the total sequence of a hormone receptor molecule permits one to synthesize the molecule (for example by Merrifield synthesis, etc), it is preferable to produce the receptor molecule via recombinant DNA technology from a gene sequence which encodes the receptor molecule.

To achieve this goal, one may use the genetic code (Watson, J. D., In: *Molecular Biology of the Gene,* 3rd Ed., W. A. Benjamin, Inc., Menlo Park, Calif. (1977), pp. 356–357) to predict, from the complete amino acid sequence of a hormone receptor molecule, the sequence of a DNA molecule which can encode and express the molecule.

In a preferred embodiment, the elucidation of the amino acid sequence of a peptide fragment of the hormone receptor molecule is used to enable one to isolate a gene sequence which is capable of encoding the entire receptor protein. In this embodiment, the amino acid sequence of the receptor molecule is determined through an analysis of the DNA or, more preferably, the cDNA sequence, of the gene which encodes the molecule (cDNA is preferred since it does not possess intervening sequences or "introns" which may be present in a eukaryotic genomic sequence, and which cannot be correctly expressed in prokaryotic hosts). In order to obtain these nucleic acid sequences, a source which contains the hormone receptor molecule gene or cDNA sequence is screened with oligonucleotide probes which encode fragments of the hormone receptor molecule.

In order to prepare the oligonucleotide probes, substantially purified hormone receptor molecule is recovered and fragmented as with cyanogen bromide, or with proteases such as papain, chymotrypsin, trypsin, lysyl-C endopeptidase, etc. (Oike, Y., et al., *J. Biol. Chem.* 257:9751–9758 (1982); Liu, C., et al., *Int. J. Pept. Protein Res.* 21:209–215 (1983)). The resulting peptides are separated, preferably by HPLC, or by resolution on tricine gels and electroblotting onto PVDF membranes, and subjected to amino acid sequencing. To accomplish this task, the peptides are preferably analyzed by automated sequenators.

Once one or more suitable peptide fragments have been sequenced, the DNA sequences capable of encoding them are examined. If a peptide is greater than 6 amino acids long, this sequence information is generally sufficient to permit one to clone a gene sequence such as those which encode the hormone receptor molecules of the present invention. Because the genetic code is degenerate, however, more than one codon may be used to encode a particular amino acid (Watson, J. D., In: *Molecular Biology of the Gene,* 3rd Ed., W. A. Benjamin, Inc., Menlo Park, Calif. (1977), pp. 356–357). Thus, it is probable that more than one oligonucleotide sequence can be identified which would be capable of encoding a particular hormone receptor molecule peptide fragment.

The probability that a particular oligonucleotide will, in fact, constitute the actual hormone receptor molecule fragment-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the receptor molecule fragment's peptide sequences is identified and synthesized.

As indicated above, the degeneracy of the genetic code makes it highly likely that a set of several oligonucleotides can be synthesized whose members will each be capable of hybridizing to a particular peptide fragment. Importantly, whereas all of the members of this set contain oligonucleotides which are capable of encoding the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the hormone receptor molecule fragment peptide is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate a gene sequence which encodes the receptor molecule (Maniatis, T., et al., *Molecular Cloning, A Laboratory Manual*, Cold Spring Harbor Press, Cold Spring Harbor, N.Y. (1982)).

The DNA probe may be labeled with a detectable group. Such detectable group can be any material having a detectable physical or chemical property. Such materials have been well-developed in the field of immunoassays and in general most any label useful in such methods can be applied to the present invention. Particularly useful are enzymatically active groups, such as enzymes (see *Clin. Chem.* 22:1243 (1976)); enzyme substrates (see British Pat. Spec. 1,548,741)); coenzymes (see U.S. Pat. Nos. 4,230,797 and 4,238,565)); enzyme inhibitors (see U.S. Pat. No. 4,134, 792); fluorescers (see *Clin. Chem.* 25:353 (1979)); chromophores; luminescers (such as chemiluminescers and bioluminescers (see *Clin. Chem.* 25:512 (1979))); specifically bindable ligands; proximal interacting pairs; and radioisotopes such as $^{3}H$, $^{35}S$, $^{32}P$, $^{125}I$ and $^{14}C$. Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled probe can be detected by adding the enzyme for which the label is a cofactor and a substrate for the enzyme. For example, one can use an enzyme which acts upon a substrate to generate a product with a measurable physical property. Examples of the latter include, but are not limited to, beta-galacto-sidase, alkaline phosphatase and peroxidase.

A suitable oligonucleotide, or set of oligonucleotides, which is capable of encoding a fragment of the gene sequence which encodes the hormone receptor molecule (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the receptor molecule.

Single-stranded oligonucleotide molecules complementary to the "most probable" hormone receptor molecule peptide encoding sequences can be synthesized using procedures which are well known to those of ordinary skill in the art (Belagaje, R., et al., *J. Biol. Chem.* 254:5765–5780 (1979); Maniatis, T., et al., In: *Molecular Mechanisms in the*

*Control of Gene Expression*, Nierlich, D. P., et al., Eds., Acad. Press, New York (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Maniatis, T., et al., (In: *Molecular Cloning, A Laboratory Manual*, Cold Spring Harbor Laboratories, Cold Spring Harbor, N.Y. (1982)), and by Haymes, B. D., et al., (In: *Nucleic Acid Hybridization, A Practical Approach*, IRL Press, Washington, D.C. (1985)). A DNA sequence coding for a hormone receptor molecule may be derived from a variety of sources. mRNA coding for any of these receptor molecules may be isolated from the tissues of any species that produces the receptor molecule, and identified using the Northern blot method (Alwine et al., *Method Enzymol.* 68:220–242 (1979)) and labeled oligonucleotide probes. The mRNA of such cells may then be converted to cDNA by techniques known to those skilled in the art. Alternatively, genomic DNA may be isolated and employed. The source of DNA or cDNA used will preferably have been enriched for the gene sequence which encodes the receptor molecule. Such enrichment can most easily be obtained from cDNA obtained by extracting RNA from cells, which produce high levels of the receptor molecule. For LH/CG, such cells are luteal cells. For TSH, such cells are thyroid cells. For FSH, the preferred cell source is Sertoli cells, or immature granulosa cells.

Any of a variety of methods may be used to clone a gene sequence which encodes the hormone receptor molecules of the present invention. One such method entails analyzing a shuttle vector library of cDNA inserts (derived from a cell that expresses the desired receptor molecule) for the presence of an insert which contains a gene sequence which is capable of encoding the receptor molecule. Such an analysis may be conducted by transfecting cells with the vector, and then assaying for receptor molecule expression.

To identify and clone the gene sequence capable of encoding any of the receptor molecules of the present invention, a DNA, or more preferably a cDNA, library is screened for its ability to hybridize with the oligonucleotide probes described above. Suitable DNA preparations (such as human genomic DNA) are enzymatically cleaved, or randomly sheared, and ligated into recombinant vectors. The ability of these recombinant vectors to hybridize to the above-described oligonucleotide probes is then measured. Vectors found capable of such hybridization are then analyzed to determine the extent and nature of the receptor molecule sequences which they contain. Based purely on statistical considerations, a gene sequence capable of encoding any of the hormone receptor molecules of the present invention could be unambiguously identified (via hybridization screening) using an oligonucleotide probe having only 18 nucleotides.

In an alternative way of cloning a gene sequence which encodes the receptor molecules of the present invention, a library of expression vectors is prepared by cloning DNA or, more preferably, cDNA (from a cell capable of expressing the receptor molecule) into an expression vector. The library is then screened for members capable of expressing a protein which binds to a hormone receptor molecule-specific antibody, and which has a nucleotide sequence that is capable of encoding polypeptides that have the same amino acid sequence as the receptor molecule, or fragments thereof. In this embodiment, DNA, or more preferably cDNA, is extracted and purified from a cell which is capable of expressing the receptor molecule. The purified cDNA is fragmented (by shearing, endonuclease digestion, etc.) to produce a pool of DNA or cDNA fragments. DNA or cDNA fragments from this pool are then cloned into an expression vector in order to produce a genomic or cDNA library of expression vectors whose members each contain a unique cloned DNA or cDNA fragment.

Thus, in summary, the production of a substantially pure preparation of a hormone receptor molecule permits one to determine the sequence of a peptide fragment of the receptor. Using this information, it is possible to derive the sequence of a theoretical "most probable" DNA sequence, or a set of such sequences, capable of encoding peptide sequence of these receptor molecules. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe to identify and isolate a gene sequence capable of encoding any of the receptor molecules of the present invention.

Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *Eur. Mol. Biol. Organ. J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985)).

In the same manner in which the rat LH/CG receptor molecule was purified, and used to obtain a gene sequence capable of encoding the rat LH/CG receptor, it is possible to purify the rat FSH, or TSH receptors.

The structure and sequence of the LH/CG, FSH, and TSH hormones and their respective receptors are highly conserved in mammals. Thus, for example, the rat LH/CG receptor is capable of binding to the LH, and CG of humans and other mammals. Similarly the rat FSH and TSH receptors are capable of (respectively) binding the FSH and TSH of humans and other mammals. These facts enable one to employ the rat LH/CG, FSH and TSH receptors to treat animal, and, in particular, human, conditions and diseases which are associated with these hormones and their respective receptors.

The conserved structure and sequence of the mammalian LH/CG, FSH and TSH receptors, and the elucidation of the cDNA sequence which encodes the rat LH/CG receptor make it possible to clone gene sequences from other mammals which encode the LH/CG, FSH, or TSH receptor. Of particular interest to the present invention is the ability to clone the human LH/CG, FSH and TSH receptor molecules using the above-described rat LH/CG receptor encoding gene sequence.

In a preferred embodiment of the present invention, the first step for obtaining a gene sequence which encodes the rat FSH or TSH receptor, or the LH/CG, FSH, or TSH receptor of any other mammal (particularly humans) comprises obtaining DNA from cells which contain such gene sequences (or more preferably, cDNA is obtained from cells which express such receptors). This DNA is used to prepare a genomic (or, more preferably, cDNA) library. Techniques for preparing such libraries are disclosed by Maniatis, T., et al., (In: *Molecular Cloning, A Laboratory Manual*, Cold Spring Harbor Laboratories, Cold Spring Harbor, N.Y. (1982)).

To identify and isolate the desired gene sequence, the above-described library is then screened for gene sequences which hybridize to a probe sequence of either the entire rat LH/CG receptor encoding sequence described above, a sequence complementary to such receptor encoding sequence, or a fragment of either of such sequences. Thus, for example, to isolate a DNA molecule which is capable of encoding the human FSH (or TSH) receptor, human FSH- (or TSH-) receptor expressing cells are used to produce a DNA (or cDNA) library. The members of this library are screened for their ability to hybridize with the above-described rat LH/CG probe sequence using techniques, such as those disclosed by Maniatis, T., et al. (In: *Molecular Cloning, A Laboratory Manual*, Cold Spring Harbor Laboratories, Cold Spring Harbor, N.Y. (1982)), or by Haymes, B. D., et al. (In: *Nucleic Acid Hybridization, A Practical Approach*, IRL Press, Washington, D.C. (1985)).

As is generally known to those of ordinary skill, such hybridization may be accomplished under a variety of conditions of stringency so as to permit either a stable hybrid to form only between two gene sequences which have very similar sequences (high stringency) or to permit such a hybrid to form between two gene sequences having more divergent sequences (low stringency). Conditions of high stringency employ high temperatures (such as 50–65° C.) and high concentrations of agents such as formamide (for example 50% formamide). Conditions of low stringency employ lower temperatures (approximately 42° C.) and lower concentrations of agents such as formamide (for example 20–40% formamide) ((Lawler, M. et al., *Bone Marrow Transpl.* 3:473 (1988); Bhattacharya, S. et al., *Ind. J. Med. Res.* 87:144 (1988); Arif, B. M. et al., *Virus Res.* 2:85 (1985); Smith, G. E. et al., *Virol* 123:393 (1982); Priestly, J. V. et al., *Histochem.* 89:467 (1988); Rohrmann, G. F. et al., *J. Gen. Virol.* 62:137 (1982). When employing hybridization conditions of 42° C. and 20% formamide, two gene sequences having approximately 10% homology can form a stable hybrid (Rohrmann, G. F. et al., *J. Gen. Virol.* 62:137 (1982)).

Once members of the library have been identified which are capable of hybridizing to the probe, it shall be necessary to determine whether they encode the LH/CG, FSH, or TSH receptor molecules (or a fragment thereof). Such characterization may be conveniently performed in any of several ways. Preferably, the gene sequence can be introduced into a suitable host cell, expressed, and the expressed receptor tested for its ability to bind to LH, CG, FSH or TSH. A gene sequence which expresses a receptor that is capable of binding to LH, CG, FSH or TSH, encodes the LH, CG, FSH or TSH receptor, respectively. Alternatively, the expressed molecule can be tested for its ability to bind to antibody (prepared as described below) that is reactive with the LH/CG, FSH, or TSH receptor. The autoantibodies produced by patients with Graves Disease may be used to determine whether an expressed receptor is the TSH receptor.

In the event that the expressed molecule is unable to bind to LH, CG, FSH, or TSH, it may be concluded that the isolated sequence encodes only a fragment of the desired gene sequence. Accordingly, the isolated gene sequence is used to identify and isolate any missing fragments of the desired gene sequence (Bender, W. et al., *J. Supramolec. Struc.* 10(*suppl*):32 (1979); Chinault, A. C., et al., *Gene* 5:111 (1979); Clarke, L. et al., *Nature* 287:504 (1980)). Once any such sequences have been identified and isolated, it is possible to construct a single gene sequence which is capable of encoding the entire desired receptor molecule using well known methods of recombinant DNA technology.

Covalent modifications of the hormone receptor molecules of the present invention are included within the scope of this invention. Variant hormone receptor molecule fragments having up to about 100 residues may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'-N-C-N-R') such as 1-cyclohexyl-3-(2-morpholinyl)-(4-ethyl) carbodiimide or 1-ethyl-3 (4 azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the hormone receptor molecule to a water-insoluble support matrix or surface for use in the method for cleaving a hormone receptor molecule fusion polypeptide to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention. Other modifications include hydroxylation of proline and lysine, phosphorytation of hydroxyl groups of seryl or theonyl residues, methylation of the $\alpha$-amino groups of lysine, arginine, and histidine side chains (T. E. Creighton, *Proteins: Structure and Molecule Properties*, W.H. Freeman & Co., San Francisco, pp. 79–86 (1983)), acetylation of the N-terminal amine, and, in some instances, amidation of the C-terminal carboxyl groups.

Amino acid sequence variants of the hormone receptor molecule can also be prepared by mutations in the DNA. Such variants include, for example, deletions from, or insertions or substitutions of, residues within the amino acid sequence shown in FIG. 1. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

At the genetic level, these variants ordinarily are prepared by site-directed mutagenesis of nucleotides in the DNA encoding the hormone receptor molecule, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed variants screened for the optimal combination of desired activity. Techniques for making substitution mutations at predetermined sites in DNA having a known sequence are well known, for example, site-specific mutagenesis. Preparation of a hormone receptor molecule variant in accordance herewith is preferably achieved by site-specific mutagenesis of DNA that encodes an earlier prepared variant or a nonvariant version of the protein. Site-specific mutagenesis allows the production of hormone receptor molecule variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (*USA*) 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete hormone receptor molecule sequence) may range generally from about 1 to 10 residues, more preferably 1 to 5. An example of a terminal insertion includes a fusion of a signal sequence, whether heterologous or homologous to the host cell, to the N-terminus of the hormone receptor molecule to facilitate the secretion of mature hormone receptor molecule from recombinant hosts.

The third group of variants are those in which at least one amino acid residue in the hormone receptor molecule, and preferably, only one, has been removed and a different residue inserted in its place. Such substitutions preferably are made in accordance with the following Table 1 when it is desired to modulate finely the characteristics of a hormone receptor molecule.

TABLE 1

| Original Residue | Exemplary Substitutions |
|---|---|
| Ala | gly; ser |
| Arg | lys |
| Asn | gln; his |
| Asp | glu |
| Cys | ser |

TABLE 1-continued

| Original Residue | Exemplary Substitutions |
|---|---|
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to be made are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native hormone receptor molecule-encoding nucleic acid, expression of the variant nucleic acid in recombinant cell culture, and, optionally, purification from the cell culture, for example, by immunoaffinity adsorption on a polyclonal anti-hormone receptor molecule column (to absorb the variant by binding it to at least one remaining immune epitope).

The activity of the cell lysate or purified hormone receptor molecule variant is then screened in a suitable screening assay for the desired characteristic. For example, a change in the immunological character of the hormone receptor molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

IV. Expression of the Hormone Receptor Molecules

DNA or cDNA molecules which encode a hormone receptor molecule for LH, CG, FSH, or TSH, can be operably linked into an expression vector and introduced into a host cell to enable the expression of the receptor molecule by that cell. Two DNA sequences (such as a promoter region sequence and a desired receptor molecule encoding sequence) are said to be operably linked if the nature of the linkage between the two DNA sequences does not (1) result in the introduction of a frame-shift mutation, (2) interfere with the ability of the promoter region sequence to direct the transcription of the desired receptor molecule encoding gene sequence, or (3) interfere with the ability of the desired receptor molecule gene sequence to be transcribed by the promoter region sequence.

A DNA sequence encoding a hormone receptor molecule may be recombined with vector DNA in accordance with conventional techniques, including blunt-ended or stagger-ended termini for ligation, restriction receptor molecule digestion to provide appropriate termini, filling in of cohesive ends as appropriate, alkaline phosphatase treatment to avoid undesirable joining, and ligation with appropriate ligases.

The present invention encompasses the expression of the desired receptor molecule in either prokaryotic or eukaryotic cells. Preferred eukaryotic hosts include yeast (especially Saccharomyces), fungi (especially Aspergillus), mammalian cells (such as, for example, human or primate cells) either in vivo, or in tissue culture.

Yeast and mammalian cells are preferred hosts of the present invention. The use of such hosts provides substantial advantages in that they can also carry out post-translational peptide modifications including glycosylation. A number of recombinant DNA strategies exist which utilize strong promoter sequences and high copy number of plasmids which can be utilized for production of the desired proteins in these hosts.

Yeast recognize leader sequences on cloned mammalian gene products and secrete peptides bearing leader sequences (i.e., pre-peptides). Mammalian cells provide post-translational modifications to protein molecules including correct folding or glycosylation at correct sites.

Mammalian cells which may be useful as hosts include cells of fibroblast origin such as VERO or CHO-K1, and their derivatives. For a mammalian host, several possible vector systems are available for the expression of the desired receptor molecule. A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

The expression of the desired receptor molecule in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (*London*)

290:304–310 (1981)) and; the yeast gal4 gene promoter (Johnston, S. A., et al., *Proc. Natl. Acad. Sci.* (*USA*) 79:6971–6975 (1982); Silver, P. A., et al., *Proc. Natl. Acad. Sci.* (*USA*) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the desired receptor molecule does not contain any intervening codons which are capable of encoding a methionine (i.e., AUG). The presence of such codons results either in the formation of a fusion protein (if the AUG codon is in the same reading frame as the desired receptor molecule encoding DNA sequence) or a frame-shift mutation (if the AUG codon is not in the same reading frame as the desired receptor molecule encoding sequence).

The expression of the hormone receptor molecules can also be accomplished in prokaryotic cells. Preferred prokaryotic hosts include bacteria such as *E. coli*, Bacillus, Streptomyces, Pseudomonas, Salmonella, Serratia, etc. The most preferred prokaryotic host is *E. coli.* Bacterial hosts of particular interest include *E. coli* K12 strain 294 (ATCC 31446), *E. coli* X1776 (ATCC 31537), *E. coli* W3110 ($F^-$, $lambda^-$, prototrophic (ATCC 27325)), and other enterobacteria (such as *Salmonella typhimurium* or *Serratia marcescens*), and various Pseudomonas species. The prokaryotic host must be compatible with the replicon and control sequences in the expression plasmid.

To express the desired receptor molecule in a prokaryotic cell (such as, for example, *E. coli, B. subtilis*, Pseudomonas, Streptomyces, etc.), it is necessary to operably link the desired receptor molecule encoding sequence to a functional prokaryotic promoter. Such promoters may be either constitutive or, more preferably, regulatable (i.e., inducible or derepressible). Examples of constitutive promoters include the int promoter of bacteriophage λ, and the bla promoter of the β-lactamase gene of pBR322, etc. Examples of inducible prokaryotic promoters include the major right and left promoters of bacteriophage λ ($P_L$ and $P_R$), the trp, recA, lacZ, lacI, gal, and tac promoters of *E. coli*, the α-amylase (Ulmanen, I., et al., *J. Bacteriol.* 162:176–182 (1985)), the σ-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli,* Academic Press, Inc., New York (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream from the gene-encoding sequence. Such ribosome binding sites are disclosed, for example, by Gold, L., et al., (*Ann. Rev. Microbiol.* 35:365–404 (1981)).

The desired receptor molecule encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired receptor molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can be utilized. Examples of such expression vectors include the yeast 2-micron circle, the expression plasmids YEP13, YCP and YRP, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance,* Cold Spring Harbor Laboratory, Cold Spring Harbor, N.Y., p. 445–470 (1981); Broach, J. R., *Cell* 28:203–204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others.

Preferred prokaryotic vectors include plasmids such as those capable of replication in *E. coli* such as, for example, pBR322, ColE1, pSC101, pACYC 184, or πVX. Such plasmids are, for example, disclosed by Maniatis, T., et al., (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, New York (1982), pp. 307–329). Suitable Streptomyces plasmids include pIJ101 (Kendall, K. J., et al., *J. Bacteriol.* 169:4177–4183 (1987)), and Streptomyces bacteriophages such as fC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al., (*Rev. Infect. Dis.* 8:693–704 (1986)), and Izaki, K. (*Jpn. J. Bacteriol.* 33:729–742 (1978)).

Once the vector or DNA sequence containing the constructs has been prepared for expression, the DNA constructs may be introduced into an appropriate host. Various techniques may be employed, such as protoplast fusion, calcium phosphate precipitation, electroporation or other conventional techniques. After the fusion, the cells are grown in media and screened for appropriate activities. Expression of the sequence results in the production of the hormone receptor molecule.

The hormone receptor molecules of the invention may be isolated and purified from the above-described recombinant molecules in accordance with conventional methods, such as extraction, precipitation, chromatography, affinity chromatography, electrophoresis, or the like.

V. The Molecules of the Present Invention

The present invention concerns the receptors of the luteinizing hormone, choriogonadotropin, follicle stimulating hormone and thyroid stimulating hormone. As used herein, the term "hormone receptor" includes not only the membrane bound receptor molecule, but also soluble (i.e. not membrane bound), entire (i.e. having the complete amino acid sequence of the hormone receptor) receptor molecules. The term "hormone receptors" additionally includes the functional derivatives of such molecules. The term "hormone receptors" additionally includes both glycosylated and unglycosylated forms of any of the above-described molecules.

As used herein, a "functional derivative" of a molecule is a compound which possesses a biological activity (either functional or structural) that is substantially similar to a biological activity of that molecule. The term "functional derivatives" is intended to include the "fragments," "variants," "analogs," or "chemical derivatives" of a molecule. The term "fragment" is meant to refer to any polypeptide subset of the molecule. Fragments of the LH, CG, FSH, or TSH receptors which are capable of specifically binding LH, CG, FSH or TSH (respectively) are of special importance to the present invention. The term "variant" is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical. The term "analog" is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). "Toxin derivatized" molecules constitute a special class of "chemical derivatives." A "toxin-derivatized" molecule is a molecule which contains a toxin moiety. The binding of such a molecule to a cell brings the toxin moiety into close proximity with the cell and thereby promotes cell death. Any suitable toxin moiety may be employed; however, it is preferable to employ toxins such as, for example, the ricin toxin, the diphtheria toxin, radioisotopic toxins, membrane-channel-forming toxins, etc. Procedures for coupling such moieties to a molecule are well known in the art.

The invention is further directed to hormone agonists or antagonists which bind to the receptor molecule, and to the functional derivatives of such agonists and antagonists. The agonists and antagonists of the present invention may be peptides, proteins, or may be non-proteinaceous organic molecules. All of the above-cited molecules comprise the molecules of the present invention.

As used herein, a "hormone agonist" is a non-immunoglobulin molecule which is capable of binding to a hormone receptor and whose binding to such receptor either (1) mimics the ability of any other molecule to bind to the receptor and to thereby mediate a physiologically significant (i.e. detectable) effect or (2) increases the ability of any other molecule to bind to the receptor and to thereby mediate a physiologically significant effect. An example of a hormone agonist is an organic molecule, or a protein other than LH, which exhibits luteinizing hormone activity.

As used herein, a "hormone antagonist" is a non-immunoglobulin molecule which is capable of binding to a hormone receptor and whose binding to such receptor prevents or attenuates the ability of any other molecule to bind to the receptor and to thereby mediate a physiologically significant (i.e. detectable) effect.

VI. Uses for the Molecules of the Present Invention

A. Purification of Hormone

The molecules of the present invention can be used for a variety of biochemical, diagnostic, and therapeutic purposes. One major use of the purified receptor molecules of the invention is in the production and purification of hormone. The capacity of the receptor molecules of the present invention to bind to hormone permits their use in the affinity purification of the hormone.

Thus, for example, LH/CG receptor may be employed to assist in the purification of LH or CG. These hormones may be used to induce ovulation, treat infertility, etc. The thyroid stimulating hormone receptor ("TSH receptor") may be used to purify TSH. TSH may be used in the treatment of hypothyroidism, or (when toxin-derivatized) in the treatment of thyroid cancer. The follicle stimulating hormone receptor may, similarly, be employed in the purification of FSH, for use in treating infertility, etc. In addition, because GP hormones have been shown to exhibit variable activity based on glycosylation, these receptors can be used to select the most bioactive form of the GP hormone.

B. Anti-Receptor Antibody

The hormone receptor molecules of the present invention may be used to induce the formation of anti-hormone receptor antibodies. Such antibodies may either be polyclonal or monoclonal antibodies, or antigen binding fragments of such antibodies (such as, for example, F(AB) or $F(AB)_2$ fragments). Of particular significance to the invention are antibodies (and antigen binding fragments of antibodies) which bind to the extracellular domain of a hormone receptor molecule. The most preferred anti-hormone receptor antibodies (and antigen binding fragments thereof) are those which are capable of preventing or inhibiting the binding of the hormone to its hormone receptor.

Suitable polyclonal antibodies can be obtained by immunizing an animal or human with an immunogenic amount of the receptor molecule (preferably with an adjuvant, such as Freund's adjuvant). In lieu of such immunization, patients can be screened to identify those who naturally produce anti-receptor antibodies (such as patients with Graves Disease who produce anti-TSH receptor antibodies).

Alternatively, monoclonal antibodies may be prepared, such as by immunizing splenocytes with a particular receptor and then fusing an immunized cell with a myeloma cell (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, New York, pp. 563–681 (1981)) in order to obtain a hybridoma cell that secretes an anti-receptor monoclonal antibody.

Of special interest to the present invention are antibodies which are produced in humans, or are "humanized" (i.e. non-immunogenic in a human) by recombinant or other technology such that they will not be antigenic in humans, or will be maintained in the circulating serum of a recipient for a longer period of time.

Humanized antibodies may be produced, for example, by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 2:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. U.S.A.* 84:214–218 (1987); Nishimura, Y. et al., *Canc. Res.* 47:999–1005 (1987); Wood, C. R. et al., *Nature* 314:446–449 (1985)); Shaw et al., *Natl. Cancer Inst.* 80:1553–1559 (1988). General reviews of "humanized" chimeric antibodies are provided by Morrison, S. L. (*Science,* 229:1202–1207 (1985)) and by Oi, V. T. et al., *BioTechniques* 4:214 (1986)).

Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)) or by the methods disclosed in U.S. Pat. Nos. 4,816,397 and 4,816,567.

C. Diagnostic Uses

In addition to their use in the purification of hormone, the receptor molecules of the present invention may be used as the basis for assays of hormone activity. Importantly, since such an assay measures a physiologically significant binding event (i.e. that of a hormone to its receptor and undergoing a detectable change (such as phosphorylation, cleavage, chemical modification, etc)) it is likely to be both more sensitive and more accurate than immunoassays (which detect the physiologically non-significant binding of hormone to anti-hormone antibody). Moreover, the LH/CG, FSH, and TSH receptor molecules are capable of distinguishing their respective hormones from other hormones with greater specificity than antibodies (which may cross react with structurally similar molecules).

Although more sensitive and accurate than antibodies, the receptor molecules of the invention can be used to assay hormone levels in a sample in the same ways in which antibodies are used.

The anti-receptor antibodies of the present invention may also be used for diagnostic purposes such as to measure the expression and function of a patient's hormone receptors. The anti-receptor antibodies can also be used in imaging in order to characterize tissue, or to define the presence and site of metastasized receptor-expressing cells.

For diagnostic purposes, the receptors and anti-receptor antibodies can be used in accordance with immunoassay technology. Examples of immunoassays are described by Wide at pages 199–206 of *Radioimmune Assay Method,* edited by Kirkham and Hunter, E. & S. Livingstone, Edinburgh, 1970.

Thus, in one embodiment, receptor molecules can be detectably labeled and incubated with a sample, and the amount of receptor molecule bound to the sample can be ascertained. In a second embodiment, antibody to the receptor, or to the hormone, can be used in order to create a "pseudo-sandwich immunoassay." In one such assay (a "forward" assay), a sample suspected of containing hormone can be incubated in the presence of an immobilized anti-hormone antibody. Solubilized, detectably labeled, hormone receptor molecules can be added to the reaction mixture, and the amount of hormone determined by measuring the amount of bound receptor.

As will be evident to those of ordinary skill, various alternative assays can also be devised. The assay may be a simple "yes/no" assay to determine whether hormone is present (as in an assay for CG to determine pregnancy) or may be made quantitative by comparing the measure of labeled molecule with that obtained for a standard sample containing known quantities of hormone.

In another type of assay, which may also be useful with the antigens of the present invention, "simultaneous" and "reverse" assays are used. A simultaneous assay involves a single incubation step, as the antibody (or receptor) bound to the solid support and labeled receptor (or antibody) are both added to the sample being tested at the same time. After the incubation is completed, the solid support is washed to remove the residue of fluid sample and uncomplexed labeled antibody. The presence of labeled molecules associated with the solid support is then determined as it would be in a conventional sandwich assay.

In the "reverse" assay, stepwise addition first of a solution of labeled molecule (either receptor or antibody) to the fluid sample followed by the addition of unlabeled molecule (either antibody or receptor) bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then carried out as in the simultaneous and forward assays.

As explained above, the hormone assays of the present invention require that at least one molecule be labeled with a "reporter molecule." Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc.

Examples of suitable non-radioactive isotopic labels include $^{157}Gd$, $^{55}Mn$, $^{162}Dy$, $^{52}Tr$, $^{56}Fe$, etc.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., (*Clin. Chim. Acta* 70:1–31 (1976)), and Schurs, A. H. W. M., et al., (*Clin. Chim. Acta* 81:1–40 (1977)). Coupling techniques mentioned in the latter are the glutaraldehyde method, the periodate method, the dimaleimide method, and the m-maleimidobenzyl-N-hydroxysuccinimide ester method.

In the practice of the present invention, enzyme labels are a preferred embodiment. No single enzyme is ideal for use as a label in every conceivable assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, beta-galactosidase, urease, glucose oxidase, glycoamylase, malate dehydrogenase, and glucose-6-phosphate dehydrogenase. Urease is among the more preferred enzyme labels, particularly because of chromogenic pH indicators which make its activity readily visible to the naked eye.

Nucleic acid molecules which encode the hormone receptor molecule (or a fragment thereof) can be used to determine the extent and rate of the expression of the hormone receptor in the cells of a patient. To accomplish such an assay, a sample of a patient's cells is treated, via in situ hybridization, or by other suitable means, and analyzed to determine whether the sample contains mRNA molecules capable of hybridizing with the nucleic acid molecule.

D. Therapeutic Uses

1. Uses Of The LH/CG/FSH Receptors a. Treatment of Fertility

Luteinizing hormone, choriogonadotropin, and follicle stimulating hormone are involved in human and animal fertility. The receptors of the present invention are capable of binding to these hormones, and hence of lessening the availability of these hormones to bind to receptors present on the surfaces of target cells.

Thus, the FSH and LH/CG receptor molecules of the present invention can be used as contraceptive agents to prevent oocyte development, ovulation, or pregnancy in females. Since FSH and LH are needed for spermatogenesis to occur, the administration of LH and FSH receptors to males will also result in infertility. Thus, LH and FSH receptors of the present invention can be used either in males or in females to prevent pregnancy. Significantly, the contraceptive effects of such agents are reversible (i.e. cessation of the therapy will restore the patient to a fertile state). The receptors may also be used to identify agonists capable of stimulating ovulation in females.

Although an entire receptor molecule may be employed as a contraceptive agent, it is preferrable to employ a soluble fragment of the entire receptor molecule which contains the extracellular domain of the receptor molecule. As discussed below, it is desirable to couple such a fragment to a non-proteinaceous polymer in order to increase the biological half-life of the molecule.

Although contraception can be achieved by providing either the LH/CG receptor, or the FSH receptor to male and female recipients, increased contraceptive efficacy can be obtained by providing a recipient with both of these receptor molecules (or their derivatives). Similarly, contraceptive efficacy can be increased by providing either (or both) of such molecules in combination with estrogen, progesterone, or other steroid hormone. Contraceptive efficacy can also be enhanced by providing recipients with other protein hormones, such as inhibin, which have contraceptive action.

The availability of recombinant molecules which encode the receptor molecules permits the isolation of variants (by mutagenesis, or other means) which bind hormone more tightly, or which have increased biological activity or half-life. Similarly, such molecules can be used to construct a hybrid receptor molecule capable of binding both FSH and LH/CG.

The contraceptive agents of the invention can, as described more fully below, be provided to recipients in any of a variety of manners. The agents can be provided in either a bound or an unbound (i.e. soluble) form.

In addition to the above stated contraceptive ability of the LH/CG and FSH receptors, the receptors can mediate a prolonged state of infertility by their capacity to serve as immunogens in the patient. Thus, the hormone receptor molecules can be provided to a patient in a form which is immunogenic, and thus causes the patient to produce antibodies to the receptor molecules. The presence of such antibodies in a patient's serum may render the patient infertile. Various methods have been developed for increasing the immunogenicity of natural proteins, and may be used in order to produce such antibodies (N. Rosemblit et al., *Endocrinology* 123:2284 (1988); Copping, S. et al., *J. Endocrinol.* 104:78 (1985); Pala, A. et al., *J. Clin. Endocrinol. Metab.* 67:1190 (1988)).

Administration of the receptor(s) may be by injection, preferably supplemented, performed by periodic booster injections (approximately 1–4 months between injections, and preferably 3 months between injections).

The invention especially concerns the administration of the FSH receptor to animals and humans as a means for inducing anti-FSH receptor antibodies capable of preventing the binding of FSH to the FSH receptor molecule. The production of such antibodies in males would act to inhibit spermatogenesis, and thereby serve as a contraceptive agent. The production of such antibodies in females would act to inhibit follicle development, and thereby serve as a contraceptive agent. Thus, administration of the receptors is used to produce an anti-fertility vaccine.

b. Treatment of Breast Cancer

Breast cancer is a major public health problem in the western world. It is one of the leading causes of death for women between the ages of 35–45. Many factors, such as age, menstrual and reproductive history, size of tumor, presence and number of any positive axillary nodes, etc. affect the prognosis of the disease.

In particular, the presence or absence of the estrogen receptor ("ER") protein has been considered to be especially important in determining the prognosis of the disease. Women who have high ER levels have a more favorable prognosis than women whose ER levels are intermediate or negative. In view of this finding, breast cancer patients may be provided with estrogen analogues in order to abolish estrogen or estrogen precursors. In more radical cases, adrenalectomy and or hyphoscheotomy is performed.

By administering the FSH receptor to an individual, it is possible to bind the individual's FSH molecules, and thereby prevent or attenuate their ability to induce ovarian cells to produce estrogen. Thus, such administration will result in the induction of estrogen receptor molecules. As discussed below in an alternative embodiment of the invention, the above-described anti-FSH receptor or anti-LH receptor antibodies can be provided to an individual to accomplish this goal. Hence, the present invention provides an alternative to the above-described conventional therapies.

c. Treatment of Prostate Cancer

Cancer of the prostate is one of the most common malignancies of men, and is a common cause of cancer death. Treatment for this disease includes the surgical removal of the prostate gland, chemotherapy, and radiation therapy. The fact that the growth of the prostate gland is dependent upon testicular androgens, provides an additional therapy for prostrate cancer. The level of such androgens has been lowered by castration, or estrogen therapy.

The present invention provides an alternative therapy for this disease. As discussed above, the principal action of LH in males is to induce Leydig cells to produce testosterone. Accordingly, by providing an individual with the LH/CG receptor and/or the FSH receptor it is possible to decrease the amount of LH in the serum which is available to induce testosterone biosynthesis. Hence, the administration of the receptor(s) will decrease testosterone synthesis, and thus cause the rate of growth of the prostate gland to decrease. Even where such therapy is insufficient to cause tumor regression or the cessation of tumor growth, such therapy may be useful in decreasing bone pain which is a symptom in most patients exhibiting an advanced stage of disease. In an alternative embodiment, the above-described anti-LH receptor antibodies can be provided to an individual to accomplish this goal.

d. Treatment of Osteoporosis

Many symptoms of menopause can be attributed to the increased circulatory levels of FSH and LH which are present in women during the menopausal years of their lives. Common symptoms of menopause include vasomotor instability ("hot flashes"), atrophy of the urogenital epithelium and skin, decreased size of the breasts, and osteoporosis.

The FSH and LH levels in women during their reproductive years is substantally lower than those found in women during menopause. FSH levels may increase approximately 8 fold; LH levels may increase approximately 6.5 fold (Petersdorf, R. G. et al. (Eds.), In: *Harrison's Principles of Internal Medicine,* 10th Ed. McGraw-Hill, New York, (1983), pp 704–705). This increase in circulating hormone levels can be countered by providing a woman with the FSH receptor and/or the LH/CG receptor.

Osteoporosis is the term used to describe a diverse set of diseases which are each characterized by a reduction in bone mass per unit volume to a level which is insufficient to provide adequate skeletal support. The present invention provides a means for treating (either prophylactically or therapeutically) osteoporosis by reducing LH and/or FSH levels. In accordance with such therapy, a woman is administered therapeutically effective amounts of the FSH receptor and/or the LH/CG receptor, which are capable of lowering her FSH and/or LH serum levels.

e. Treatment of Perimenopausal Vasomotor Instability

As indicated above, many symptoms of menopause can be attributed to the increased circulatory levels of FSH and LH which characterize menopause. Studies have shown that vasomotor instability ("hot flashes") are associated with a rise in LH levels. Thus, in addition to the above-described ability to provide a therapy for osteoporosis, the administration of the FSH and/or LH/CG receptors can be used to treat (i.e. prevent or ameliorate the symptoms of) vasomotor instability.

f. Treatment of Polycystic Ovarian Disease

In normal women, the levels of estrogen are closely synchronized with the reproductive cycle. The unsynchronized production of estrogen is characterized by infertility, hirsutism, obesity, and amenorrhea or oligomenorrhea. This condition is referred to as polycystic ovarian disease ("PCOD") (Petersdorf, R. G. et al. (Eds.), In: *Harrison's Principles of Internal Medicine,* 10th Ed. McGraw-Hill, New York, (1983),pp 710). The condition is characterized by high LH levels and low FSH levels.

Treatment of PCOD is directed toward interrupting the estrogen production. Such treatment may be accomplished by agents which decrease ovarian androgen secretion, or by enhancing FSH secretion.

The present invention provides a novel therapy for this disease. The transient administration of FSH receptor molecules may serve to induce increased FSH biosynthesis, such that the cessation of such administration results in an increase in FSH level. The administration of the LH/CG receptor acts to decrease the amount of LH available to bind to LH/CG receptors on ovarian cells, and thus causes the amount of androgen synthesized to decrease.

2. Uses of the TSH Receptor

As discussed above, Graves Disease is a disease of hyperthyroidism caused by the production of an immunoglobulin which is capable of binding to the TSH receptor, thus mimicking the action of TSH. The disease may be treated by providing a patient with antithyroid drugs, with radioactive iodine, or by surgical resection of the thyroid. In all cases, the approach of the therapy is to limit the amount of thyroid hormone which can be produced by the thyroid gland.

In accordance with the present invention, it is possible to treat Graves Disease by providing a patient with a therapeutically effective amount of the TSH receptor. The administered TSH receptor is capable of binding to the immunoglobulin which causes Graves disease. Thus, the administration of the receptor serves to decrease the amount of immunoglobulin which is capable of binding to the TSH receptors on the surfaces of thyroid cells. The administration of TSH receptors thus provides a therapy for Graves Disease which does not entail destruction of normal, healthy thyroid tissue. The receptor can also be used to reduce the physical effects of hyperthyroidism, especially during preparation for surgery in patients where surgery has been elected due to the severity of the disease. Alternatively, a TSH receptor coupled to a solid support matrix could be used to eliminate thyroid stimulating immunoglobulins extra-corporally by selective plasmapheresis.

The TSH receptor can additionally be used to treat benign prostatic hypertrophy.

3. Identification of Hormone Antagonists and Agonists

The availability of the LH/CG, FSH and TSH receptors permits their use in the screening, identification and characterization of agonists and antagonists of their respective hormones.

As discussed above, a hormone agonist may either be a molecule which increases the physiological effect caused by a hormone's interaction with its receptor, or a molecule which is capable of itself mediating any physiological effect which results from the interaction of the hormone and its receptor.

To identify agonists which increase the effect of a hormone, one may assay the capacity of a putative agonist for its ability to enhance the capacity of hormone to bind to a receptor. Agonists which mimic the activity of a hormone can be identified by their capacity to bind to the receptor molecule, and to mediate a physiologically significant effect which is a characteristic of the interaction of the hormone and its receptor. Hormone agonists can be used to increase the level or effectiveness of a hormone in an individual. Thus, they may be used to treat individuals suffering from an inadequate production of hormone.

The availability of receptor molecule also permits the identification of hormone antagonists. As discussed above, such molecules prevent or attenuate the ability of a hormone to interact with its receptor and thereby mediate a physiologically significant (i.e. detectable) effect. Such molecules can be identified by their ability to prevent or attenuate the binding of hormone to receptor molecules. Hormone antagonists can be used to decrease the level or effectiveness of a hormone in an individual. Hormone antagonists may, therefore, be used to treat conditions resulting from the overproduction of a particular hormone.

One class of agonists and antagonists of special concern to the present invention are immunoglobulin agonists or antagonists. The anti-receptor antibodies described above may be tested to determine whether their binding to receptor impairs or prevents the ability of the receptor to bind to its native ligand. Antibodies having such a capability are hormone antagonists, and may be used, in the same manner as the hormone receptor molecule, to treat individuals suffering from the excessive production or action of hormone. For example, an antibody which is an antagonist of LH may be used to treat vasomotor instability, etc. Similarly, an antibody which is an antagonist of TSH may be used to bind to the TSH receptor and provide a therapy for hyperthyroidism.

Similarly, the anti-receptor antibodies described above may be tested to determine whether their binding to a receptor mimics the binding of a hormone to that receptor. Antibodies having such a capability are hormone agonists, and may be used to treat individuals suffering from a deficiency of hormone production. For example, an antibody which is an agonist of FSH may be used to bind to the FSH receptor and thereby stimulate ovulation. Similarly, an antibody which is an agonist of TSH may be used to bind to the TSH receptor and provide a therapy for hypothyroidism.

Hormone agonists and antagonists can be labeled with toxins and used in the treatment of cancer. Thus, for example, a toxin-derivatized agonist or antagonist of TSH would be able to bind to the TSH receptor on malignant thyroid cells (or any cells which express the receptor), and thereby provide a means for killing such cells. Similarly, toxin derivatized FSH, CG, or LH agonists or antagonists could be used to kill neoplastic cells which express the FSH or LH/CG receptors.

Although the class of cells which normally express the TSH, FSH, and LH/CG receptors is limited, the availability of gene sequences which encode these molecules, and the existence of tissue specific promoters makes it possible to produce recombinant vectors which can mediate the expression of the receptors on diverse additional tissues. Thus, it is possible to use the methods of the invention to treat malignancies of other tissues.

VII. Administration of the Agents of the Present Invention

The therapeutic effects of the hormone receptor molecules, or the hormone agonist or hormone antagonist molecules, of the present invention may be obtained by providing to a patient the entire molecule, or any therapeutically active peptide fragment thereof. Of special interest are therapeutically active peptide fragments of such molecules which are soluble (i.e. not membrane bound). Preferred fragments are those which contain the extracellular domain of a hormone receptor.

The above-described molecules and their functional derivatives may be obtained either synthetically, through the use of recombinant DNA technology, or by proteolysis, or by a combination of such methods. The therapeutic advantages of such molecules may be augmented through the use of functional derivatives possessing additional amino acid residues added to enhance coupling to carrier or to enhance the activity of the molecules. The scope of the present invention is further intended to include functional derivatives of such molecules which lack certain amino acid residues, or which contain altered amino acid residues, so long as such derivatives possess (or affect) a biological or pharmacological activity possessed (or affected) by the hormone receptor molecules, or the hormone agonist or hormone antagonist molecules of the present invention.

The hormone receptor molecules, and hormone agonist or hormone antagonist molecules, of the present invention are said to be "substantially free of natural contaminants" if preparations which contain them are substantially free of materials with which these products are normally and naturally found.

The molecules of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of at least one of the molecules of the present invention, together with a suitable amount of carrier vehicle.

Additional pharmaceutical methods may be employed to control the duration of action. Control release preparations may be achieved through the use of polymers to complex or absorb the molecules of the present invention. One particularly preferred preparation results from conjugating a molecule of the present invention with a nonproteinaceous polymer in order to prepare a derivative molecule which is water soluble and exhibits other desired characteristics. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from nature. Hydrophilic polyvinyl polymers fall within the scope of this invention, e.g., polyvinylalcohol and polyvinylpyrrolidone. Particularly useful are polyalkylene ethers such as polyethylene glycol, polypropylene glycol, polyoxyethylene esters or methoxy polyethylene glycol; polyoxyalkylenes such as polyoxethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g., polymannuronic acid or alginic acid), D-glucosamine, D-galactosamine, D-glucose, and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g., hyaluronic acid; polymers of sugar alcohols such as polysorbitol and polymannitol; heparin; and polyamides such as polyserine or polyalanine. Where the polysaccharide is the native glycosylation or the glycosylation attendant on recombinant expression of any of the molecules of the present invention, the site of substitution ordinarily is located at other than an N- or O-linked glycosylation site of such molecule or the molecule used is an amino acid sequence variant in which an additional or substitute N- or O-linked site has been introduced into the molecule.

Mixtures of such polymers are employed, or the polymer may be homogeneous. The polymer prior to crosslinking need not be, but preferably is, water soluble, but the final conjugate must be water soluble. In addition, the polymer should not be highly immunogenic when conjugated to the molecule of the present invention, nor should it possess viscosity that is incompatible with intravenous infusion or injection if it is intended to be administered by such routes.

Preferably the polymer contains only a single group which is reactive with the molecule of the present invention. This helps to avoid cross-linking of the molecules. However, it is within the scope herein to optimize reaction conditions to reduce cross-linking, or to purify the reaction products through gel filtration or chromatographic sieves to recover substantially homogeneous derivatives.

The molecular weight of the polymer ranges about from 100 to 500,000 and preferably is about from 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation. Ordinarily, the molecular weight of the molecule of the present invention-polymer conjugate will exceed about 70,000, although molecules having lesser molecular weights are suitable.

The polymer generally is covalently linked to a molecule of the present invention through a multifunctonal crosslinking agent which reacts with the polymer and one or more amino acid or sugar residues of the molecule. However, it is within the scope of this invention to directly crosslink the polymer to such molecule by reacting a derivatized polymer with the molecule, or vice versa. Also within the scope hereof are noncovalent associative complexes of a molecule of the present invention and the polymer. Such complexes are most conveniently produced by noncovalently associating with the molecule electronegatively charged polymers such as dextran sulfate, heparin, heparan, chondroitin sulfate or other glycosaminoglycans; or amphoteric polymers having electronegative domains. An alkaline pI facilitates the formation of such complexes, which are produced by mixing solutions or suspensions of the polymers and the molecule, followed by removal of salts or drying in order to accelerate association between the polymer and the molecule.

The molecules of the present invention are preferably covalently crosslinked to the polymer. The preferred covalent crosslinking site of the molecules of the present invention is the N-terminal amino group and epsilon amino groups found on lysine residues, although other amino, imino, carboxyl, sulfhydryl, hydroxyl or other hydrophilic groups serve as useful sites of substitution on the molecules. The polymer may be covalently bonded directly to the molecule without the use of a multifunctional (ordinarily bifunctional) crosslinking agent. Examples of such crosslinking agents include 1,1-bis(diazoacetyl)-2-phenylethane, glutaraldehyde, N-hydroxysuccinimide esters, for example, esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane. Derivatizing agents such as methyl-3-[(p-azido-phenyl) dithio] propioimidate yield photoactivatable intermediates which are capable of forming cross-links in the presence of light. Alternatively, reactive water-soluble matrices such as cyanogen bromide-activated carbohydrates and the systems described in U.S. Pat. Nos. 3,959,080, 3,969,287, 3,691,016, 4,195,128, 4,247,642, 4,229,537, 4,055,635, and 4,330,440 are suitably modified for cross-linking the polymer and molecule. Covalent bonding to the amino groups of the molecules of the present invention is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride; or PEG chloride plus the phenoxide of 4-hydroxybenzaldehyde), succinimidyl active esters, activated dithiocarbonate PEG, 2,4,5-trichlorophenylchloroformate or p-nitrophenylchloroformate activated PEG. Carboxyl groups are derivatized by coupling PEG-amine using carbodiimide. Polymers are conjugated to the oligosaccharide substituents by chemical (e.g., metaperiodate) or enzymatic oxidation (e.g., glucose or galactose oxidase) (to produce the aldehyde derivative of the carbohydrate), followed by reaction with hydrazide or amino-derivatized polymers, in the same fashion as is described by Heitzmann et al., *Proc. Natl. Acad. Sci. USA* 71:3537–3561 (1974), or Bayer et al., *Methods in Enzymology* 62:310 (1979) for the labeling of oligosaccharides with biotin or avidin. Further, other chemical or enzymatic methods which have been used heretofore to link oligosaccharides and polymers maybe suitable. Substituted oligosaccharides are particularly advantageous for those molecules of the present invention in which the carbohydrate substituents are located in the C-terminal region of the extracellular domain and hence are not involved in binding to hormone; this will aid in preserving hormone binding activity while achieving other objects herein. Also, since there are fewer substitutions than amino acid sites for derivatization, the oligosaccharide products will be more homogeneous in general. The molecule's oligosaccharide substituents can be enzymatically modified to remove sugars, e.g., by neuraminidase digestion, prior to polymer derivatization.

The oligosaccharides of other glycoproteins than those described above are covalently substituted, preferably with PEG, in the same fashion as described above in order to accomplish the objectives of this invention with respect to the therapeutic uses for such glycoproteins.

The polymer will bear a group which is directly reactive with an amino acid side chain, or the N- or C-terminus of a molecule of the present invention, or which is reactive with the multifunctional cross-linking agent. In general, polymers bearing such reactive groups are known for the preparation of immobilized proteins. In order to use such chemistries here, one should employ a water-soluble polymer otherwise derivatized in the same fashion as insoluble polymers heretofore employed for protein immobilization. Cyanogen bromide activation is a particularly useful procedure to employ in cross-linking polysaccharides to a molecule of the present invention.

"Water soluble" in reference to the conjugate means that the conjugate is soluble in physiological fluids such as blood in an amount which is sufficient to achieve a therapeutically effective concentration. Thus, this excludes matrix-insolubilized molecules as may be used in affinity chromatography to purify hormone.

"Water soluble" in reference to the starting polymer means that the polymer or its reactive intermediate used for conjugation is sufficiently water-soluble to participate in a derivatization reaction with any of the molecules of the present invention.

The degree of substitution of a molecule of the present invention will vary depending upon the number of reactive sites on the protein, whether all or a fragment of the molecule is used, whether the molecule is a fusion with a protein heterologous to any of the molecules of the present invention, the molecular weight, hydrophilicity and other characteristics of the polymer, and the particular sites chosen. In general, the domain of the molecule of the conjugate is substituted with about from 1 to 10 polymer molecules, while any heterologous sequence which is fused to the molecule may be substituted with an essentially unlimited number of polymer molecules so long as the activity of the moiety is not significantly adversely affected. The optimal degree of cross-linking is easily determined by an experimental matrix in which the time, temperature, and other reaction conditions are varied to change the degree of substitution, after which the ability of the conjugates to bind hormone is determined.

In a preferred embodiment, PEG is cross-linked to any of the molecules of the present invention through a lysine residue and the N-terminal amino group.

The molecular weight of the conjugated polymer, e.g., PEG ranges about from 500 to 100,000. Molecular weights of 2,000, 5,000 or 20,000 are typical. The polymer, e.g., PEG, is cross-linked to a molecule of the present invention by a wide variety of methods known per se for the covalent modification of proteins with nonproteinaceous polymers such as PEG. Certain of these methods, however, are not preferred for the purposes herein. Cyanuric chloride chemistry leads to many side reactions, including protein cross-linking. In addition, it may be particularly likely to lead to inactivation of proteins containing sulfhydryl groups. Carbonyl diimidazole chemistry (Beauchamp et al., *Anal. Biochem.* 131:25–33 (1983)) requires high pH ($\leqq$8.5), which can inactivate proteins. Moreover, since the "activated PEG" intermediate can react with water, a very large molar excess of "activated PEG" over protein is required. The high concentrations of PEG required for the carbonyl diimidazole chemistry may lead to problems with purification, as both gel filtration chromatography and hydrophobic interaction chromatography may be adversely affected. On the other hand, aldehyde chemistry (Royer, U.S. Pat. No. 4,002,531) is more efficient since it requires only a 40-fold molar excess of PEG and a 1–2 hr incubation. However, the manganese dioxide suggested by Royer for preparation of the PEG aldehyde is problematic "because of the pronounced tendency of PEG aldehyde to form complexes with metal-based oxidizing agents" (Harris et al., *J. Polym. Sci. Polym. Chem. Ed.* 22:341–352 (1984)). Use of a moffatt oxidation, utilizing DMSO and acetic anhydride, obviates this problem. In addition, the sodium borohydride suggested by Royer must be used at a high pH and has a significant tendency to reduce disulfide bonds. In contrast, use of sodium cyanoborohydride, which is effective at neutral pH, has very little tendency to reduce disulfide bonds.

The conjugates of this invention are preferably separated from unreacted starting materials by gel filtration. Receptor molecules, for example, may be further purified by adsorption using anti-receptor antibodies (preferably monoclonal antibodies) or hormone, both preferably immobilized onto a matrix. Purification using hormone has the advantage that it only binds conjugates in which the degree or site of substitution has not resulted in the inactivation of hormone binding. PEG-substituted molecules may be further purified by hydrophobic interaction chromatography. Most conveniently, the conjugates are eluted from the hydrophobic chromatography medium, e.g., alkyl Sepharose, by the use of a decreasing salt gradient. This, as well as the gel filtration approach described above, resolves the conjugates on the basis of the degree of substitution so that it is possible to obtain a conjugate preparation which is substantially homogeneous in its degree of molar substitution by PEG, e.g., monosubstituted or disubstituted molecules which are essentially free of disubstituted or monosubstituted molecules, respectively. The derivatives herein may also be purified in most cases by ion exchange chromatography (adsorption of the molecule to a cation or anion exchange resin, followed by elution, or adsorption of contaminants to an anion or cation exchange resin).

The conjugates of this invention may be formulated into physiologically acceptable carriers and sterile filtered for therapeutic use. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The concentration of the molecules of the present invention in therapeutic formulations is not critical, but is typically about from 1 $\mu$g/ml to 20 mg/ml. The conjugates optionally contain a nonionic detergent such as Tween 20 or 80, salts, buffers, and other excipients. They are stored as aqueous solutions or lyophilized.

The conjugates are administered by subcutaneous, intramuscular, intravenous, or intracerebrospinal injection, intrapulmonary or intranasal aerosols, dermal patches, intravesicular infusion, or the like. When administering by injection, the administration may be by continuous infusion, or by single or multiple boluses.

The dosage will be determined in accord with clinical practice, and will vary depending upon such factors as the patient's age, weight, height, sex, general medical condition, previous medical history, etc. In general, it is desirable to provide the recipient with an initial dose of from about 10 $\mu$g/kg to about 300 $\mu$g/kg (body weight of patient)/1–3 times per week, although a lower or higher dosage may be administered. One advantage of the conjugates herein is that they are infrequently administered and do not need to be continuously infused in order to maintain therapeutic dosages in vivo.

The administration of such compound(s) may be for either a "prophylactic" or "therapeutic" purpose. When provided prophylactically, the compound(s) are provided in advance of any symptom of a disease, or sign of a condition. The prophylactic administration of the compound(s) serves to prevent or attenuate any subsequent disease or condition. When provided therapeutically, the compound(s) are provided at (or shortly after) the onset of a symptom of an existing disease, or the detection of a sign of an existing condition. The therapeutic administration of the compound(s) serves to attenuate the symptoms or such disease or condition.

Another possible method to control the duration of action by controlled release preparations is to incorporate any of the molecules of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remingtons's Pharmaceutical Sciences (1980).

Having now generally described the invention, the same will be more readily understood through reference to the following examples which are provided by way of illustration, and are not intended to be limiting of the present invention, unless specified.

EXAMPLE 1

Purification of the Rat Luteal LH/CG Receptor

Rat LH/CG receptor was purified according to the method of Rosemblit, N. et al. (*Endocrinol.* 123:2284–2289 (1988)) from the ovaries of pseudopregnant rats except that the wheat germ agglutinin chromatography was performed prior to the CG-affinity chromatography. The LH/CG-R thus obtained was purified by lectin and CG affinity chromatography and was then concentrated by Centricon-30 (Amicon).

The receptor protein was further purified by precipitation by incubation for 10 minutes at −20° C. in 5 volumes of acetone. The precipitate was centrifuged (12,000×g, 10 minutes), dissolved in Laemmli gel sample buffer and resolved by gel electrophoresis (Laemmli, U. K. (*Nature* 227:680 (1970)).

Silver staining of SDS gels of the purified material revealed a prominent band corresponding to a 93 kDa protein, with several less intensely stained lower Mr bands. The receptor was, thus, found to be composed of a single polypeptide having an approximate molecular weight of 93 kDa.

Use of the wheat germ column prior to the affinity column results in a somewhat greater purification of the receptor (as revealed by SDS gels). The purification of a 93 kDa protein using this procedure is consistent with our previous results on the structure of this receptor. Further substantiation that the purified 93 kDa protein is the LH/CG receptor, however, was obtained by two additional experiments. In one, the receptor was purified from the ovaries of pseudopregnant rats in which the LH/CG receptor was down-regulated. As would be predicted, the 93 kDa protein was not apparent in silver stained SDS gels of material purified from this source. In the other experiment, $^{125}$I-CG was incubated with Western blots prepared from SDS gels of the initial detergent extract and of the purified receptor. Specific binding was observed in both cases to a 93 kDa protein. Thus, it was concluded that the 93 kDa protein we have purified is indeed the LH/CG receptor.

Importantly, the purified LH/CG receptor appeared as a single 93 kDa band on SDS gels whether run in the presence or the absence of reducing agents. Thus, these data too suggest that the LH/CG receptor is a single polypeptide.

EXAMPLE 2

Formation of anti-Receptor Polyclonal and Monoclonal Antisera

Using the purified LH/CG receptor preparations, it was possible to obtain antibody to the receptor. To do this, a receptor-containing sample was diluted into Freund's complete adjuvant and injected subcutaneously into the back of a New Zealand White female rabbit. After 6 weeks, the rabbit was bled every week for 5 months. The sera of the rabbit was found to contain LH/CG-receptor specific polyclonal antibodies (Rosemblit, N. et al., *Endocrinol.* 123:2284–2289 (1988)). This antibody was, however, unable to prevent the binding of CG or LH to the receptor. A second polyclonal antibody preparation has, however, been obtained, in accordance with the above-described methods, which does inhibit the binding of CG to the receptor. A third polyclonal antibody preparation has been obtained using the above-described methods which specifically binds to a synthetic peptide corresponding in sequence to the extracellular domain of CG.

EXAMPLE 3

Protein Sequencing and Molecular Cloning of the LH/CG-R

The above-described preparation of LH/CG receptor protein was subjected to further purification in order to determine its sequence.

To obtain the sequence of the N-terminal amino acids, the resolved 93 kDa receptor was electroblotted onto PVDF membranes (P. Matsudaira, *J. Biol. Chem.* 262:10035 (1987)) and the mature N-terminal sequence determined by gas-phase microsequencing (Rodriguez, *J. Chromatog.* 350:217 (1985)).

To determine the sequence of internal peptide fragments, two different protocols were employed. Peptide fragments Ihr26, and thr28 were prepared by precipitating the electroeluted receptor protein using methanol/chloroform. The protein was redissolved in 20 mM Tris, pH 8.5, 0.1% SDS, and digested with the Lysyl-C endopeptidase. The fragments obtained from this digestion were then resolved using HPLC, and sequenced.

The sequence of internal peptide fragments Ihrf, Ihrk, Ihrc, and Ihrr was determined by electroeluting the 93 kDa receptor, and precipitating the resulting protein in 5 volumes of acetone. The precipitate was dissolved in 20 mM Tris, pH 8.5, and treated with formic acid/CNBr in order to produce protein cleavage. The cleavage products were lyophilized three times, and redissolved in sample buffer for tricine gel electrophoresis (H. Shägger et al., *Anal. Biochem.* 166:368 (1987), followed by electroblotting and were subjected to gas-phase microsequencing.

Through such analysis, the above-described internal peptide fragments of different length were obtained and sequenced (FIGS. 1A–1C). The sequences of these polypeptide fragments are shown in the boxed insert at the bottom of FIGS. 1A–1C (sequences used for primers in the polymerase chain reaction (PCR) are underlined). Using the genetic code (Watson, J. D., In: *Molecular Biology of the Gene,* 3rd Ed., W. A. Benjamin, Inc., Menlo Park, Calif. (1977), pp. 356–357)), oligonucleotide probes were prepared which were capable of encoding the sequenced peptide fragments. Due to the degeneracy of the genetic code, multiple probes were prepared using alternative codons. The oligonuclotides constructed from these peptides sequences are shown in Table 2 (the different nucleotides of the alternative codons are shown below the oligonucleotide sequence at their corresponding positions in the sequence).

TABLE 2

```
ks: AAGGAGCTG(AG)TGGC(AG)C(C)GGAAGCCTGAGCCCAATGACTTCGCCCCTGATGGTGCCCT
             (TC)    (TC) (A)

rsrc: TGCACCTCCTCGAAGCAGTTGCCATACAGCTTCAGGGTCACA(CT)CTC
                                                 (GA)

fsrc: ACG(GG)GTCCAGGATG(CT)TGTGGCACCCTGGAAGGC(T)CC
         (AT)          (GA)                 (C)
```

Oligonucleotide mixtures of ks, rsrc and fsrc (500 ng each) were used for priming a polymerase chain reaction (PCR) (D. M. Fowlkes et al., *Proc. Natl. Acad. Sci. USA* 81:2313 (1984)) using as a template cDNA (25 ng) synthesized from pseudopregnant rat ovarian poly(A)$^+$ luteal RNA (P. Chomczynski et al., *Anal. Biochem.* 162:156 (1987)). The reaction was performed in 100 $\mu$l (67 mM Tris pH 8.3, 6.7 mM EDTA, 2.5 mM $MgCl_2$, 10 mM β-mercaptoethanol, 1.6 mM ammonium sulfate), using 1 U *Thermus aguaticus* thermostable DNA polymerase (Perkin Elmer—Cetus Instruments) and a DNA thermal cycler (Techne). Mineral oil (60 $\mu$l) was added to prevent evaporation. Reaction cycles (25) consisted of incubation at 95° C. for 1.3 min; 45° C., 2 min; 72° C., 5 min. DNA products were analyzed on a 1% agarose gel. Major DNA fragments were excised, eluted from the gel and inserted into the SmaI site of the M13 vector mp19 (J. Vieira et al., *Methods in Enzymology* 153:3 (1987)).

A distinct and prominent DNA product was generated by the polymerase chain reaction synthesis. Upon sequence analysis (F. Sanger et al., *Proc. Natl. Acad. Sci. USA* 74:5463 (1977)), this DNA product was found to contain 622 base pairs. The DNA product was found to contain part of the LH/CG receptor coding sequence, including the sequences for peptides Ihrr, Ihr26, and thr28 (cf. FIGS. 1A–1C and Table 2).

This PCR product was used as a probe for screening a rat luteal cDNA library (T. Maniatis et al., *Molecular Cloning—A Laboratory Manual*, Cold Spring Harbor Laboratory, New York (1982)). The fragment was used to probe a cDNA library ($10^6$ recombinant phage) constructed in λgt10 (R. D. Young et al., *Science* 222:788 (1983)) from pseudopregnant rat ovarian RNA. Of twenty hybridizing phage, twelve were further analyzed by DNA sequencing and used to determine the nucleotide sequence of the LH/CG cDNA.

The nucleotide and predicted amino acid sequence of the rat LH/CG-R cDNA with 43 nucleotides of 5' flanking and 759 nucleotides of 3' flanking sequence are shown in FIG. 1. The translation initiation codon at position 1 defines the start of a 2100 nucleotide long open reading frame which encodes all independently determined peptide sequences. The predicted N-terminal amino acid sequence constitutes signal peptide 26 residues (G. von Heijne, *Nucleic Acids Res.* 14:4683 (1986)). The sequence following the signal peptide corresponds to the peptide determined from the uncleaved LH/CG-R polypeptide. Hence, the mature LH/CG-R was concluded to begin with Arg and to be composed of 674 amino acid residues (Mr≈75 kDa).

EXAMPLE 4

Analysis of the Cloned Rat Luteal LH/CG Receptor

In summary, oligonucleotides based upon the N-terminal sequence and one of the internal sequences were used to prime rat luteal cDNA and the polymerase chain reaction was performed. The resulting 624 nucleotide cDNA encoded for the N-terminal amino acid sequence at one end and for the internal sequence used at its other end. Fortuitously, it also encoded within it additional internal amino acid sequence data that had been determined from the receptor. Thus, this cDNA was concluded to represent a partial cDNA for the rat luteal LH/CG receptor. It was then used to screen a rat luteal lambda gt10 library. From this a cDNA containing the complete coding sequence for the receptor has been obtained.

The open reading frame of this cDNA is 2100 nucleotides, encoding for a protein of 700 amino acids. The first 26 amino acids represent a signal sequence, as the N-terminal sequence derived from the intact protein follows thereafter. The calculated molecular weight of the mature protein is 75,000. We conclude that the difference between this and the molecular weight of the purified receptor (93,000) is attributable to the glycoprotein nature of the receptor.

Since the LH/CG receptor couples to a Gs protein, it was of immediate interest to ascertain whether this receptor shared any structural similarities with other G protein-coupled receptors that have been cloned and characterized thus far. These other receptors (which include for example rhodopsin, and the adrenergic, muscarinic acetylcholine, serotonin, and substance K receptor) all share a significant amino acid identity with each other and share a common structural motif of spanning the plasma membrane seven times (Lefkowitz, R. J. et al., *J. Biol. Chem.* 263:4993 (1988)). It should be noted, however, that these receptors, unlike the LH/CG receptor, also all bind relatively small ligands. An analysis of the hydropathy plot of the LH/CG receptor suggests that the C-terminal half of the protein does in fact have seven membrane-spanning domains. A comparison of the amino acids in this region of the LH/CG receptor with the amino acid sequences of the other G protein-coupled receptors shows a 18–22% identity, which is similar to that observed within the members of this family. In marked contrast to these other receptors, however, the LH/CG receptor has a large (approximately 340 amino acids in length) N-terminal domain which is relatively hydrophilic.

From these data, we postulate that the LH/CG receptor consists of a large N-terminal extracellular domain attached to a region that traverses the plasma membrane seven times, terminating with a small C-terminal cytoplastic tail.

It is likely that the extracellular domain involved in binding the large glycoprotein hormones CG and LH. This assignment is consistent with biochemical data showing that a 64 kDa water-soluble fragment of the LH/CG receptor can bind CG (Keinanen, K. P., *Biochem. J.* 239:83 (1986)) and with data from collagenase-treated cells.

The extracellular region of the receptor has many notable features. Firstly, there are six potential sites for N-terminal glycosylation. Preliminary data suggests that most of these sites are likely to be glycosylated. Secondly, there is a site consisting of 10 amino acids which is identical to a region in the soybean lectin (Schnell, K. J. et al., *J. Biol. Chem.* 262:7220 (1987)). It is well known that although the deglycosylated forms of CG and LH bind to the LH/CG receptor, they elicit little or no biological activity. Therefore, it will be interesting to test whether this site on the LH/CG receptor is involved in recognition of the carbohydrate chains of the hormone.

Thirdly, the extracellular domain can be aligned into a 14-fold imperfectly repeated motif of approximately 25 amino acids. The composition of this leucine-rich motif is common to a number of other proteins. These include proteins of such widely diverse (or unknown) functions as the yeast adenylate cyclase (Kataoka, T. et al., *Cell* 43:493–505 (1985)), the Toll developmental gene of Drosophila (Hashimoto, C. et al., *Cell* 52:269 (1988)), the human serum alpha2 glycoprotein (Takahashi, N. et al., *Proc. Natl. Acad. Sci.* (*U.S.A.*) 83:1906 (1985)), the platelet 1b receptor for von Willebrand factor and thrombin (Lopez, J. A. et al., *Proc. Natl. Acad. Sci.* (*U.S.A.*) 84:5615 (1987)), and the extracellular matrix proteoglycan PG40 (Krusius, T. et al., *Proc. Natl. Acad. Sci.* (*U.S.A.*) 83:7683 (1986)). It should be pointed out that of these proteins, only PG40 appears to share an overall amino acid homology with the extracellular region of the LH/CG receptor. The biological significance of this leucine-rich repeat structure is not really known. It has been suggested that it may be able to form an amphipathic helical structure and, therefore, may be involved in interacting with both an aqueous environment and the plasma membrane. This suggests that upon binding CG or LH the extracellular domain of the LH/CG receptor may interact with the membrane-spanning regions of the receptor.

As described above, the membrane-spanning region of the LH/CG receptor appears to be related to the family of receptors that couple to G proteins. Of the other G protein-coupled receptors that have been cloned thus far, only the beta-adrenergic receptor also couples to a Gs protein. The transmembrane half of the LH/CG receptor, however, shows no greater amino acid identity with the beta-adrenergic receptor than with receptors that couple to other G proteins, even in those regions postulated to be involved in Gs coupling (i.e., the C-terminal portion of the third cytoplasmic loop and the N-terminal portion of the cytoplasmic tail).

In examining the C-terminal cytoplasmic tail of the LH/CG receptor, numerous potential sites for phosphorylation (i.e., serines, threonines, and tyrosines) are apparent. The levels and/or functions of the LH/CG receptor may be modulated by phosphorylation. One other feature of this region of the LH/CG receptor is that it possesses two adjacent clusters of basic amino acids which suggest that the mature protein is post-translationally cleaved at one of these positions.

It has been shown for rhodopsin and for the beta-adrenergic receptor that their respective ligands bind to these receptors by intercalating within the membrane and interacting with the transmembrane helices. Thus, in these receptors this multiple membrane-spanning structural motif is important both for binding of the ligand and for coupling to the G protein. That the LH/CG receptor has evolved to also possess a large extracellular hormone-binding domain clearly sets it apart from these other receptors and suggests that (i) the seven transmembrane structure is an absolute requirement for coupling to the G protein; (ii) the translation of ligand binding to G protein coupling in the LH/CG receptor must be inherently different from that which occurs in other G protein-coupled receptors where the ligand intercalates within the membrane; and (iii) the LH/CG receptor evolved by a natural recombination between a soluble binding protein gene and G protein-coupled receptor gene.

The cDNA we have isolated hybridized to mRNA with a tissue and cell specificity expected for a cDNA to the LH/CG receptor. Thus, Northern blots prepared from total RNA from the ovaries of pseudopregnant rats and from the ovaries, testes, lung, liver and kidney of adult rats displayed hybridization to the LH/CG receptor cDNA only in the gonadal tissues. Of these, hybridization to the RNA of luteal tissue was most intense. Hybridization was predominantly to a 4.5 kb RNA, and to a lesser extent to several lower sized RNA's. When in situ hybridization was performed using sections obtained from a rat 9 days into pregnancy, intense hybridization to the corpora lutea was observed, with some hybridization occurring also in the theca and interstitial cells.

That the isolated cDNA encodes for a fully active LH/CG receptor is shown by transiently transfecting human kidney 293 cells (ATCC CRL 1573) with an expression vector in which the LH/CG receptor cDNA is under the transcriptional control of the cytomegalovirus promoter. These cells (as opposed to mock transfected 293 cells) specifically bind $^{125}$I-CG with high affinity (Kd 80–160 pM) and respond to CG with increased cAMP production ($EC_{50}$ 40–80 pM). The concentrations of CG required to elicit these responses are comparable to those observed in normal LH/CG receptor-bearing cells. Furthermore, the receptor encoded for by this cDNA shows the expected glycoprotein hormone binding specificity, in that CG and oLH, but not hTSH or hFSH, bind with high affinity and stimulate cAMP production. A more complete characterization of the LH/CG receptor expressed by this cDNA is currently being performed.

These results clearly demonstrate that the cDNA we have cloned encodes for the LH/CG receptor. Moreover, these data conclusively demonstrate that the LH/CG receptor is a single polypeptide which can both bind hormone and stimulate cAMP product when occupied.

EXAMPLE 5

Structure of the LH/CG Receptor as Determined By Chemical Crosslinking

An initial approximation of the size and organization of the cell surface LH/CG receptor was obtained by analyzing the products resulting from the chemical crosslinking of $^{125}$I-CG to target cells (Roche, P. et al., *J. Biol. Chem.* 264:4636 (1989)). In this approach either MA-10 Leydig tumor cells or primary cultures of porcine granulosa cells were incubated with $^{125}$I-CG labeled exclusively in either the alpha or the beta subunit. After washing to remove the unbound hormone, the bound $^{125}$I-CG was crosslinked to the cell surface hormone-binding component(s) using bifunctional succinimidyl esters and the radiolabeled crosslinked products were then analyzed by SDS polyacrylamide gel electrophoresis in the presence of reducing agents.

It was found that when the hormone was radiolabeled in the alpha subunit, hormone-receptor complexes of molecular masses equal to 107 kDa and 132 kDa were observed. Using hormone radiolabeled in the beta subunit, complexes equal to 117 kDa and 132 kDa were observed. The 132 kDa, 117 kDa, and 107 kDa complexes were concluded to represent the intact hormone (53 kDa), the beta subunit (33 kDa), and the alpha subunit (22 kDa), respectively, crosslinked to the same 83 kDa cellular component. Thus, these studies suggested that the LH/CG receptor is composed of a single polypeptide with a Mr=83,000 in both murine and Leydig tumor cells and in porcine granulosa cells.

It was also found that treatment of either cell type with collagenase type I (the preparation typically used to disperse tissues) prior to CG binding and crosslinking led to limited proteolysis of the LH/CG receptor. Thus, cells treated with collagenase bound CG with normal affinity and responded with increased steroid production normally. However, when $^{125}$I-CG was crosslinked to collagenase-treated cells and the products were resolved on SDS gels in the presence of reductants lower molecular weight crosslinked products (95 kDa, 75 kDa, and 63 kDa) were observed. The appearance of these lower Mr bands depended both on the concentration and length of time of collagenase treatment. The degradation of the receptor by treatment with collagenase is actually due to a contaminant(s) in the collagenase preparations, as highly purified collagenase did not have any proteolytic effects. Interestingly, when collagenase-treated cells were crosslinked to $^{125}$I-CG and the products were resolved on SDS gels in the absence of reductants, the receptor appeared intact. These results suggest that collagenase nicks the receptor, but that the overall structure (and binding activity) of the receptor is nonetheless maintained by intramolecular disulfide bonds.

By crosslinking $^{125}$I-CG to collagenase-treated cells and then analyzing the products in the presence of reductants, one can generate a peptide map of the receptor. Since collagenase treatment of both MA-10 cells and porcine granulosa cells yielded the same receptor products, the overall structure of the LH/CG receptor in these two cell types (Leydig versus granulosa) of two different species (murine versus porcine) is similar.

EXAMPLE 6

Structure of the LH/CG Receptor as Determined by Indirect Immunoprecipitation A second approach that was used to assess the overall structure of the LH/CG receptor was one in which the biosynthetically labeled receptor was specifically immunoprecipitated from MA-10 cells (Kim, I.-C. et al. (*J. Biol. Chem.* 262:470 (1987)). The immunoprecipitation was performed "indirectly" by immunoprecipitating the hormone-receptor complex using an antibody to CG.

Thus, MA-10 cells were biosynthetically labelled with $^{35}$S-cysteine and then were incubated with unlabeled CG. After washing the cells to remove the unbound hormone, the hormone-receptor complex was solubilized with detergent. It should be noted that solubilization of the hormone-occupied receptor without hormone dissociation is possible because CG shows little or no dissociation from its receptor so long as conditions are kept at 4° C. and at neutral pH. After partially purifying the hormone-receptor complex on a wheat germ agglutinin resin, it was precipitated with anti-CG and Protein A Sepharose. At this point, the radiolabeled receptor could be specifically eluted from the immunoprecipitate by a brief treatment with a pH 3 buffer, resolved on an SDS gel and visualized by fluorography. Therefore, in contrast to the chemical crosslinking method described above, this method has the advantage of allowing one to directly visualize the free receptor (not the hormone-receptor complex) on the SDS gel.

It was calculated that the acid-eluted receptor had been purified approximately 15,000 fold. A band, which corresponded to a protein of 93 kDa, was not observed in three independent negative controls done concurrently. Therefore, when the LH/CG receptor was down-regulated in the cells, when CG was omitted from the binding incubation, or when pre-immune IgG was substituted for immune anti-CG the 93 kDa protein not observed.

Since the immunoprecipitated LH/CG receptor appeared as a single protein of 93 kDa whether analyzed in the absence or the presence of reductants, it was concluded that the receptor consists of a single polypeptide. These results are in agreement with those observed by chemical crosslinking except that the estimated Mr of the receptor in those studies was 83 kDa. Of the two estimates, it is more likely that the 93 kDa determined from the indirect immunoprecipitations is more accurate since it is derived directly from the Rf of the free receptor (not hormone-receptor complex) on the SDS gels.

Further support for this conclusion comes from the finding that when the LH/CG receptor was indirectly immunoprecipitated from $^{35}$S-cysteine labelled cells that were treated with collagenase prior to binding CG, a diminished level of intact 93 kDa receptor (relative to the control cells) and the appearance of several smaller sized receptor fragments of 66 kDa, 50 kDa, and 32 kDa was observed

EXAMPLE 7

Domain Structure of the LH/CG-R

The N-terminal half of the polypeptide chain (residues 1–341) presumably constitutes the extracellular domain (FIGS. 1A–1C). Consonant with the glycoprotein nature of the LH/CG-R, there are six potential N-linked glycosylation sites within this domain. Preliminary evidence suggests that most of these sites are indeed glycosylated and this may account for the difference in molecular weight between the natural LH/CG-R (Mr≈93 kDa) and the predicted mature unglycosylated polypeptide (Mr≈75 kDa). In fact, molecular weights of CNBr fragments estimated by gel electrophoresis are consistent with an average contribution of 5–6 kDa per glycosylation site by oligosaccharide side chains.

The C-terminal half of the polypeptide (residues 342–674) contains seven hydrophobic segments of membrane-spanning length and displays sequence homology to all members of the G protein-coupled receptor family. Assuming a transmembrane topology identical to that suggested for rhodopsin (J. Nathans et al., *Proc. Natl. Acad. Sci. USA* 81:4851 (1984); R. Henderson et al., *Nature* 257:28 (1975); Y. A. Ovchinnikov, *FEBS. Lett.* 148:179 (1982)), the C-terminal 68 residues of the LH/CG-R are intracellularly located. This C-terminal domain contains potential phosphorylation sites (serine, threonine, and tyrosine residues) where cellular control of receptor activity may occur (D. R. Sibley et al., *Endocrine Rev.* 9:38 (1988)). This domain also contains two clusters of basic amino acids (at positions 623–625 and 630–632), raising the possibility that the mature receptor may be post-translationally cleaved to terminate at one of these positions (Post translational cleavage at KRR).

EXAMPLE 8

Homology to G Protein-Coupled Receptors

Figure 2B:
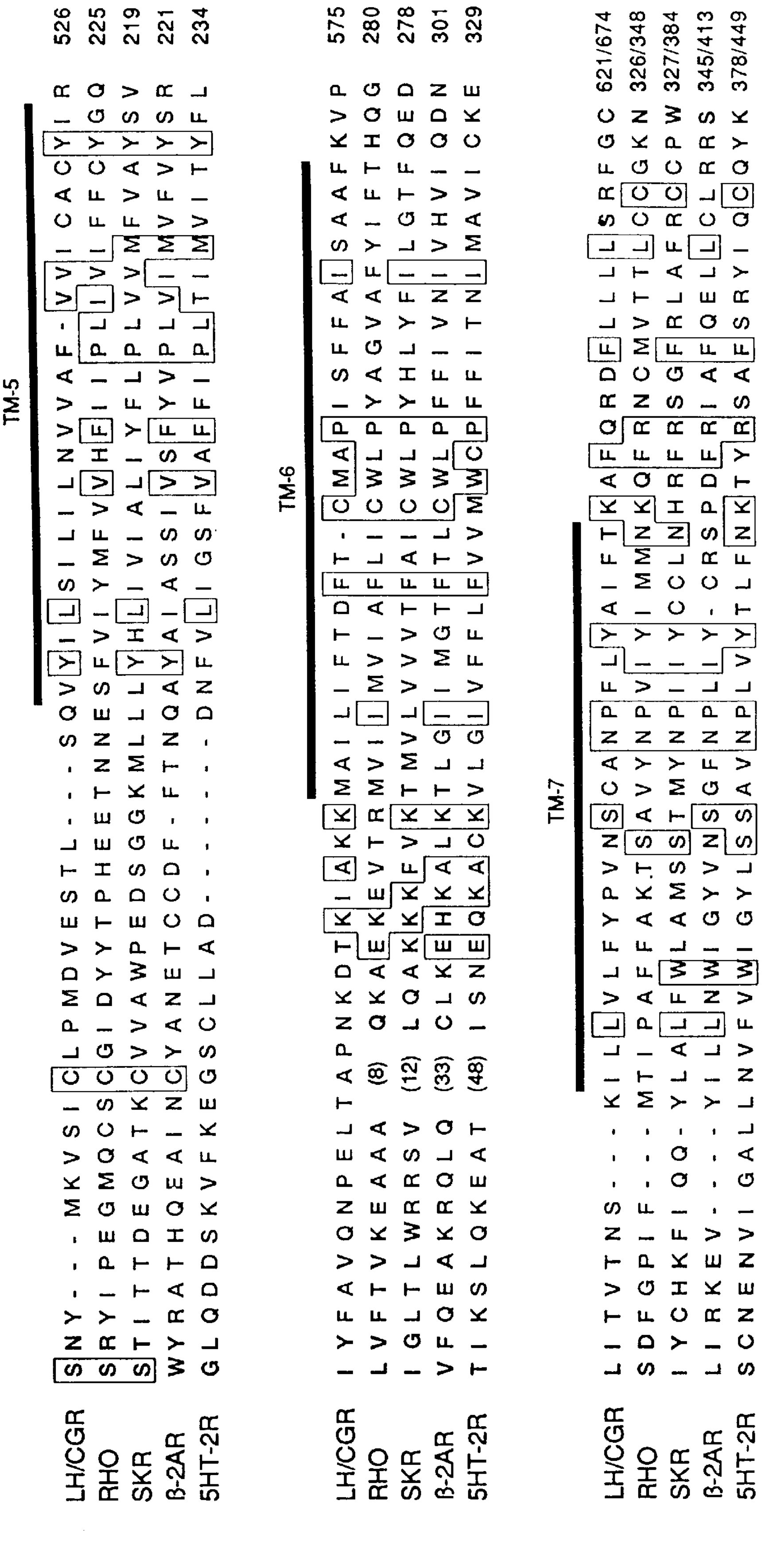

Membership of the LH/CG-R in the rapidly growing family of G protein-coupled receptors was consistent with the finding that LH and CG have been shown to activate adenylate cyclase via a G protein (M. Hunzicker-Dunn et al., in *Luteinizing Hormone Action and Receptors*, M. Ascoli, ed., CRC Press, Boca Raton, 1985, pp. 57–134). The homology of the LH/CG-R to other members of this receptor family was superficially revealed by a hydropathy plot and is shown in detail by an alignment with several members of this family across the seven putative transmembrane regions (FIGS. 2A–2B). This domain of the LH/CG-R shows an overall low but significant sequence similarity to other members. Similarity is highest to rhodopsin and the substance K receptor (22%) and lowest to receptors for classical neurotransmitters, e.g. muscarinic acetylcholine and serotonin (18–20%) (Rhodopsin: J. Nathans et al., *Cell* 34:807 (1983); SKR: Y. Masu et al., *Nature* 329:836–838 (1987); β-2AR: R. A. F. Dixon et al., *Nature* 321:75 (1986); P. R. Schofield et al., *Nucl. Acids Res.* 15:3636 (1987); 5HT-2: D. B. Pritchett et al., *EMBO J.* 7:4135 (1988); muscarinic receptor: T. Kubo et al., *Nature* 321:411 (1986)).

A number of short sequences were found to be highly conserved in all members and to occur within the putative transmembrane helices and intracellular loop regions. One of the conserved sites spans 6–7 residues located on the C-terminal end of the third cytoplasmic loop. This loop varies considerably in its length between different receptors, being shortest in LH/CG-R. The C-terminal region of this loop has been implicated in G protein-coupling, based on the analysis of mutant and chimeric receptors (B. F. Dowd et al., *J. Biol. Chem.* 263:15985 (1988); B. K. Kobilka et al., *Science* 240:1310 (1988); C. D. Strader et al., *J. Biol. Chem.* 262:16439 (1988); H. Kuhn, *Prog. Retinal Res.* 3:123 (1984)). This site is not more sequence-conserved between LH/CG-R and other receptors which couple to $G_S$ than between receptors known to interact with other G proteins.

EXAMPLE 9

The Extracellular Domain

Figure 3:
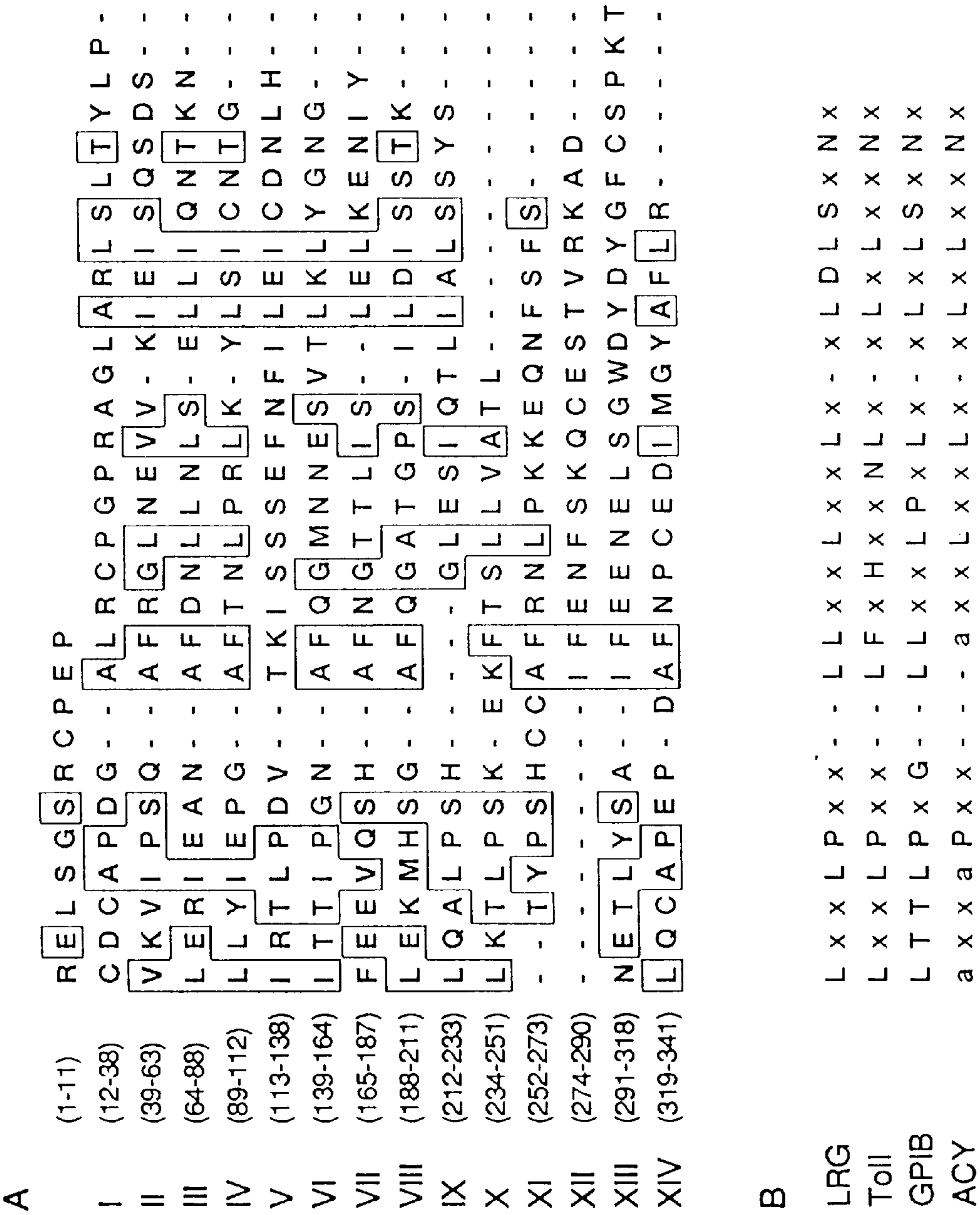
FIG. 3 shows the structure of the repetitive motif in the extracellular domain of the LH/CG-R. Panel A: Alignment of the 14 imperfect repeat structures. Identical or conserved residues among the segments I–XIV have been boxed. Dashes indicate the placement of gaps to optimize the periodicity. Panel B: Consensus sequences for the leucine-rich repetitive motifs observed in the leucine-rich alpha 2-glycoprotein of human serum (LGR), the alpha chain of human platelet glycoprotein Ib (GPIB), the Toll gene of Drosophila (Toll), and the yeast adenylate cyclase (ACY) (N. Takahashi et al., *Proc. Natl. Acad. Sci. USA* 82:1906

The extracellular, putative hormone binding domain displayed several significant sequence features. The most striking of these was a 14-fold imperfectly repeated sequence motif of approximately 25 residues with the C-terminal six repeats being the least conserved in length and sequence (FIG. 3*a*). Similar structures have been recognized in a variety of other proteins and have been termed leucine-rich repeats (N. Takahashi et al., *Proc. Natl. Acad. Sci. USA* 82:1906 (1985) (LRG); J. Lopez et al., *Proc. Natl. Acad. Sci. USA* 84:5615 (1987) (GP Ib); C. Hashimoto et al., *Cell* 52:269 (1988) (Toll); T. Kataoka et al., *Cell* 43:493 (1985) (Adenylate cyclase, yeast); T. Krusius et al., *Proc. Natl. Acad. Sci. USA* 83:7683 (1986) (PG40)).

The protein most similar to the extracellular domain is PG40, a proteoglycan abundant in extracellular matrices of connective tissues. Another protein containing similar repeats is the platelet glycoprotein Ib, a glycosylated membrane protein which is known to bind two glycosylated polypeptides, von Willebrand factor and thrombin. Further examples include such widely divergent polypeptides as yeast adenylate cyclase, and a Drosophila developmental gene product, Toll.

Although no common functions can be recognized for proteins containing such leucine-rich repeats, members of this family may interact with both hydrophobic and hydrophilic surfaces, possibly mediated by amphipathic helices formed by the repeat structures. The extracellular domain of the LH/CG-R may be responsible for both hormone binding and interaction with the transmembrane domains to mediate signal transduction.

Another feature observed within the extracellular domain constitutes a site defined by 10 residues identical with a sequence in soybean lectin (L. O. Vodkin et al., *Cell* 34:1023 (1983); D. J. Schnell et al., *J.Biol. Chem.* 262:7220 (1987) (Diflorus)) (cf. FIGS. 1A–1C). The site may be involved in the recognition of the glycosylated hormone and the functional coupling of the receptor to $G_S$, maximally achieved only with the glycosylated forms of LH and CG (Sairam et al., *J. Biol. Chem.* 264:2409 (1989)). Whereas deglycosylated hormone binds to the receptor with high affinity, this interaction leads to little or no stimulation of adenylate cyclase.

EXAMPLE 10

Functional Expression of the LH/CG-R

To confirm that the cloned cDNA indeed encodes the LH/CG-R, an expression vector, termed pCLHR, was constructed in which the putative receptor coding sequence was under the transcriptional control of the cytomegalovirus promoter (D. L. Eaton et al., *Biochemistry* 25:8343 (1986)).

In detail, the expression vector pCLHR was constructed by introducing the entire coding region of the cloned cDNA and additional flanking regions contained on an Eco R1 fragment (nucleotides-43 to 2559, see FIGS. 1A–1C) into the pCIS vector (D. L. Eaton et al., *Biochemistry* 25:8343 (1986)).

Exponentially growing 293 cells were transiently transfected (C. Chen et al., *Mol. Cell. Biol.* 7:2745 (1987)) with pCLHR. 42h after transfecton, intact cells were assayed for $^{125}$I-CG binding (FIG. 4A) or CG-stimulated cAMP production (FIG. 4B).

For the assay of $^{125}$I-CG binding (FIG. 4A), each dish was washed 4 times with 3 ml of warm Waymouth MB752/1 medium lacking sodium bicarbonate and containing 20 mM Hepes and 1 mg/ml bovine serum albumin and then placed in 2 ml of the same. After 2 hours at 4° C., aliquots of highly purified CG (CR-123, 12,780 IU/mg) iodinated as described by I.-C. Kim et al. (*J. Biol. Chem.* 261:3807 (1986)) were added alone or together with 50 IU crude CG (for the determination of non-specific binding). After 24 hours at 4° C., the binding media and cells were transferred to plastic tubes on ice. The cells were centrifuged, washed once with 2 ml cold 150 mM NaCl, 20 mM Hepes containing 1 mg/ml bovine serum albumin, and centrifuged. Cell pellets were counted in a gamma counter.

For the determination of CG-stimulated cAMP production (FIG. 4B), each dish was washed 4 times with 3 ml warm Waymouth MB752/1 medium containing 1 mg/ml bovine serum albumin and placed in 2 ml of the same containing 0.5 mM 3-isobutyl-1-methylxanthine. After a 15 min preincubation at 37° C., aliquots of highly purified CG were added and the incubation was continued for 30 min at 37° C. After removing the assay media, the cells were collected in 1.5 ml cold 1 N perchloric acid containing 1 mg/ml theophylline. Cells were lysed by rapid freezing and thawing and then centrifuged. The supernatants were neutralized and then assayed for cAMP as previously described (D. L. Segaloff et al., *J. Biol. Chem.* 25:11420 (1981)).

As shown in FIG. 4A, intact transfected cells exposed to increasing concentrations of $^{125}$I-CG (overnight at 4° C.) specifically bound hormone in a concentration-dependent and saturable manner. No specific binding was observed to untransfected cells at any concentration of $^{125}$I-CG tested. A parallel group of cells were incubated 30 min at 37° C. with varying concentrations of CG in the presence of the phosphodiesterase inhibitor 3-isobutyl-1 -methylxanthine. Results shown are corrected for non-specific binding and represent the mean±range of duplicate determinations.

As shown in FIG. 4B, in contrast to untransfected cells which showed no elevation of cAMP levels in response to CG, transfected cells displayed a concentration-dependent and saturable increase in intracellular cAMP when exposed to CG. The results shown represent the mean±range of duplicate determinations.

The concentrations of CG required to cause an increase in CG binding and cAMP accumulation in cells transfected with pCLHR were found to be comparable to those that elicit these responses in LH/CG-R-bearing gonadal cells (M. E. Pereira et al., *J. Biol. Chem.* 262:6093 (1988); K. Buettner et al., *J. Biol. Chem.* 259:15078 (1984)). These results clearly demonstrate that the cloned cDNA encodes for an intact and functional LH/CG-R protein.

EXAMPLE 11

Tissue and Cell Specific Expression of LH/CG-R mRNA

Figure 5:
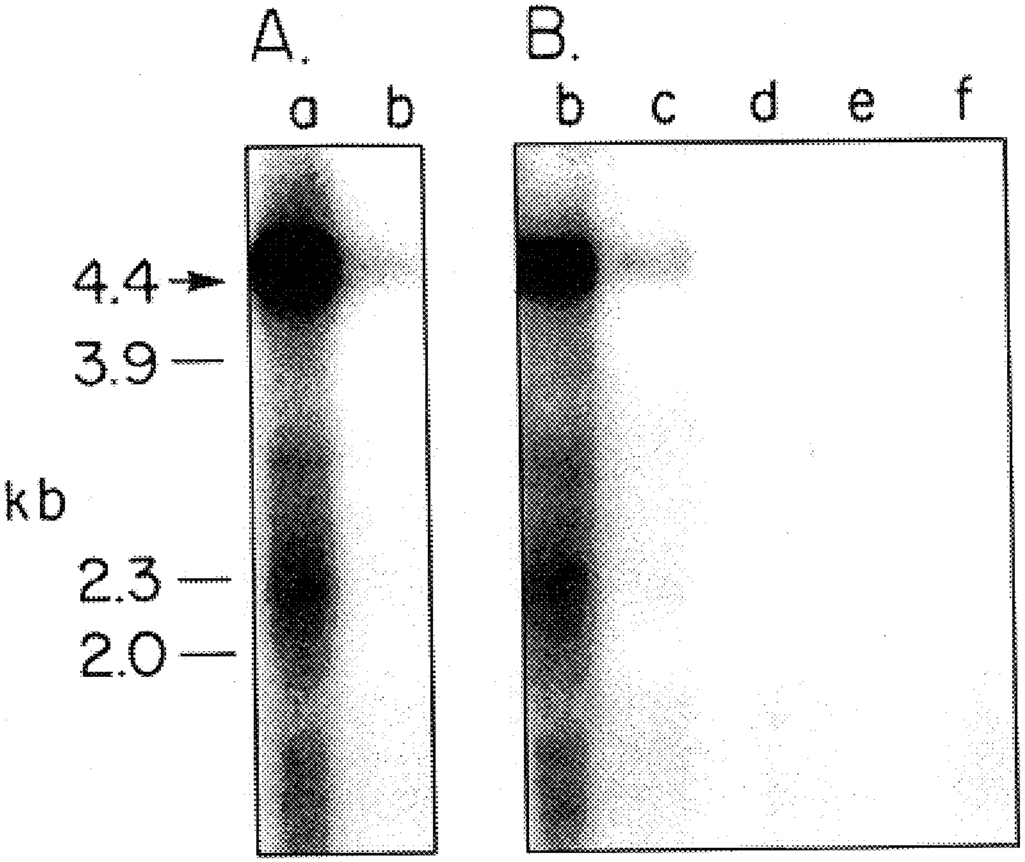

Northern blots prepared from the RNA of different rat tissues demonstrated tissue specificity of LH/CG-R mRNA expression (FIG. 5).

In detail, total RNA was prepared from the ovaries of immature rats rendered pseudopregnant (N. Rosemblit et al., *Endocrinology* 123:2284 (1988)) or from tissues of 60 day old rats as described by C. Auffrey et al. (*Eur. J. Biochem.* 107:303 (1980)). The RNA was resolved on 1% agarose gels containing formaldehyde and blotted onto a nylon membrane (ICN). Following manufacturer's procedures, the membrane was prehybridized and then hybridized overnight at 42° C. using a nick translated $^{32}$P-labeled pGEM-3Z vector (Promega) containing the PCR-generated LH/CG-R DNA. The blot was washed 4 times in 2×SSC and 0.1% SDS at room temperature (5 min per wash). The resulting blot was exposed 6h (FIG. 5, Panel A) or overnight (FIG. 5, Panel B) to X-ray film (at −70° C.) with intensifying screens.

A distinct band corresponding to a 4.4 kb mRNA was observed in RNA prepared from the ovaries of psuedopregnant rats as well as from ovaries and testes of adult rats. Smaller hybridizing species were also observed during longer exposure times. The relative abundance of the 4.4 kb mRNA species was significantly greater in the ovaries of pseudopregnant rats than in the ovaries of non-pregnant adult female rats or the testes of adult rats. This finding is consistent with relative levels of $^{125}$I-CG binding observed in these tissues (M. Ascoli et al., *Endocrine Rev.* 10:27 (1989)). No LH/CG mRNA was observed in RNA prepared from rat lung, liver, or kidney.

To analyze cell specific expression of LH/CG-R mRNA, in situ hybridization of the LH/CG-R cDNA to tissue slices prepared from 9-day pregnant rat ovaries was performed.

In detail, tissue fixation and in situ hybridization were performed by the method of Wilcox et al. (J. N. Wilcox et al., *J. Clin. Invest.* 82:1134 (1988)) with the following modifications. Prior to hybridization, the sections were treated with 4% paraformaldehyde (10 min) and proteinase K (5–10 $\mu$g/ml) for 5–10 min. Prehybridization was performed for 1 hour at 42° C. in 100 $\mu$l of hybridization buffer containing 50% formamide, 0.1 M NaCl, 20 mM Tris pH 8.0, 5 mM EDTA, 1× Denhardt's solution, 10% dextran sulfate, and 10 mM DTT. Hybridization was initiated by the addition of 600,000 cpm of labeled probe in 20 ml of buffer and proceeded overnight at 55° C. $^{35}$S-labeled sense and anti-sense probes were obtained from PCR-generated LH/CG-R DNA cloned into pGEM-3Z vector (Promega). The specific activity of the probes was approximately 100 Ci/mmol. Exposure times were 1–3 weeks (micrographs displayed are 2 week exposures).

Prominent hybridization of the radiolabeled antisense strand was observed to the corpora lutea and to the theca and interstitial cells. No hybridization to the granulosa cells was seen, consistent with the immature state of the non-luteinized follicles. The observed distribution and relative intensities of hybridizing mRNA (i.e. intense staining of the corpora lutea and less intense staining of theca and interstitial cells) is consistent with previously reported $^{125}$I-CG autoradiography in the rat ovary (A. J. Zeleznik et al., *Endocrinology* 95:818 (1974)). These findings provide further evidence that the cloned cDNA encodes the functional LH/CG-R expressed in specific subsets of ovarian cells.

EXAMPLE 12

Structural Features of the Receptor

In summary, a cDNA molecule encoding the rat luteal LH/CG- receptor (LH/CG-R) was isolated utilizing a DNA probe generated in a polymerase chain reaction with oligonucleotide primers based on peptide sequences of purified receptor protein. As predicted from the cDNA sequence, the LH/CG-receptor has a 26 residue signal peptide, a 341 residue extracellular domain displaying an internal repeat structure characteristic of members of the leucine-rich glycoprotein (LRG) family, and a 333 residue region containing seven transmembrane segment. The latter region displays sequence similarity with all members of the G protein-coupled rhodopsin/b-adrenergic receptor family. Hence, the LH/CG-R gene may have evolved by recombination of LRG and G protein-coupled receptor genes. Cells engineered to express LH/CG-R cDNA bind CG with high affinity and show elevated cAMP levels when exposed to hormone. As revealed by Northern analysis and in situ hybridization, the 4.4 kb cognate mRNA is prominently localized in the rat ovary.

Thus, the molecular cloning and expression of a full-length cDNA for the rat luteal LH/CG-R was accomplished. This cDNA encodes a single polypeptide that binds hormone and stimulates adenylate cyclase. Localization of the receptor mRNA in the ovary corresponds to that of hormone binding. The deduced amino acid sequence suggests that the LH/CG-R is evolutionarily related to other G protein-coupled receptors as it contains seven transmembrane regions. However, unlike other such receptors, the LH/CG-R contains a large extracellular domain presumably involved in ligand binding.

Functional and morphological evidence indicates that the protein sequence encoded by the cloned cDNA represents the rat ovarian LH/CG-R. This protein displays the structural features of both a leucine-rich proteoglycan (extracellular domain) and of a G protein-coupled receptor. Other members of the G protein-coupled receptor family bind small ligands (i.e. serotonin or acetylcholine). Whereas binding of such ligands is thought to occur at sites formed by the assembly of the seven transmembrane helices (T. Frielle et al., *Proc. Nat. Acad. Sci. USA* 85:9494 (1988); R. A. F. Dixon et al., *Nature* 326:73 (1987); S. K. F. Wong et al., *J. Biol. Chem.* 263:7925 (1988); E. A. Dratz et al., *Trends Biol. Sci.* 8:128 (1983)), LH and CG are thought to bind to a site on the extracellular part of this receptor (K. P. Keinanen et al., *Biochem. J.* 239:83 (1986); I.-C. Kim et al., *J. Biol. Chem.* 261:3807 (1986)). Thus, the large extracellular domain and the specific mechanism of hormone-mediated signal transduction set the LH/CG-R apart from other G protein-coupled receptors. This receptor may originate through the recombination of genes encoding a hormone-binding glycoprotein and a seven-transmembrane protoreceptor.

EXAMPLE 13

Isolation of FSH-Receptor (FSH-R) cDNA

Polyadenylated RNA isolated from rat testicular Sertoli cells was used as a template for reverse transcriptase. The resulting cDNA served for the construction of a library in λgt10. An aliquot ($1\times10^6$ clones) was screened for clones with sequence similarity to two probes derived from the LH/CG-R cDNA (nucleotides 1–483 and 1499–2604). Several positive clones were isolated and cloned cDNAs sequenced as described in F. Sanger et al., *Proc. Natl. Acad. Sci. USA,* 74:5463–5467 (1977) after subcloning into M13 vectors (J. Vieira and J. Messing, *Meth Enzymol.,* 153:3–11 (1987)). The nucleotide and predicted amino acid sequences of this receptor are shown in FIG. 6.

The translation initiation codon at position 1 defines the start of a 2076 nucleotide open reading frame specifying an N-terminal 17 residue signal sequence followed by a largely hydrophilic domain of 348 residues of putatively extracellular location. This domain contains three N-linked glycosylation sites. It is followed by a structure of 264 residues which comprises seven transmembrane segments. These segments are the hallmark of G protein-coupled receptors. Similar to other such receptors, the 63 residue C-terminus of the FSH-R is proposed to be located intracellularly and contains several amino acids (Ser, Thr, Tyr) whose phosphorylation may regulate receptor activity (K. Palczewski et al., *Biochemistry,* 27:2306–2313 (1988); J. L. Benovic et al., *Proc. Natl. Acad. Sci. USA,* 83:2797–2801 (1986)). However, these residues are not part of consensus phosphorylation sites as in other receptors. The mature FSH-R is predicted to comprise 675 amino acids (75K mol. wt.) and to constitute an integral membrane glycoprotein.

Comparison Between FSH-R and LH/CG-R

It is illuminating regarding the proposed similarities in function to compare the gonadotropin receptors FSH-R and LH/CG-R (FIG. 7). Both molecules are of similar size and display the same structural design. On the level of primary structure, the extracellular domains share approximately 50% sequence similarity while the domains defined by the seven transmembrane segments display 80% sequence identity. The areas of highest sequence divergence comprise the N-terminus, a 40 residue region preceding the first transmembrane segment and the 30 residues encompassing the C-terminus.

As noted for the extracellular domain of the LH/CG-R, the homologous domain in the FSH-R can be viewed as being composed of 14 imperfectly-replicated units of approximately 20 residues each (FIG. 8). The motif underlying this repeat is also found in other proteins and is known as leucine-rich repeat (L. Patthy, *J. Mol. Biol.,* 198:567–577 (1987). A characteristic feature of members of the leucine-rich repeat family is a purported tendency to interact with both hydrophilic and hydrophobic protein surfaces (J. A. Lopez et al., *Proc. Natl. Acad. Sci. USA,* 84:5615–5619 (1987). This property may be important regarding the function of the extracellular domain of gonadotropin receptors.

The alignment of the extracellular domains of both receptors (FIG. 7) shows that repeats with the highest sequence divergence (repeats 12 and 13) are also the least conserved relative to the underlying motif. Notably, this region is of different length between the gonadotropin receptors and the recently characterized TSH receptor (M. Parmentier et al., *Science,* 246:1620–1622 (1989); F. Libert et al., *Biochem. Biophys. Res. Comm.,* 5:1250–1255 (1989); Y. Nagayama et al., *Biochem. Biopyhys. Res. Comm.,* 165:1184–1190 (1989)) and is variable in sequence between glycoprotein hormone receptors from different species (F. Libert et al., supra), indicating that it is unlikely to be involved in hormone recognition. The alignment further reveals eight conserved cysteine residues, two of which are in adjacent positions. Interestingly, several of these residues are found in well-conserved regions comprising 13 and 15 consecutive amino acids. Since these cysteines are also conserved in the TSH-R (M. Parmentier et al., supra; F. Libert et al., supra; Y. Nagayama, et al., supra), the formation of disulfide bonds seems to be crucial for the conformational integrity of the large extracellular domain of glycoprotein hormone receptors.

A differential pattern of sequence conservation is also observed for the seven transmembrane segments. While TMIII and TMVII are highly conserved, TMIV and TMV contain many substitutions. Although the overall sequence similarity to other G protein-coupled receptors is low (K. C. McFarland et al., *Science,* 245:494–499 (1989)), the aspartic acid residue within TMII and the asparagine within TMVII, two conserved residues in G protein-coupled receptors (K. C. McFarland et al., supra; C. D. Strader et al., *Proc. Natl. Acad. Sci. USA,* 84:4384–4388 (1987)), are also present in the two gonadotropin receptors. So are proline residues in TMIV, TMVI and TMVII and the two cysteine residues that are thought to form a disulfide bridge between the second and third extracellular loops in many G protein-coupled receptors (R. A. F. Dixon et al., *EMBO J.,* 6:3269–3275 (1987)).

In the gonadotropin receptors, the third intracellular loop flanked by TMV and TMVI is short and quite divergent. The low degree of sequence similarity in this region is as seen for subtypes of other G protein-coupled receptors (E. G. Peralta et al., *EMBO J.,* 6:3923–3929 (1987)). In some of these receptors the region bordered by, and comprising part of, TMV and VI appears to be involved in the coupling to G protein (B. K. Kobilka et al., *Science,* 240:1310–1316 (1988); R. A. F. Dixon et al., *Nature* 326:73–77 (1987)). A sequence of eight amino acids at the C-terminal end of this intracellular loop is well-conserved between both gonadotropin receptors (E. G. Peralta et al., supra). A similar sequence implicated in coupling to $G_5$ can be found in the β-adrenergic receptor (R. A. F. Dixon et al., *Nature*, supra). The interaction with the G protein may occur via an amphiphilic α-helical structure (C. D. Strader et al., *FASEB J.,* 3:1825–1832 (1989)) formed by this peptide sequence. A helical wheel analysis performed on the conserved eight residue sequence in the FSH and LH/CG receptors reveals that the charged side chains are located on one side and the hydrophobic ones on the opposite face of the helix, as proposed for the homologous region of $\alpha_2$ and $\beta_2$ adrenergic receptors (C. D. Strader et al., *FASEB J.,* supra).

EXAMPLE 14

Functional Expression of FSH-Receptor (FSH-R) cDNA

Highly purified oFSH (NIDDK-oFSH-17; 20 U/mg), hCG (CR-123; 12,780 IU/mg), and hTSH (NIDDK-hTSH-1-6; 17 IU/mg) were generous gifts from the National Hormone and Pituitary Program of the NIDDK (N.I.H.).

The expression vector pCFSH-R was constructed by introducing the entire coding region of the cloned cDNA contained on an EcoRi-Bam HI fragment (nucleotides −77 to 2095) into the pCIS vector (C. M. Gorman et al., *Virology,* 171:377–385 (1989)). Exponentially growing human embryonic kidney cells 293 (ATCC CRL 1573) in 34 mm dishes were transfected with this expression vector (C. Chen and H. Okayama, *Mol. Cell. Biol.,* 7:2745–2751 (1987)). After 42 hr intact cells were assayed for hormone-stimulated cAMP production. Each dish was washed once with 3 ml of warm DMEM medium containing 10% fetal calf serum and placed in 1 ml of the serum-free DMEM-medium buffered with 25 mM HEPES pH 7.4 containing 0.1 mM 3-isobutyl-1-methylxanthine. After a 15-minute incubation period at 37° C, highly purified glycoprotein hormone (oFSH, hTSH, or hCG) was added and the incubation was continued for 30 min at 37° C. The assay was stopped by rapid freezing and thawing of the cells in liquid nitrogen and then 1.2 ml cold ethanol was added to each dish. The cell debris and precipitated protein were removed by centrifugation (10 min; 13,000×g) and 5 μl or 50 μl of the supernatant was assayed for cAMP using an Amersham kit. As shown in FIG. 9 and in Table 3, cells expressing the cloned receptor displayed an FSH dependent and saturable increase in intracellular cAMP. Untransfected and mock-transfected cells did not show this response.

TABLE 3

Adenylyl cyclase stimulation in FSH-R expressing cells

| Hormone (25 nM) | cAMP (pmoles/$10^6$ cells) |
|---|---|
| none | 9.0 |
| oFSH | 700.0 |
| hCG | 7.6 |
| hTSH | 12.0 |

Legend to Table 3: 293 cells were transiently transfected using the pCFSH-R expression construct and incubated in the presence of 26 nM of several glycoprotein hormones; The cAMP accumulated during 30 min of hormonal stimulation reflects the specificity of the FSH-R to its natural ligand.

The concentration of FSH required to elicit half-maximal stimulation of this response (2–3 ng/ml, −80 pM) is comparable to that seen for hCG and its receptor (K. C. McFarland et al., supra) and is well within the range of values reported for the FSH receptor (H. Abou-Issa and L. E. Reichert, Jr., *J. Biol. Chem.,* 251:3326–3337 (1976)). In contrast, hCG, even at concentrations up to 25 nM did not evoke a cAMP response in FSH-R expressing cells (Table 3). In the absence of data obtained with recombinantly-produced FSH and LH, we conclude that the receptor recognition of different gonadotropins is selective.

DISCUSSION

The FSH-R displays structural similarities with the LH/CG-R. Although some studies by others have suggested that the LH/CG and the FSH receptors are composed of multiple subunits (L. E. Reichert, Jr. and B. Dattatreyamurty, *Biology of Reproduction,* 40:13–26 (1989); J. Shin and T. H. Ji, *J. Biol. Chem.,* 260:12822–12827 (1985); R. A. Smith et al., *J. Biol. Chem.,* 260:14297–14303 (1985); J. Shin and T. H. Ji, *J. Biol. Chem.,* 260:14020–14025 (1985); R. A. Smith et al., *J. Biol. Chem.,* 261:9850–9853 (1986); J. Shin and T. H. Ji, *J. Biol. Chem.,* 260:12828–12831 (1985), reviewed in M. Ascoli and D. L. Segaloff, *Endocrine Rev.,* 10:27–44 (1989)), biochemical studies on the LH/CG-R have shown that it is composed of a single polypeptide with a molecular weight of 92K when analyzed on SDS gels in the presence or absence of disulfide reducing agents (N. Rosemblit et al., *Endocrinology,* 123:2284–2289 (1988)). As the LH/CG-R has been shown to be readily proteolyzed into smaller sized fragments (see M. Ascoli and D. L. Segaloff, supra for review), it is reasonable to postulate that the FSH-R may be similarly susceptible to proteolysis, and that this may account for the discrepant reports on its structure. The molecular cloning and functional expression of the cDNAs for the LH/CG-R (K. C. McFarland et al., supra) and the FSH-R demonstrate that the gonadotropin receptors are indeed single polypeptides.

Reflecting a unique mechanism of receptor activation, both the FSH-R and the LH/CG-R are characterized by the presence of a large, glycosylated domain of putative extracellular location which is grafted onto a structure containing seven transmembrane segments and displaying homology to G protein-coupled receptors. The same structural design also characterizes the TSH-R (M. Parmentier et al., supra; F. Libert et al., supra; Y. Nagayama et al., supra), another member of the glycoprotein hormone family. In comparison to other G protein-coupled receptors, this unique design suggests that the extracellular domain is responsible for the recognition and binding of the dimeric hormones.

The functional significance of the internal repeat structure of the extracellular domain of glycoprotein hormone receptors can only be the subject of conjecture. It is likely that the amphiphilic nature of the repeats confers the dual property of interacting with hormone and transmembrane domains. Such an interaction seems crucial for receptor activation which, for most other G protein-coupled receptors, is effected by the binding of a small ligand to a spatially defined site within the seven transmembrane segments. Considering the evolutionarily-conserved basic mechanism of receptor activation, it is entirely possible that selected amino acid residue side chains of the gonadotropins substitute for the customary small ligands. In this model, the activating residues are correctly positioned by the binding of the hormone to the extracellular domain. In a variation of this model, residues of the extracellular domain itself, upon binding hormone, may contact essential sites in the transmembrane segments.

One important factor when considering the possible mechanisms by which the binding of glycoprotein hormones to their respective receptors causes the activation of the $G_5$ protein is the role of the hormone carbohydrate moieties in this activation process (M. R. Sairam, *FASEB J.,* 3:1915–1926 (1989); M. M. Matzuk et al., *J. Biol. Chem.,* 264:2409–2414 (1989)). Although deglycosylated glycoprotein hormones bind with high affinity to their receptors, they elicit little or no activation of cAMP production (M. M. Matzuk et al., supra). The concept of antihormones has been proposed to describe the FSH antagonistic effects of naturally occurring glycosylation variants of FSH (K. D. Dahl et al., *Science,* 239:72–74 (1988)).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A recombinant nucleic acid molecule comprising a nucleic acid sequence encoding the LH/CG receptor which binds luteinizing hormone, wherein said nucleic acid sequence is selected from the group consisting of (a) a nucleic acid sequence that encodes LH/CG receptor having the amino acid sequence of mature LH/CG receptor shown in FIG. 1, (b) a nucleic acid sequence that hybridizes under high stringency conditions with the mature-LH/CG-receptor-encoding DNA sequence shown in FIG. 1, or its complementary DNA sequence, and (c) a nucleic acid sequence having the mature-LH/CG-receptor-encoding nucleic acid sequence shown in FIG. 1.

2. The recombinant molecule of claim 1 which is free of introns.

3. The recombinant molecule of claim 1 wherein said LH/CG receptor contains at least one sequence selected from the group consisting of:

(a) Glu-Leu-Ser-Gly-Ser-Arg-Cys-Pro-Glu-Pro;

(b) Pro-Arg-Ala-Gly-Leu-Ala-Arg-Leu-Ser-Leu;

(c) Leu-Asn-Glu-Val-Val-Lys-Ile-Glu-Ile-Ser;

(d) Ser-Glu-Leu-Leu-Ile-Gln-Asn-Thr-Lys-Asn;

(e) Met-Asn-Asn-Glu-Ser-Val-Thr-Leu-Lys-Leu;

(f) Thr-Leu-Thr-Tyr-Pro-Ser-His-Cys-Cys-Ala;

(g) Val-Leu-Ile-Trp-Leu-Ile-Asn-Ile-Leu-Ala;

(h) Val-Phe-Ala-Ser-Glu-Leu-Ser-Val-Tyr-Thr;

(i) Ala-Ile-Leu-Ile-Phe-Thr-Asp-Phe-Thr-Cys;

(j) Phe-Thr-Lys-Ala-Phe-Gln-Arg-Asp-Phe-Leu; and (k) Arg-Ala-Glu-Leu-Tyr-Arg-Arg-Lys-Glu-Phe.

4. The recombinant molecule of claim 1 wherein said DNA molecule encoding LH/CG receptor contains a contiguous nucleic acid sequence from FIG. 1 encoding an amino acid sequence selected from the group consisting of:

(a) Glu-Leu-Ser-Gly-Ser-Arg-Cys-Pro-Glu-Pro;

(b) Pro-Arg-Ala-Gly-Leu-Ala-Arg-Leu-Ser-Leu;

(c) Leu-Asn-Glu-Val-Val-Lys-Ile-Glu-Ile-Ser;

(d) Ser-Glu-Leu-Leu-Ile-Gln-Asn-Thr-Lys-Asn;

(e) Met-Asn-Asn-Glu-Ser-Val-Thr-Leu-Lys-Leu;

(f) Thr-Leu-Thr-Tyr-Pro-Ser-His-Cys-Cys-Ala;

(g) Val-Leu-Ile-Trp-Leu-Ile-Asn-Ile-Leu-Ala;

(h) Val-Phe-Ala-Ser-Glu-Leu-Ser-Val-Tyr-Thr;

(i) Ala-Ile-Leu-Ile-Phe-Thr-Asp-Phe-Thr-Cys;

(j) Phe-Thr-Lys-Ala-Phe-Gln-Arg-Asp-Phe-Leu; and (k) Arg-Ala-Glu-Leu-Tyr-Arg-Arg-Lys-Glu-Phe.

5. The recombinant nucleic acid molecule of claim 1, wherein the nucleic acid sequence is selected from the group consisting of (a) a nucleic acid sequence that encodes LH/CG receptor having the amino acid sequence of mature LH/CG receptor shown in FIG. 1, and (b) a nucleic acid sequence having the mature-LH/CG-receptor-encoding nucleic acid sequence shown in FIG. 1.

6. The recombinant molecule of claim 1 which is a replicatable vector.

7. The recombinant molecule of claim 6 which expresses said LH/CG receptor when present in a host cell.

8. The recombinant molecule of claim 7 wherein said host cell is a eukaryotic cell.

9. The recombinant molecule of claim 8 wherein said eukaryotic cell is a yeast or a mammalian cell.

10. The recombinant molecule of claim 7 wherein said host cell is a prokaryotic cell.

11. The recombinant molecule of claim 10 wherein said prokaryotic cell is an *E. coli* cell.

12. A method for producing LH/CG receptor which comprises:

(a) constructing a vector that includes a nucleic acid sequence which encodes said LH/CG receptor that binds luteinizing hormone, wherein said nucleic acid sequence is selected from the group consisting of (i) a nucleic acid sequence that encodes LH/CG receptor having the amino acid sequence of mature LH/CG receptor shown in FIG. 1, (ii) a nucleic acid sequence that hybridizes under high stringency conditions with the mature-LH/CG-receptor-encoding DNA sequence shown in FIG. 1, or its complementary DNA sequence, and (iii) nucleic acid sequence has the mature-LH/CG-receptor-encoding encoding nucleic acid sequence shown in FIG. 1;

(b) transforming a host cell with said vector;

(c) culturing said transformed cell in a culture medium under conditions sufficient for said cell to express said gene sequence; and (d) recovering said expressed LH/CG receptor.

13. The method of claim 12 wherein said transformed cell is a eukaryotic cell.

14. A recombinant nucleic acid molecule comprising a nucleic acid sequence encoding an LH/CG receptor extracellular domain which binds luteinizing hormone, wherein the nucleic acid sequence is selected from the group consisting of (a) a nucleic acid sequence that encodes LH/CG receptor extracellular domain amino acid sequence of mature LH/CG receptor shown in FIG. 1, (b) a nucleic acid sequence that hybridizes under high stringency conditions with mature-LH/CG-receptor-extracellular-domain encoding DNA sequence shown in FIG. 1, or its complementary DNA sequence, and (c) a nucleic acid sequence of mature-LH/CG-receptor-extracellular domain encoding nucleic acid sequence shown in FIG. 1.

15. An expression vector comprising the recombinant nucleic acid molecule of claim 14.

16. A host cell comprising the expression vector of claim 15.

17. A method for producing LH/CG receptor extracellular domain that binds luteinizing hormone which comprises:

(a) culturing the host cell of claim 16 in a culture medium under conditions sufficient for the host cell to express the LH/CG receptor extracellular domain, and (b) recovering the expressed LH/CG receptor extracellular domain.

18. The method of claim 7 wherein said expressed LH/CG receptor extracellular domain is secreted into said culture medium by said transformed host cell, and wherein said expressed hormone receptor is recovered from said culture medium.

* * * * *